United States Patent
Snyder et al.

(10) Patent No.: US 12,426,571 B2
(45) Date of Patent: Sep. 30, 2025

(54) SYSTEM AND METHOD FOR NON-INVASIVE ANIMAL HEALTH SENSING AND ANALYSIS

(71) Applicant: HAFTAL LLC, Jacksonville, FL (US)

(72) Inventors: Michael Snyder, Jacksonville, FL (US); William White, Naples, FL (US); Kyle Nel, Austin, TX (US)

(73) Assignee: HAFTAL LLC, Jacksonville, FL (US)

( * ) Notice: Subject to any disclaimer, the term of this patent is extended or adjusted under 35 U.S.C. 154(b) by 148 days.

(21) Appl. No.: 18/103,727

(22) Filed: Jan. 31, 2023

(65) Prior Publication Data
US 2023/0292705 A1    Sep. 21, 2023

Related U.S. Application Data

(60) Provisional application No. 63/305,404, filed on Feb. 1, 2022.

(51) Int. Cl.
*A01K 5/02* (2006.01)
*A01K 11/00* (2006.01)
*A01K 29/00* (2006.01)

(52) U.S. Cl.
CPC .............. *A01K 5/02* (2013.01); *A01K 11/006* (2013.01); *A01K 29/005* (2013.01)

(58) Field of Classification Search
CPC .......... A01K 5/02; A01K 7/02; A01K 11/006; A01K 29/005
See application file for complete search history.

(56) References Cited

U.S. PATENT DOCUMENTS

| | | | | | |
|---|---|---|---|---|---|
| 4,617,876 | A | * | 10/1986 | Hayes | A01K 11/006 119/908 |
| 5,315,505 | A | * | 5/1994 | Pratt | G16H 10/60 128/920 |
| 6,684,810 | B2 | * | 2/2004 | Martin | A22B 5/0064 119/51.02 |

(Continued)

OTHER PUBLICATIONS

Suh, Jung-Won, "Cardiac Auscultation Using Smartphones: Pilot Study," JMIR mHealth and uHealth, Feb. 28, 2018; 6(2). Retrieved by https://www.ncbi.nlm.nih.gov/pmc/articles/PMC5853766/.

(Continued)

*Primary Examiner* — Joshua J Michener
*Assistant Examiner* — Aaron M Rodziwicz
(74) *Attorney, Agent, or Firm* — Terry M. Sanks, Esq.; Beusse Sanks, PLLC

(57) ABSTRACT

A system for examining an animal that includes a kiosk housing having an analysis zone. The system includes a persuasion delivery device in the analysis zone. The system includes a dispensing machine to dispense an animal attractant to the persuasion delivery device. The system includes a set of sensors located in the analysis zone to sense real-time data related to health of an animal. The set of sensors includes at least one sensor to sense within the analysis zone at least one biological parameter of the animal related to the health. A method is provided using the system that autonomously guides the animal to the analysis zone by a predisposition of the animal to hunt for an animal attractant so that biological parameters of the animal related to the health of the animal are sensed in a stress-free or reduced stress environment.

20 Claims, 46 Drawing Sheets

(56) References Cited

U.S. PATENT DOCUMENTS

| | | | |
|---|---|---|---|
| 7,128,024 B2* | 10/2006 | Doyle, II | C07K 16/081 382/110 |
| 7,670,292 B2* | 3/2010 | Haynes | G01G 13/24 600/443 |
| 9,363,983 B2* | 6/2016 | Doyle | A01K 29/005 |
| 10,080,343 B1* | 9/2018 | Chu | A01K 5/0114 |
| 10,091,972 B1 | 10/2018 | Jensen et al. | |
| 10,143,182 B1* | 12/2018 | Ferro | A01K 27/003 |
| 2006/0267767 A1* | 11/2006 | Pohlkamp | A01K 11/006 340/572.1 |
| 2010/0132629 A1* | 6/2010 | Jalbert | A01K 7/02 119/720 |
| 2012/0116832 A1* | 5/2012 | Dubinsky | A01K 39/0125 700/214 |
| 2012/0326874 A1* | 12/2012 | Kwak | A01K 11/006 340/573.3 |
| 2016/0192619 A1 | 7/2016 | Gibbs | |
| 2016/0192620 A1* | 7/2016 | Hu | A61B 5/01 119/51.02 |
| 2016/0227738 A1* | 8/2016 | Ausman | A01K 5/0142 |
| 2017/0000090 A1* | 1/2017 | Hall | A01K 29/005 |
| 2017/0013802 A1* | 1/2017 | Zimmerman | G06K 7/10366 |
| 2017/0049545 A1* | 2/2017 | Carton | G16Z 99/00 |
| 2017/0161450 A1 | 6/2017 | White et al. | |
| 2017/0223926 A1* | 8/2017 | Ausman | A01K 11/006 |
| 2017/0280687 A1* | 10/2017 | Vrabete | A01K 29/005 |
| 2017/0290290 A1* | 10/2017 | Trottier | A01K 5/02 |
| 2017/0347632 A1* | 12/2017 | Auer | A01K 11/006 |
| 2018/0055434 A1* | 3/2018 | Cheung | A61B 5/16 |
| 2018/0160649 A1* | 6/2018 | Hicks | A01K 7/02 |
| 2019/0124892 A1* | 5/2019 | van Lenthe | A01K 5/0233 |
| 2019/0200643 A1* | 7/2019 | Barber | A23K 50/30 |
| 2020/0093092 A1* | 3/2020 | Soug | B25J 5/007 |
| 2020/0229401 A1* | 7/2020 | Hernandez | A01K 5/0114 |
| 2020/0367470 A1* | 11/2020 | Baudisch | A01K 11/006 |
| 2020/0381119 A1 | 12/2020 | Gibbs et al. | |
| 2021/0065277 A1* | 3/2021 | Bramson | G06Q 30/0631 |
| 2021/0153456 A1* | 5/2021 | Mundell | A01K 15/021 |
| 2021/0289746 A1* | 9/2021 | Villalobos | A01K 5/02 |
| 2022/0061765 A1* | 3/2022 | Nichol | A61B 5/1102 |
| 2022/0211010 A1* | 7/2022 | Seo | A01K 11/00 |
| 2022/0250284 A1* | 8/2022 | Kuo | B29B 7/92 |
| 2023/0083421 A1* | 3/2023 | Mundell | G06V 40/23 119/712 |
| 2023/0092647 A1* | 3/2023 | Mundell | A01K 29/005 119/712 |
| 2023/0165221 A1* | 6/2023 | Petersen | A01K 11/006 119/712 |
| 2024/0180124 A1* | 6/2024 | Cook | A01K 29/005 |

OTHER PUBLICATIONS

Is Your Dog Overweight? Use this Body Condition Scoring Chart to determine if your dog is at a healthy weight. Retrieved by www://aspengrovevet.com/wp-content/uploads/2014/01/dog_chart-BCS.jpg.

* cited by examiner

SYSTEM AND METHOD FOR NON-INVASIVE ANIMAL HEALTH SENSING AND ANALYSIS

CROSS-REFERENCE TO RELATED APPLICATIONS

This application claims priority benefit of U.S. Provisional Application No. 63/305,404, titled "SYSTEM AND METHOD FOR NON-INVASIVE ANIMAL HEALTH SENSING AND ANALYSIS," filed Feb. 1, 2022, which is incorporated in its entirety herein by reference.

BACKGROUND

Embodiments relate to health analysis and, more particularly, to systems and methods for non-invasive animal health sensing, analysis and/or feed manufacturing.

An animal requires periodic monitoring of their health to stay healthy. However, animals can gain weight without the proper diet and nutrients for their breed. It can be inconvenient to schedule a medical appointment for evaluating the animal's weight, for example.

It can be cumbersome for an owner to have a variety of health parameters of their pet monitored on a frequent basis without the high cost of veterinarian visits and in a stress free or reduced stress environment.

SUMMARY

Embodiments relate to health analysis and, more particularly, to systems and methods for non-invasive animal health sensing, analysis and/or food manufacturing.

An aspect of the embodiments provides a system to perform a non-invasive analysis of an animal to detect and/or analyze health including one or more of weight, body form, body temperature, dental condition, breath, heartbeat, and breath using a sensor suite and a computing device.

An aspect includes a system for examining an animal that includes a kiosk housing having an analysis zone. The system includes a persuasion delivery device in the analysis zone. The system includes a dispensing machine to dispense an animal attractant to the persuasion delivery device. The system includes a set of sensors located in the analysis zone to sense real-time data related to health of an animal. The set of sensors includes at least one sensor to sense within the analysis zone at least one biological parameter of the animal related to the health.

An aspect includes a method for sensing at least one biological parameter of an animal. The method includes dispensing a treat into a bowl cavity of a bowl by a system. The method includes autonomously guiding the animal to an analysis zone, having a set of sensors, by a predisposition of the animal to hunt for the treat; and electronically sensing the at least one biological parameter of the animal by the set of sensors as the animal eats the treat in the analysis zone. The method includes providing information associated with the at least one biological parameter.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which.

DETAILED DESCRIPTION

Figure 1:
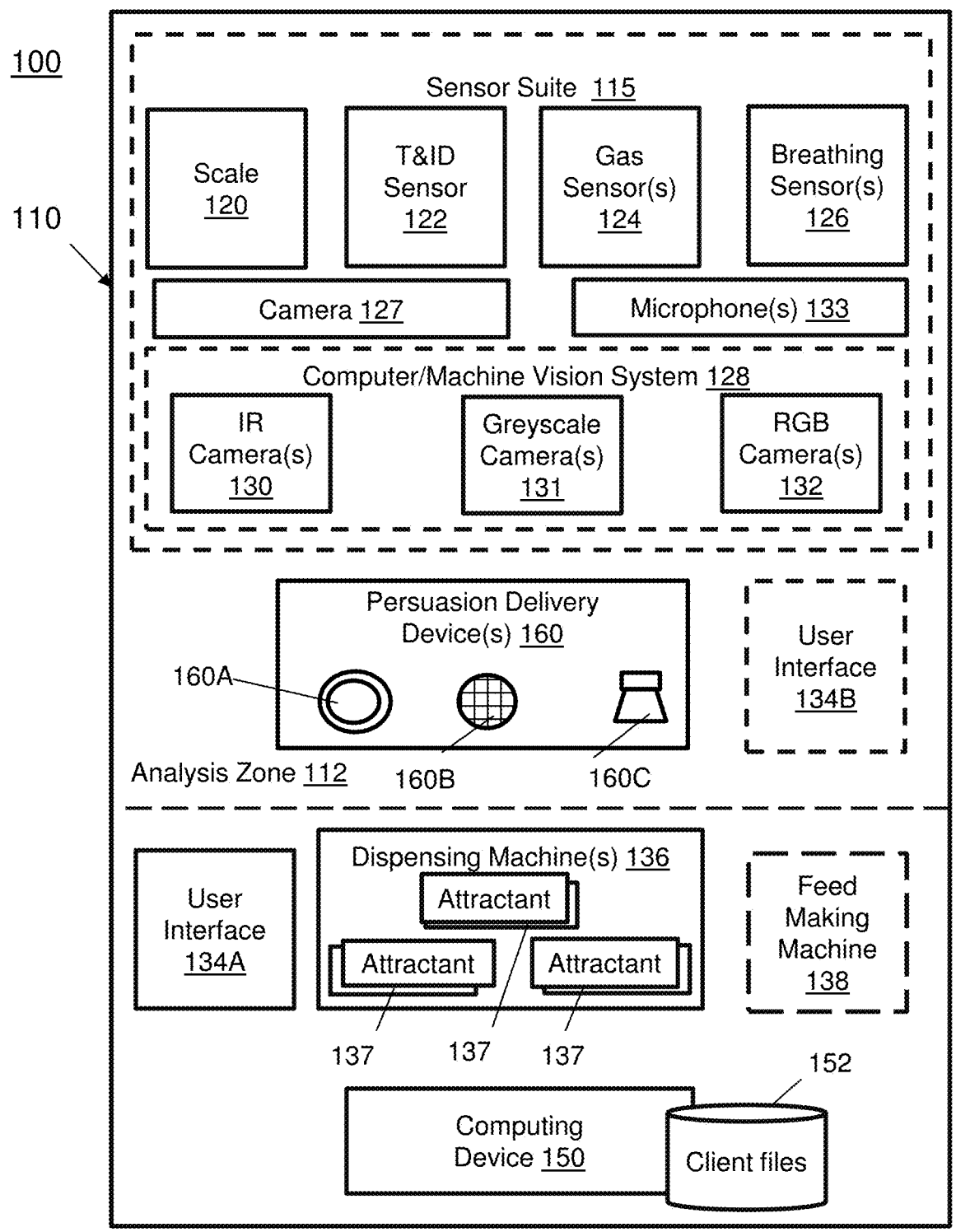
FIG. 1 shows a block diagram of a system for non-invasive animal health sensing and analysis according to an embodiment.

Embodiments are described herein with reference to the attached figures wherein like reference numerals are used throughout the figures to designate similar or equivalent elements. The figures are not drawn to scale and they are provided merely to illustrate aspects disclosed herein. Several disclosed aspects are described below with reference to non-limiting example applications for illustration. It should be understood that numerous specific details, relationships, and methods are set forth to provide a full understanding of the embodiments disclosed herein. One having ordinary skill in the relevant art, however, will readily recognize that the disclosed embodiments can be practiced without one or more of the specific details or with other methods. In other instances, well-known structures or operations are not shown in detail to avoid obscuring aspects disclosed herein. The embodiments are not limited by the illustrated ordering of acts or events, as some acts may occur in different orders and/or concurrently with other acts or events. Furthermore, not all illustrated acts or events are required to implement a methodology in accordance with the embodiments.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Furthermore, unless otherwise clear from the context, a numerical value presented herein has an implied precision given by the least significant digit. Thus, a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

The embodiments provide a system to capture, analyze and communicate vital signs and physical characteristics of a pet within a walk-in analysis zone of a pet health-monitoring kiosk.

The embodiments may include a system that includes a kiosk housing with a walk-in analysis zone and a set of sensors of a sensor suite to autonomously sense at least one health parameter. The system uses guidance of the animal to the sensors of the sensor suite by a predisposition of the animal to seek out and/or be guided in the direction of a persuasion delivery device delivering a dispensed attractant.

The embodiments may include a system that includes a kiosk housing with a treat dispensing chute to a bowl in proximity to a set of sensors of the sensor suite to autonomously sense at least one health parameter. The system uses guidance of the animal to the sensors of the sensor suite by a predisposition of the animal to seek out the treat dispensed in the bowl.

The embodiments may include a system that includes a kiosk housing with a speaker to output a dispensed audio sounds in proximity to a set of sensors of the sensor suite to autonomously sense at least one health parameter. The system uses guidance of the animal to the sensors of the sensor suite by a predisposition of the animal to seek out the audio sounds.

The embodiments may include a system that includes a kiosk housing with an orifice to deliver a dispensed odor in proximity to a set of sensors of the sensor suite to autonomously sense at least one health parameter. The system uses guidance of the animal to the sensors of the sensor suite by a predisposition of the animal to seek out the odor.

The embodiments of the system provide an owner of an animal to have their animal's health captured and tracked more frequently than with normal frequency of required vet visits, and in a stress free/reduced stress environment. The frequency of visits and the stress-free environment may provide for a more accurate monitoring system to maintain a pet's health.

In some embodiments, the system may provide a pet owner the ability to perform wellness checks on their pet without going to a veterinarian's office.

The embodiments provide a system that may provide remote (autonomous capable) operation and analysis for detection and measurement of vital parameters such as by sending sensor data offsite to be analyzed.

The embodiments provide a system to capture and analyze a pet's health in a kiosk housing with a walk-in analysis zone, communicate the captured pet's health data with remote facilities and a cloud computing system, and produce or package food for the pet based on a comparative analysis and diet formulation.

The embodiments of the system determine the overall health of a pet while minimizing the stress that the animal undergoes during the data capture and analysis processes. Understanding the pet's body condition combined with weight and temperature, especially over time, can be a good indication of the overall health of the pet. Diet and lifestyle changes can be made prior to problems (health) being created due to the infrequent nature of health check-ups. By comparing information gathered during the health analysis with dietary databases, the system is able to determine and recommend appropriate feed nutrients to provide an improved diet for the animal based on the sensed data at the point of inspection, eliminating time and saving costs that are traditionally associated with custom diets or health assessments. The system may produce or package animal food with the recommended feed nutrients, based on the sensed data.

FIG. 1 shows a block diagram of a system 100 for non-invasive animal health sensing and analysis. The system 100 is configured to perform a non-invasive analysis of an animal to detect and/or analyze one or more of weight, body form, body temperature, breath, heartbeat and breathing using a sensor suite 115 and a computing device 150. The system 100 includes a housing 110, such as a kiosk housing, to receive a single animal in a walk-in analysis zone 112, as will be described later, to detect and analyze health parameters and vitals associated with the animal. The sensor suite 115 is arranged within or in proximity to the analysis zone 112. The computing device 150 may store or be connected to memory for storing client files 152.

The housing 110 may include a housing that is movable such as by wheels. The housing may include a foldable walk-in analysis zone or non-foldable walk-in analysis zone. Example housings with foldable walk-in analysis zones will be described in relation to FIGS. 22A-22D, 23A and 23B. The walk-in analysis zone may include a grooming station, as will be described in relation to FIG. 24. The housing 110 may include shelves for advertising merchandise or to store supplies, animal attractants, etc.

The sensor suite 115 may detect other body and health features such as an eye condition, growths and other ailments that can be captured by the sensor suite 115 in the walk-in analysis zone. The health features or parameters may include weight of the animal, temperature of the animal, and/or skin or coat details of the animal. Each sensor may have a sample collector in proximity to the persuasion delivery device installed in the walk-in analysis zone to capture a respective biological parameter. A sample collector may include a piping to capture the breath vapor, for example. A sample collector may include a lens of a camera, for example. A sample collector may include a component of a microphone, for example.

The system 100 may include at least one persuasion delivery device 160. The at least one persuasion delivery device 160 may be coupled to at least one dispensing machine 136 to dispense at least one animal attractant 137 or persuasion. The at least one persuasion device 160 may be a bowl 160A, an orifice or permeable membrane 160B and/or a speaker 160C. The at least one dispensing machine 136 may include or be coupled to the computing device 150. The at least one animal attractant 137 may include an animal treat to be dispensed to the bowl 160A, an odor or smell dispensed to the orifice or permeable membrane 160B, and/or one or more sounds dispensed to the speaker 160C that provides a persuasion. The dispensing machine 136 may include a treat dispensing machine, an odor dispensing machines and/or a sound dispensing machine.

Figure 6A:
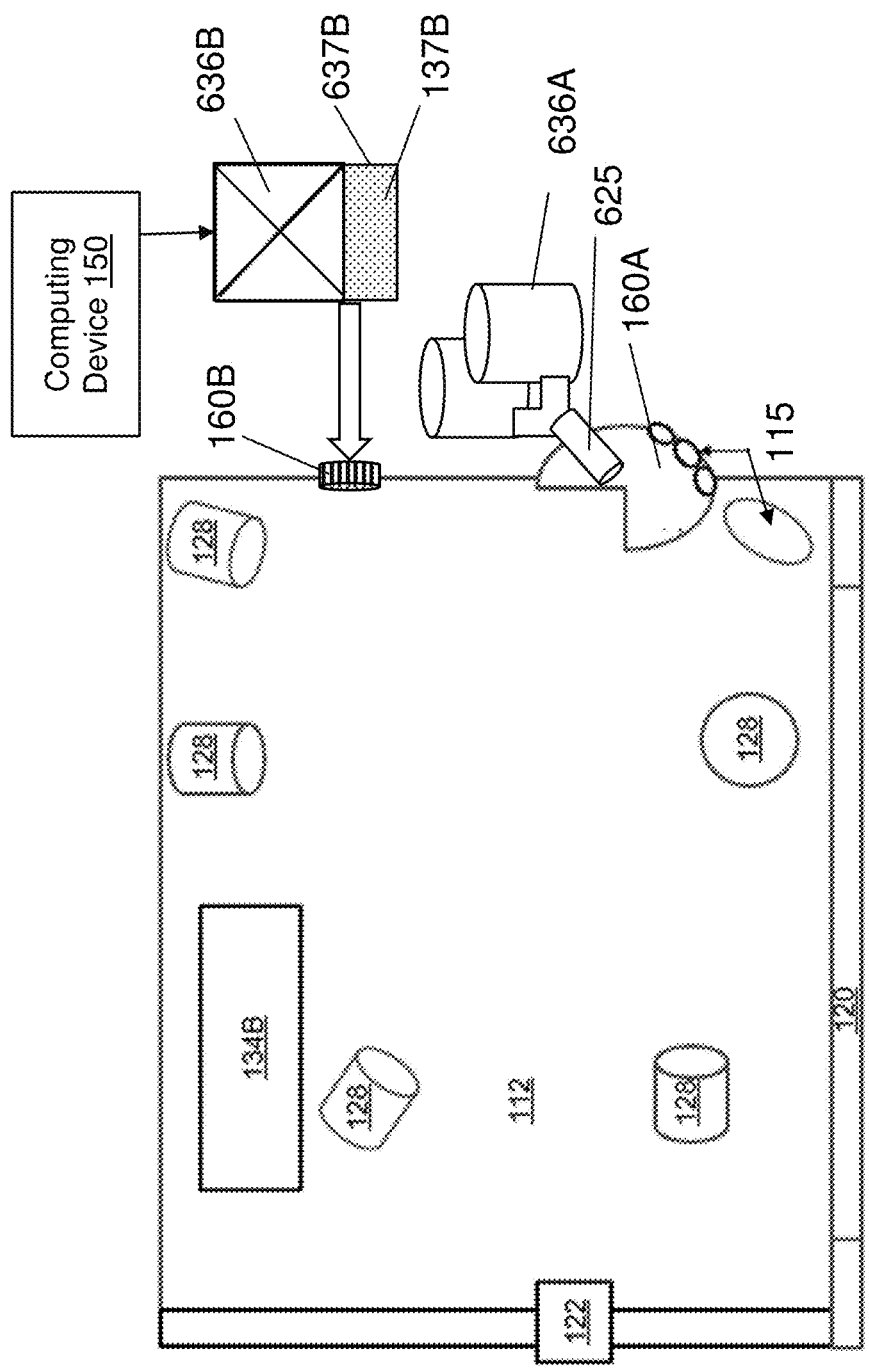
FIG. 6A illustrates a side view of the components of the analysis zone with two persuasion delivery devices, such as the bowl and orifice or permeable membrane.

FIG. 6A illustrates a side view of the components of the analysis zone with two persuasion delivery devices, such as the bowl 160A and orifice or permeable membrane 160B. The orifice or permeable membrane 160B may deliver an odor or smell representative of an animal attractant 137B from the at least one dispensing machine 636B and into the analysis zone 112. The at least one dispensing machine 636B may include at least one scent diffuser controlled by the computing device 150 and a scent supply 637B with attractant 137B. The computing device 150 may turn on and off a scent diffuser (i.e., dispensing machine 636B). The dispensing machine 636B may include a fan to direct the odor along a path in the direction of the at least one orifice or membrane 160B. The scent supply 637B may include an oil or liquid as the attractant 137B.

Figure 6B:
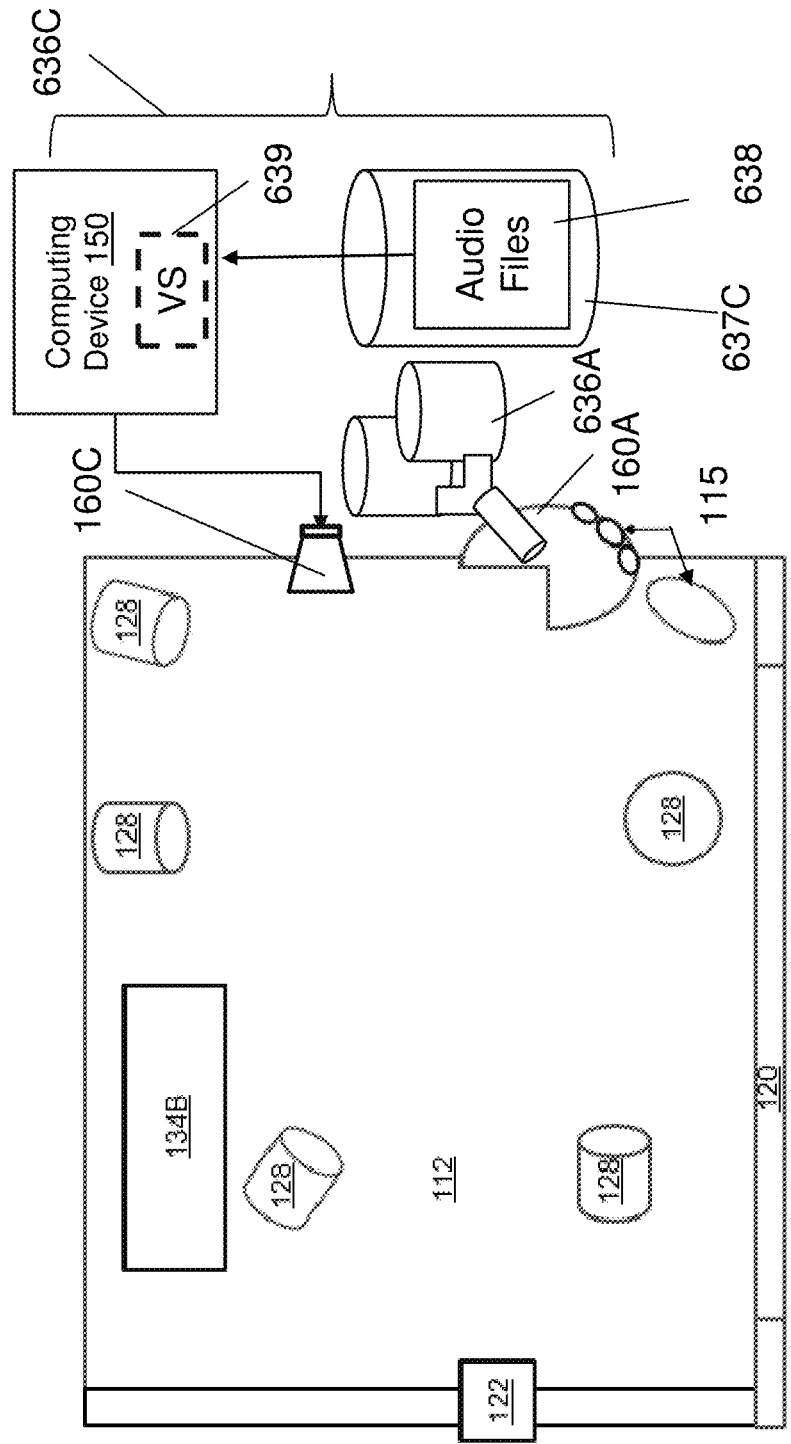
FIG. 6B illustrates a side view of the components of the analysis zone of two persuasion delivery devices, such as the bowl and speaker.

FIG. 6B illustrates a side view of the components of the analysis zone of two persuasion delivery devices, such as the bowl 160A and speaker 160C. By way of non-limiting example, the at least one persuasion delivery device 160 may include a speaker 160C that emits pet attracting sounds 137B (i.e., animal attractant 137) that are dispensed by the at least one dispensing machine 636C. The persuasion delivery device may be controlled by and/or include computing device 150. For example, the at least one dispensing machine 636C may include audio sound files 638 stored in memory 637C to produce audio sounds in the form of an animal attractant delivered to and output by the speaker 160C.

By way of non-limiting examples, the stored audio sounds (i.e., animal attractant 137) may include short sounds, verbal commands, pet name, and/or other sounds to which an animal may respond. In some embodiments, the at least one dispensing machine 636C may include a voice synthesizer (VS) 639 coupled to the speaker 160C. The computing device 150 may include a voice synthesizer 639, for example. A pet name received by the computing device 150 may be generated by the voice synthesizer 639 and output through the speaker 160C to attract the attention of the animal. The pet name may be entered via a user interface 134A, animal identification tag, or other input interface and communicated to the computing device 150. In some embodiments, an owner may enter the pets name and/or other commands that the animal may be trained to respond using a user interface 134A or other input interface, such as a personal communication device. The computing device 150 may control the voice synthesizer 639 to dispense such commands or pet name representative of the animal attractant 137 out through the speaker 160C and/or select from memory one or more stored audio sound files 637B representative of the animal attractant 137 that are dispensed out through the speaker 160C.

In some embodiments, the system 100 may include a combination of persuasion delivery devices 160. For example, the system 100 may include a bowl 160A to receive a dispensed treat from a dispensing machine and a speaker 160C that emits pet attracting sounds in proximity to the bowl or entrance to the analysis zone 112. In some embodiments, the system 100 may produce both sounds and an odor to attract the attention of the animal into the analysis zone 112. In some embodiments, the system 100 may produce sounds and/or an odor to attract the attention of the animal into the analysis zone 112 and dispense a treat into bowl 160A to keep the animal engaged and/or to attract the attention of the animal.

FIGS. 6A and 6B show several cameras 128 distributed above the animal and below the animal. The cameras 128 may be installed at locations in the side walls of the housing with a field of view directed toward the animal. The distributed cameras capture images of the animal from multiple directions including, but not limited to, the back, top front, sides, head, under the belly, etc.

In some embodiments, the kiosk housing is a non-stationary standalone unit that can be deployed in a mall corridor, in a retail store, or in proximity to other businesses or public service buildings.

The system 100 will be further described with the at least one persuasion delivery device 160 including a bowl 160A that receives a treat (i.e., animal attractant 137) dispensed by a dispensing machine 136, such as a treat dispensing machine. The system may include a walk-in analysis zone 112 with a bowl 160A within the walk-in analysis zone and sensors of the sensor suite 115 capable of sensing at least one biological parameter within the bowl, as the animal eats a treat in the bowl. The system includes a processor that receives the sensor data related to the at least one biological parameter in real-time so that a custom diet can be recommended or formulated on-site by a feed making machine.

The sensor suite 115 of the system 100 may include a scale 120 to detect the weight of the animal. The sensor suite 115 may include a tracking and identification (T&ID) sensor 122 to receive an identification (ID) signal that identifies the animal. By way of non-limiting example, the T&ID sensor 122 may be a radio frequency identification (RFID) sensor to identify the animal. For example, if an animal has an embedded chip having an RFID technology, the system 100 may detect an identification (ID) signal representative of an RFID signal to establish and track data files of the animal. The received RFID signal may be used to retrieve an animal's health record history previously stored in memory. An RFID tag can be located on the animal, in a collar worn by the animal or in a key chain of an owner, for instance. The system 100 may start a data capturing process in the analysis zone 112 using an input entered using a user interface 134A or by receipt of a sensed ID signal.

The T&ID sensor 122 may be a near field communication (NFC) device, short-range communication device or other wireless communication device to receive an ID signal from the animals ID tag, when the animal is in proximity to the T&ID sensor 122.

The sensor suite 115 may include one or more gas sensors 124 to detect the breath vapor of the animal. The sensor suite 115 may include one or more breathing sensors 126 to detect the breath of the animal. The sensor suite 115 may include one camera 127, the one camera 127 may be an infrared (IR) camera, thermal camera, red, green, blue (RGB) camera or a greyscale camera.

In some embodiments, the sensor suite 115 may include a computer/machine vision system 128 to analyze the animal's body. The computer/machine vision system 128 may include one or more other cameras such as, without limitation, at least one infrared (IR) camera 130 or thermal camera, at least one RGB camera 132, and/or at least one greyscale camera 131 to detect features of the animal, such as temperature, teeth, mouth, etc. The sensor suite 115 may include at least one microphone 133.

The system 100 may include at least one user interface 134A, 134B. For example, the system 100 may include a user interface 134B, such as a display device, in the analysis zone 112. The user interface may include a graphical user interface that allows an owner to enter information into the system. The system 100 may include a user interface 134A to allow the user/owner to interact with the system 100 to perform one or more of initiate the health analysis process, login, make a payment, order feed, and select a treat type.

The dispensing machine 136 may include with one or more treats (i.e., animal attractant). Treats can also be customized and produced on site or treats can be pre-made and contained within storage inside machine 136 (i.e., machine 636A of FIG. 6A or 6B). Any number of treats can be stored or created. Any number of treats can be dropped or dispensed into bowl 160A located within the analysis zone 112. This draws the animal into the analysis zone 112 and allows for momentary motion suppression or position alignment (head located in reference to body). The area in close proximity to the bowl 160A may include at least one gas sensor 124 and one or more of the cameras and/or the vision system 128. The treat dispensing machine may include a processor and/or controller in communication with a main processor located at the housing. Once the main processor receives a signal representative of the identification (ID) signal, the main processor may communicate a control signal to the processor and/or controller of the dispensing machine to cause the dispensing machine to dispense at least one treat (i.e., animal attractant), sound or smell.

The system 100 may manufacture treats. The treats may be manufactured internally to the system or remotely. The treats may be based on custom diets. The custom diets may be developed based upon all the information gathered by the system 100 and other industry resources, including veterinarians.

Based on the analysis, the user may optionally create feed for the animal based on the animal's health or age, for example, using a feed making machine 138.

The computing device 150 may receive health data from the scale 120, one or more gas sensors 124, one or more breathing sensors 126, and vision system 128 to display on at least one user interface 134A, 134B at least one of current health data, past health data and diagnostic data. The computing device 150 may include at least one processor to communicate and/or control at least one of the treat dispensing machine (i.e., machines 636A of FIGS. 6A and 6B) and the feed making machine.

Health or biological parameters and/or vitals captured during a session by the sensor suite 115 are described below.

In some embodiments, the system 100 may include a set of sensors to sense animal vital signs in the walk-in analysis zone 112. The system 100 may recommend animal feed nutrients based on at least one of breed of the animal, current body weight of the animal, current body shape, current body size, body composition, and/or vital signs. The recommended animal feed nutrients may also be based on age and/or sex of the animal.

The system 100 may recommend animal feed nutrients based on animal demographics such as breed, sex and age and one or more sensor data form the sensor suite 115. For example, the sensor data may determine one of weight, body shape, body health index and dimensions for use in recommending animal feed nutrients. The sensor data may include at least one biological parameter sensed by at least one sensor of the sensor suite 115.

The recommended animal feed nutrients may include a diet formulation.

Identification (ID)

After the ID associated with an animal is scanned, received or entered, the computing device 150 accesses a database to bring up an animal's history of stored health data, if available. This may prompt a single treat to drop, by the treat dispensing machines (i.e., machines 636A of FIGS. 6A and 6B), based on preset (stored) preferences/allergies/etc.

In other embodiments, the stored information may be based on animal breed, sex, age of the animal, etc. Accordingly, at the time of analysis, the treat selection may be selected based on one or more prestored data associated with knowledge of animal demographics that match the current animal. The animal feed nutrients may be based on age, sex, breed and/or at least one real-time biological parameter sensed by any one of the set of sensors of sensor suite 115.

Data Acquisition

The animal's, such as a dog, image and data acquisition takes place in the analysis zone 112. As the animal enters the analysis zone 112 and moves toward the treat in bowl 160A, the image and data acquisition begins. As the pet moves towards the treat, it is constantly being monitored and assessed.

The system 100 uses the animal's predisposition of attraction to an animal's treat to position the dog's face, nostrils, mouth and teeth directly in a field of capture of one or more sensors of the sensor suite 115. The aroma of the treat may provide guidance of the animal to the sensors of the sensor suite in the bowl. The predisposition of the animal is to naturally walk or move in the direction of the aroma in a stress free and autonomous configuration to find the treat. Likewise, the predisposition of the animal is to naturally walk or move in the direction of a sound or other smells in a stress free and autonomous configuration to find the animal attractant.

During data acquisition, the sensed data including one or more of the biological parameters, image data, weight and vital signs are logged into a client file 152. A processor of the system may log (or store) the real-time sensor data autonomously using the RFID sensed from the animal or other ID signal, for example. The system maintains the log of the sensed at least one biological parameter in memory coupled to the processor, as discussed in FIG. 18. The system 100 may monitor the logged sensed data to determine any trends or changes in a health condition.

Figure 16A:
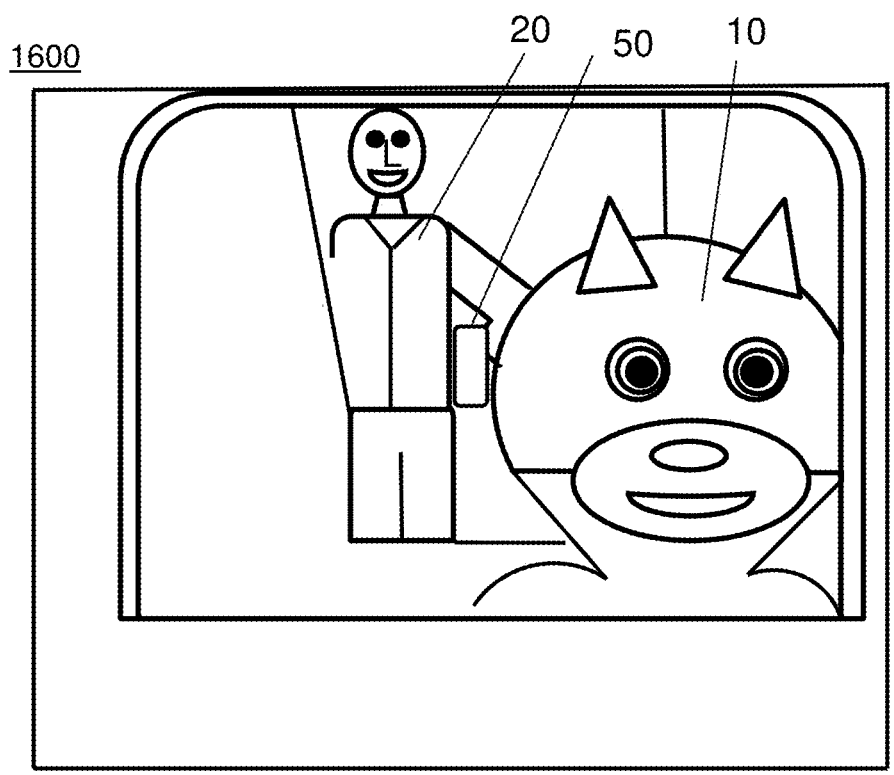
FIG. 16A shows an image of the animal in the analysis zone.
Figure 16B:
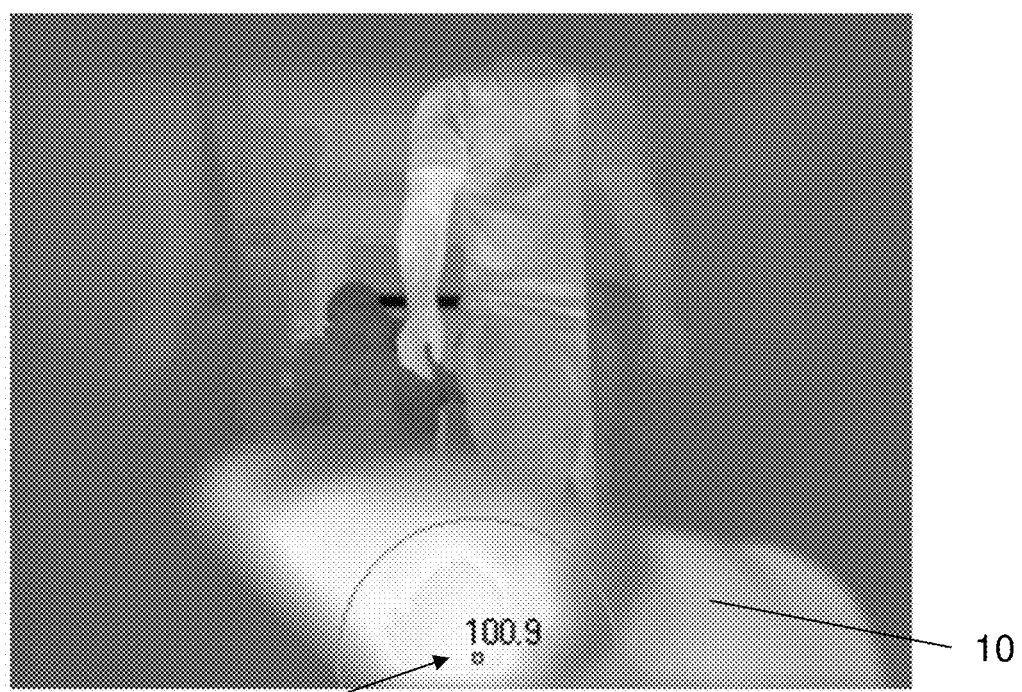
FIG. 16B shows a thermal image of the animal of FIG. 16A.

FIG. 16A shows an image 1600 of the animal in the analysis zone 112 captured by camera 127 (FIG. 1). FIG. 16B shows a thermal image 1650 of the animal of FIG. 16A captured by IR camera 130 (FIG. 1). FIG. 16A shows a view of an animal owner 20 using the system, where the animal owner 20 has a mobile device 50. The thermal image 1650 is shown with the temperature 1655 of the animal's body overlaid in the image. The mobile device 50 may be a mobile phone, internet-enabled mobile device, or a wireless body-worn mobile device. Each of the mobile devices may include wireless fidelity (WI-FI), BLUETOOTH technology or other near field communication protocol to detect, register and communicate with the computing device 150. The owner's mobile device 50 may receive the health data, analysis and a report of the analysis performed by the system 100, as will be described later. In some embodiments, the health data, analysis and report may also be sent to a cloud computing system which can then be accessed remotely by the owner using a laptop, personal computer, mobile device, or other computing device. In some embodiments, analysis of the sensor data and/or computer vision system data may be analyzed by a cloud computing system remote from at least one processor (i.e., computing device 150) associated with the housing.

Weight Analysis

The system 100 may autonomously determine the weight of the animal. For example, weight data is acquired during the entire session, as the animal walks on the scale 120 (FIG. 1) and toward the treat or other animal attractant. The weight data is processed by the computing device 150, for example, to improve the accuracy of the results and remove any discrepancies caused by movement of the pet.

Body Analysis

Figure 15A:
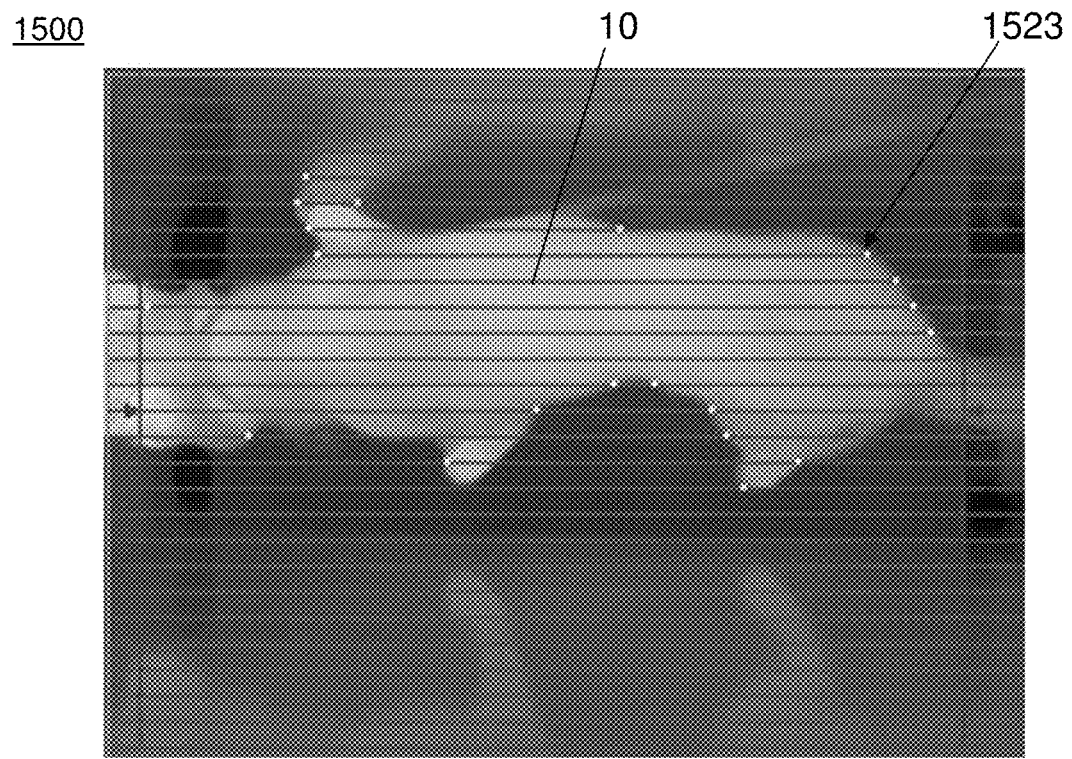
FIG. 15A shows a scanned image of the animal in the analysis zone.
Figure 15B:
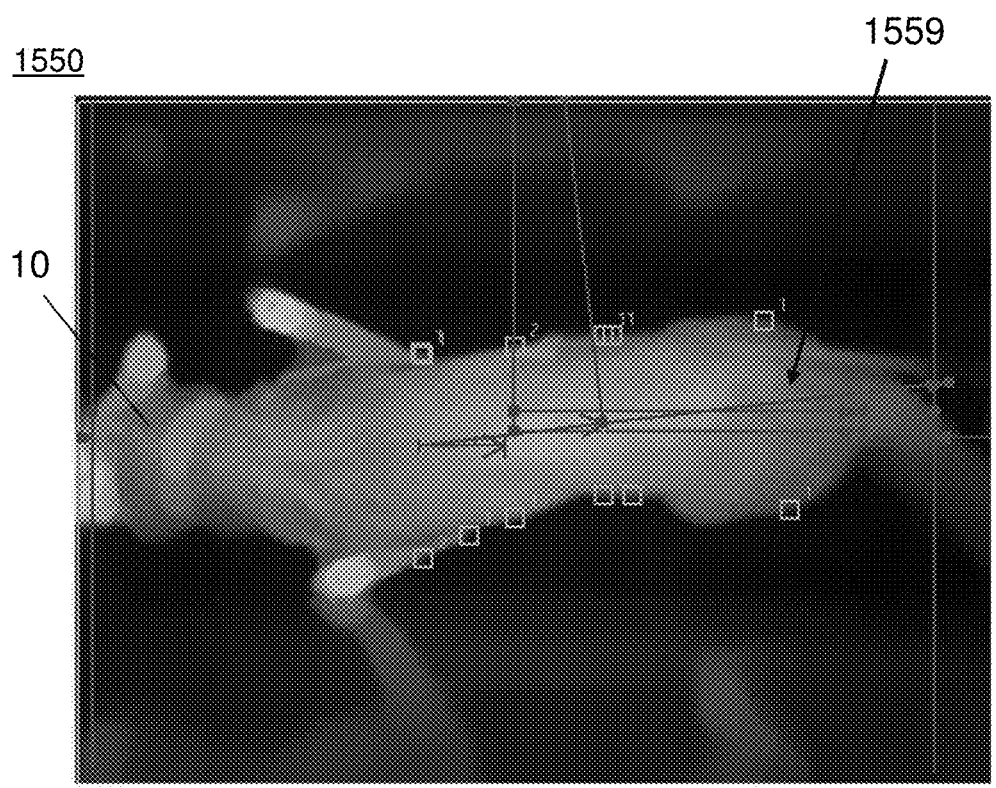
FIG. 15B shows sample analysis points used during analysis.

The system 100 may perform a body analysis. During the session, images are acquired by the vision system 128 from multiple cameras, and processed in real time. FIG. 15A shows a scanned image 1500 of the animal 10 in the analysis zone 112 with various data point 1523 noted in the image. FIG. 15B shows an image 1550 of sample analysis points overlaid on the body of the animal 10 used during analysis and measurement lines 1559 of example body dimensions.

The processing of the images, by the computing device 150, determines the dimensional characteristics of the animal's body to assist in the body and health assessment. Machine vision techniques may be supplemented with machine learning (ML) and artificial intelligence (AI) algorithms, for example. The cameras of the vision system 128 may employ IR camera(s) or thermal camera(s) to see through fur and determine actual body shape of the animal. The vision system 128 may determine the orientation of the animal. The body shape may be compared to breed database data for comparison and analysis. Many cameras can be used or a single camera with the aid of reflective surfaces funneling light to it. Standard RGB images are also obtained to track overall appearance and aging over time. The system 100 may use a fiducial marker collar as will be described in relation to FIGS. 19A-19C. The cameras may capture the LED lights or another fiducial marker on the collar to determine orientation of the animal and/or alignment.

Temperature Analysis

Figure 17:
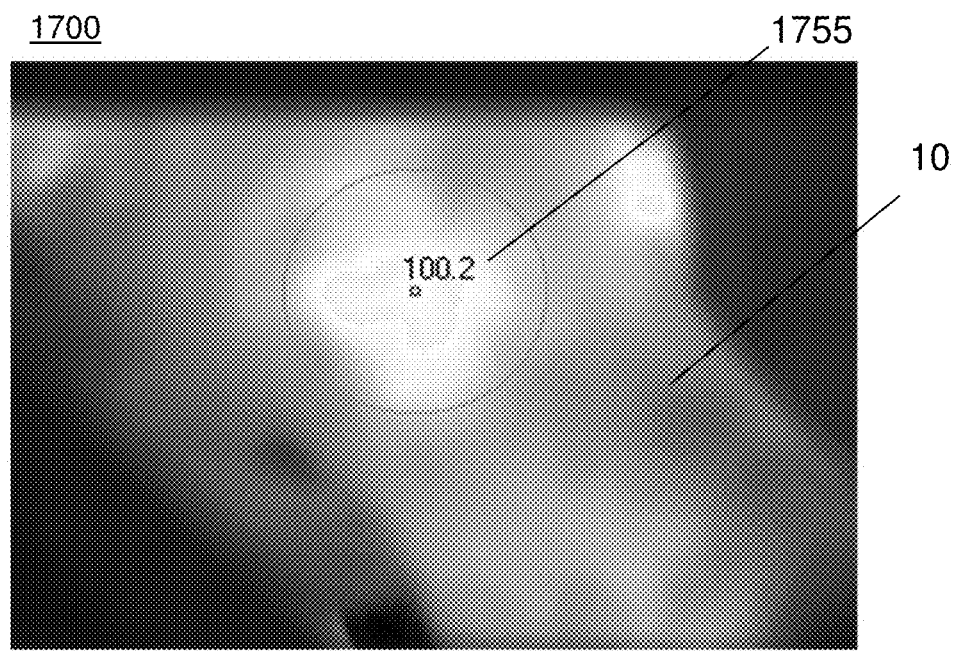
FIG. 17 shows a thermal image with temperature analysis indicators displayed.

The system 100 may perform a body temperature analysis of the animal 10. As the thermal images are acquired, the thermal images, such as from the IR camera(s) 130 are also processed in real time, by the computing device 150, to determine the body temperature of the animal based on IR image data derived from the animal's eyes. The system 100 may display the body temperature of the animal. In some embodiments, the temperature may be displayed over the eyes. FIG. 17 shows a thermal image 1700 with temperature analysis indicators 1755 displayed. This temperature may be of the eye of the animal 10.

In some embodiments, the analysis zone 112 in any of the housings described herein may include non-thermally reflective coatings placed throughout. This allows for "ghost" thermal images to not be produced or suppressed.

Information Analyzed and Food Production

Dental

The system 100 may perform an autonomous dental inspection through a hand-free examination in the analysis zone 112 by recording of eating by the animal 10 of the treat in the bowl 160A. Overall mouth color, individual tooth color, shape and placement can all be gathered and tracked over time, using image data captured by camera 127 and/or one or more cameras of the vision system 128.

The computing device 150 may use ML and AI algorithms to identify the mouth and the teeth of the animal to determine dental data. The mouth features may include gums and/or tongue, for example. The ML and AI algorithms may search for and detect each tooth in the images for teeth shape and color analysis. The system 100 may use convolutional neural networks (CNNs) to detect teeth. In some embodiments, the system 100 may determine plaque buildup on the teeth, such as based on a comparison of dental history data and other data, such as an expected tooth shape.

Breath

The system 100 may perform an autonomous breath analysis using data captured by breath sensor(s) 126. The breath sensor(s) 126 may sample gas or vapor emitted from the animal in proximity of the bowl 160A, for example. As the animal eats the treat dispensed in the bowl 160A, the animal's mouth enters the bowl, opens, and their tongue licks or their teeth chews the treat. By placing the breath sensor(s) 126 and cameras in proximity to the bowl or in the bowl, the system 100 can rely on the animal's natural instinct or predisposition to eat a treat without causing stress.

The breath sensor(s) 126 may include gas analyzer like PIR/NDIR, laser diode spectroscopy, electrochemical, chromatography, etc. The computing device 150 may receive the breath sensor data and compare the breath data to at least one of past measurements and to those in databases to determine other health related phenomenon happening to animal. Other factors such as temperature, humidity and pressure from breath can be gathered and used for comparisons or direct diagnosis (NDIR-nondispersive infrared) (PIR-passive infrared).

Figure 4A:
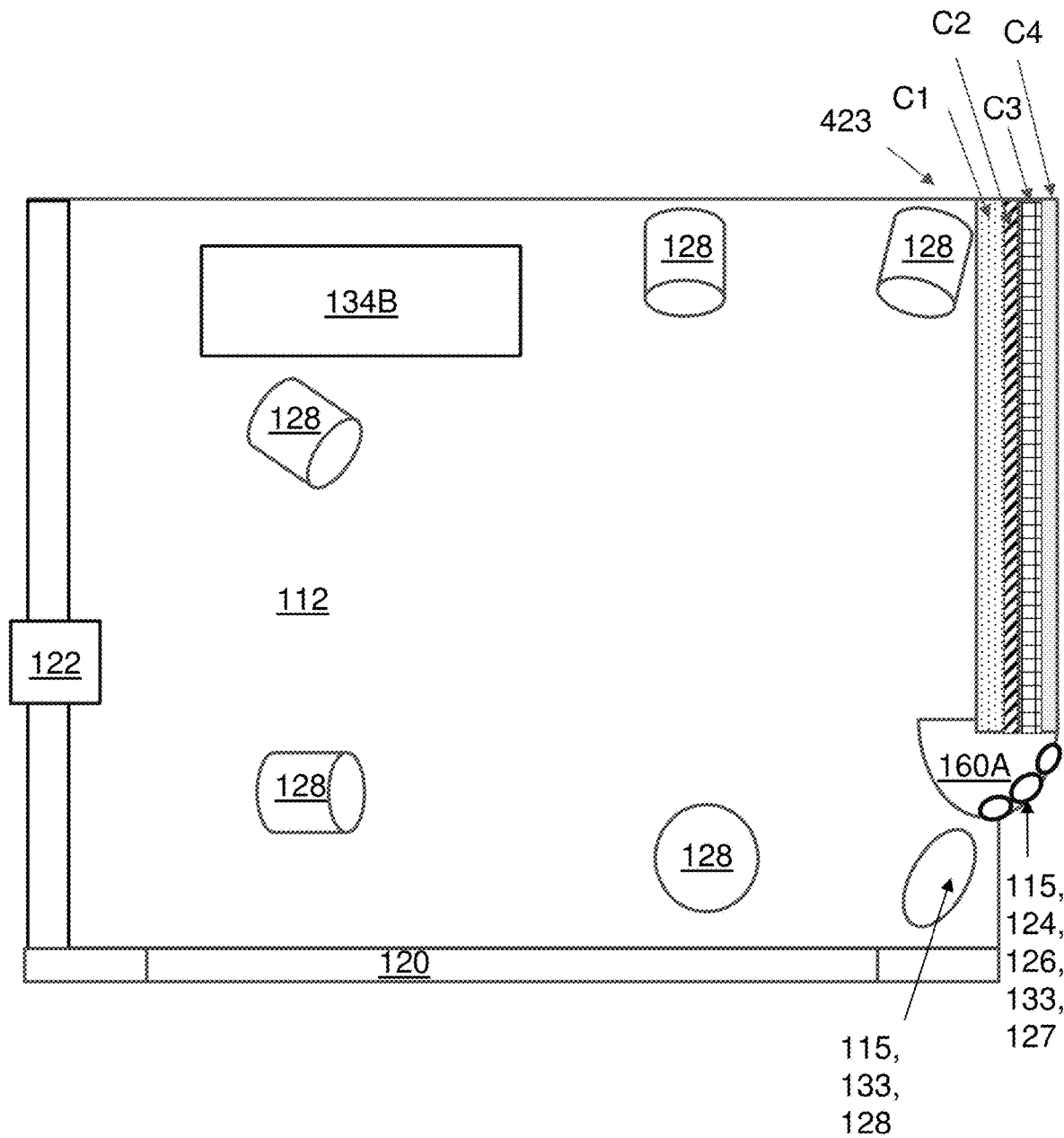
FIG. 4A shows a side view of the components of the analysis zone of the system for non-invasive animal health sensing and analysis.
Figure 4B:
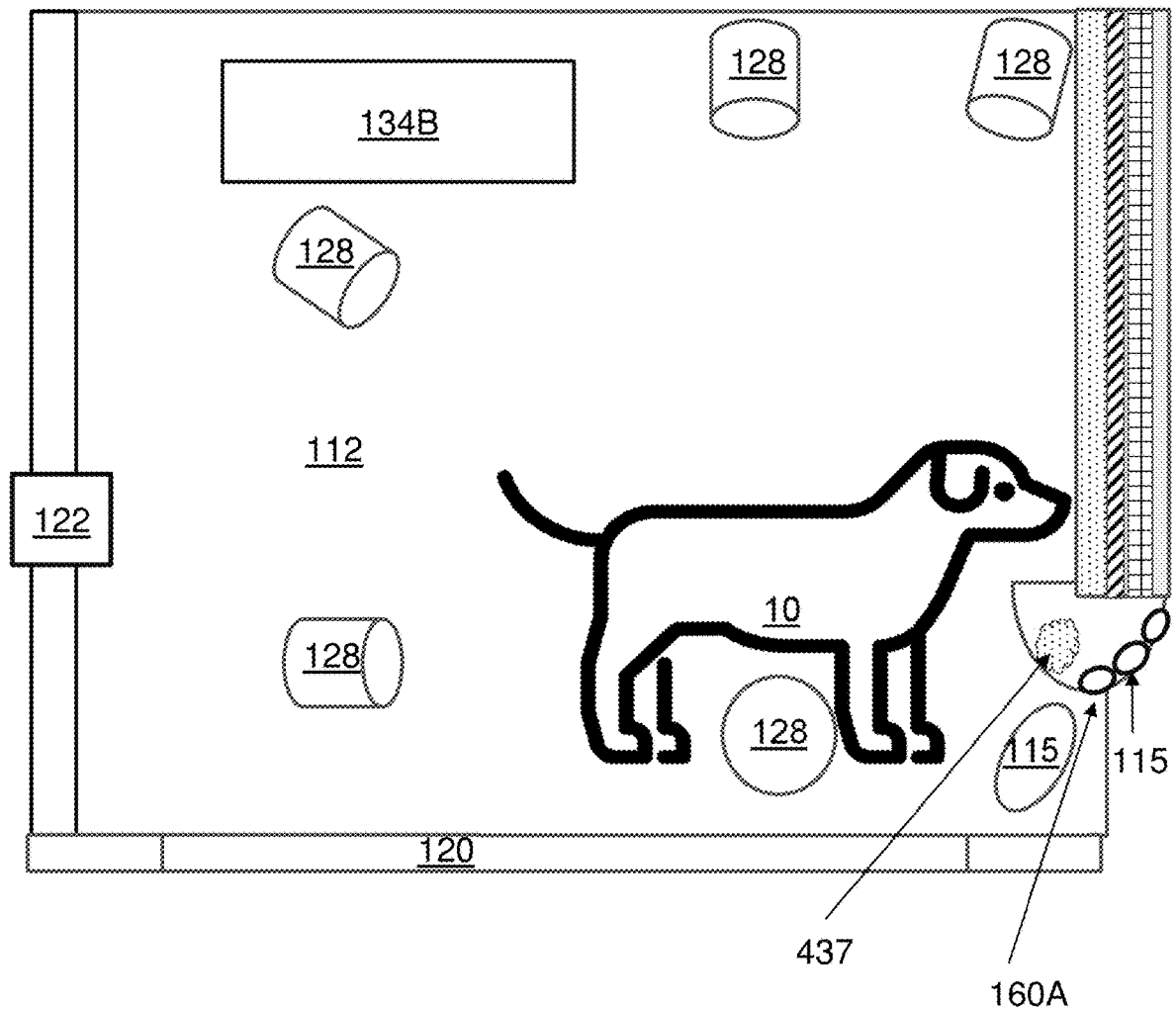
FIG. 4B shows a side view of the components of the analysis zone of FIG. 4A with an animal attractant being dispensed in the analysis zone.

Although FIGS. 4A and 4B show the breath sensor(s) 126 in the bowl, the breath sensor(s) 126 may be placed on the back wall of the housing, just above the top rim of the bowl, for example. The breath sensor(s) 126 may be positioned in proximity to other persuasion delivery devices 160.

Heartbeat and Breathing Detection

The system 100 may perform heartbeat and/or breathing detection. Labored breathing leads to health issues, as well as irregular heartbeat. The system 100 may detect the breathing of the animal with microphone(s) 133 in the analysis zone 112 or using a device with microphone 133. At least one microphone 133 may be placed in proximity to the bowl 160A or other persuasion delivery devices 160. The captured breathing data may be analyzed for any inconsistencies or anomalies of breath sounds using the computing device 150.

Similarly, the heartbeat may be detected by the system 100. Filters may be used to acquire the appropriate sounds from the microphone(s) 133. For example, microphone on a handheld device or other device may be used by placing the microphone near the animal's heart to analyze the recorded heartbeat, by the computing device 150 through software, such as described at www.ncbi.nlm.nih.gov/pmc/articles/PMC5853766, incorporated herein by reference.

For example, at least one microphone may be placed in the front and lower portion of the bowl 160A to pre-position the microphone close to the animal's chest when the animal is eating the treat.

The system 100 captures sensor data by the sensor suite 115 for diagnostic analysis of the current health of the animal and recommend specialized treats or food for the owner 20 to treat a detected health condition of the animal, related to weight, breath, teeth, etc. The food production, by the feed making machine 138 can take place inside the housing 110, 210, or 310 itself or remotely. The nutritional constituents of the food or treat are formulated based on the sensor data and formulas developed from veterinarian professionals and based on parameters such as breed, current body weight and shape, other data gathered by the system 100.

The main processor (i.e., computing device 150) may receive the sensor data and/or vision system data. The main processor may communicate this data to a cloud computing system or perform the analysis at the housing. In some embodiments, the cloud computing system may communicate recommendation based on the analysis which may then be sent to at least one of the main processor, the owner's mobile communications device and stored remotely that is accessible by the owner via a website. The recommendations by the cloud computing system may be communicated to the main processor. The main processor may then control a feed making machine 138 at the location of the housing. Alternately, or in addition to, the owner may order feed through a website without returning to the housing. For example, the owner and animal may be able to order feed through a website for 3-12 months without returning to the housing for subsequent sensing by the sensor suite 115.

In some embodiments, the system 100 may include at least one processor such as the main processor to perform analysis and identifying recommendations of a diet formulation. In some embodiments, the system may include at least one processor such as a combination of the main processor and at least one processor of the cloud computing system to perform analysis and identifying recommendations of a diet formulation.

Food Production Methods

Food production can take place utilizing traditional approaches, however, separating ingredients into individual storage containers allows for more shelf stable ingredients to last longer compared to when they are mixed with perishable/short term ingredients. Therefore, a more advantageous approach is to either press the treat/food into tablets or additively manufacture the items in-situ. The ingredients may need to use a common binder to facilitate holding shape of the mold or additively built structure. The system 100 may use human food grade cellulose for binding purposes. The binding process may include the application of heat or other methods. It should be understood, as used herein, food and treat production refer to the same thing.

The food production may include combining existing food tablets or pellets that include pre-known ingredients. The system 100 may provide a supply of multiple food tablets or pellets onsite in bins at the kiosk housing, for example. The system 100 may determine the amount of selected food tablets or pellets to be combined by weight to deliver the recommended ingredients. The system 100 may dispense an amount of at least one type of food tablet autonomously into a container for purchase by the owner. In some embodiments, bins of food tablets or pellets may be selected manually by a user to dispense recommended amounts of the different food tablets or pellets into the container.

Figure 5:
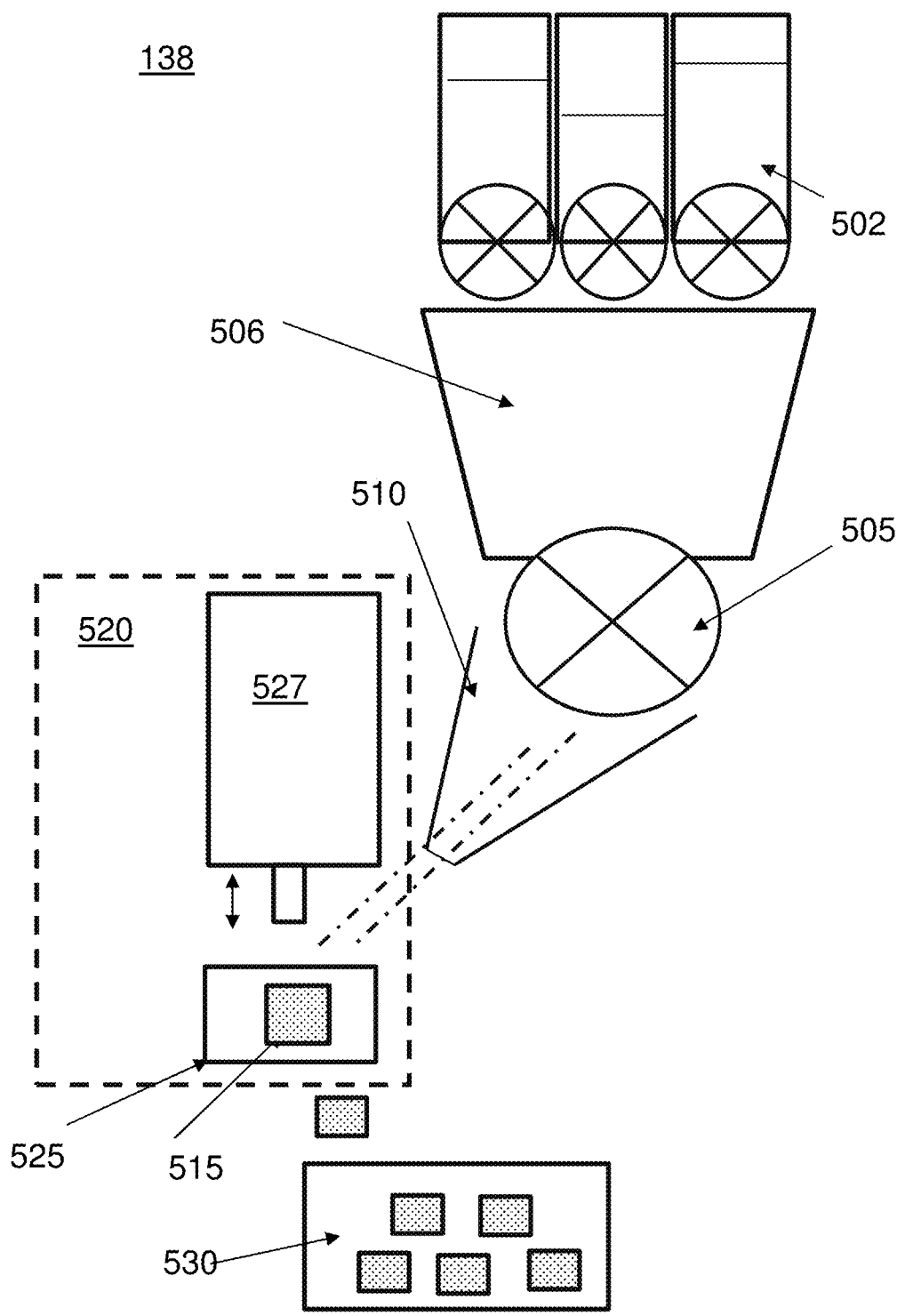
FIG. 5 shows a feed making machine.

FIG. 5 shows a feed making machine 138. The feed making machine 138 may include ingredient storage chambers 502 to store a supply of ingredients. Each chamber 502 may include an ingredient that can be selectively dispensed to make feed. The ingredients from the one or more chambers 502 are fed into a mixer 505. The mixer may include a funnel or hopper 506 from the chambers 502 to the mixer 505. The mixed ingredients may be fed into a feed system 510 which outputs to a table press device 520. The press device 520 may include a mechanism 525 to support an amount of the mixed feed 515 at a location to be pressed into a one or more feed pellets or tablets, for example, by a pressing machine 527. The press device 520 controls the pressing operation of the pressing machine 527. After the pressing action is complete to make a pellet or tablet, for example, the press device 520 dispenses the pressed pellet or tablet into a reservoir 530. The reservoir may be a bag or storage container for holding the dispensed pellet or tablet. The container may be given to the owner/user.

The press device is a feed pellet maker. In some embodiments, the housing may include a food dispensing port 281 (FIG. 2) to dispense pellets or tablets or placement into a bag or storage container or packaged pellets or tablets already in the reservoir 530.

Weight Tracking Reference

The system 100 may use a weight tracking reference based on images of the animal. An example weight tracking reference chart based on the body condition system was developed at the Nestle Purina Pet Care Center. This is a non-limiting example of how the animal is compared to determine body shape based on side and top views of the animal's body. The information/data available on such charts may vary by breed which can be either manually input (using the questionnaire) or extrapolated by the computer based on the database of existing information. Using machine learning, the software can determine the best fit for the outline that it calculates and determine the breed or best match to the breed for weight comparison. The best fit analysis may include size and shape of the animal, animal coat color and coat hair type, ear features, eye features and/or facial features of the animal.

The imaging data may determine when an animal is underweight, ideal, overweight, obese and severely obese. For example, when the animal is underweight, ribs and hip bones are visible from the top and sides of the animal. When the animal is an ideal weight, the ribs can be seen and felt, the belly tucks up when viewed from the side. When the animal is overweight, the ribs are covered with excess fat, the belly tucks up slightly when viewed from the side. The imaging data may be used to determine various overweight, obese and severely obese parameter, based on whether the waist of the animal is visible, the size of the belly relative to the chest, and the presence of fat deposits on the base of the tail and/or back and other visual indicators. The imaging data may determine the body composition such as fat deposits. The body composition may also be a function of the weight of the animal relative to an ideal weight base on breed, shape and size.

An obese animal may be 15% to 30% over the ideal weight. Severely obese may have a weight that is over 45% of the ideal weight. Another range of an obese animal have a weight that is between 30% and 45% of the ideal weight. The images may find other dimensions related to weight metrics based on the waist, belly, chest, and locations of fat deposits, for example.

Housing

Figure 2:
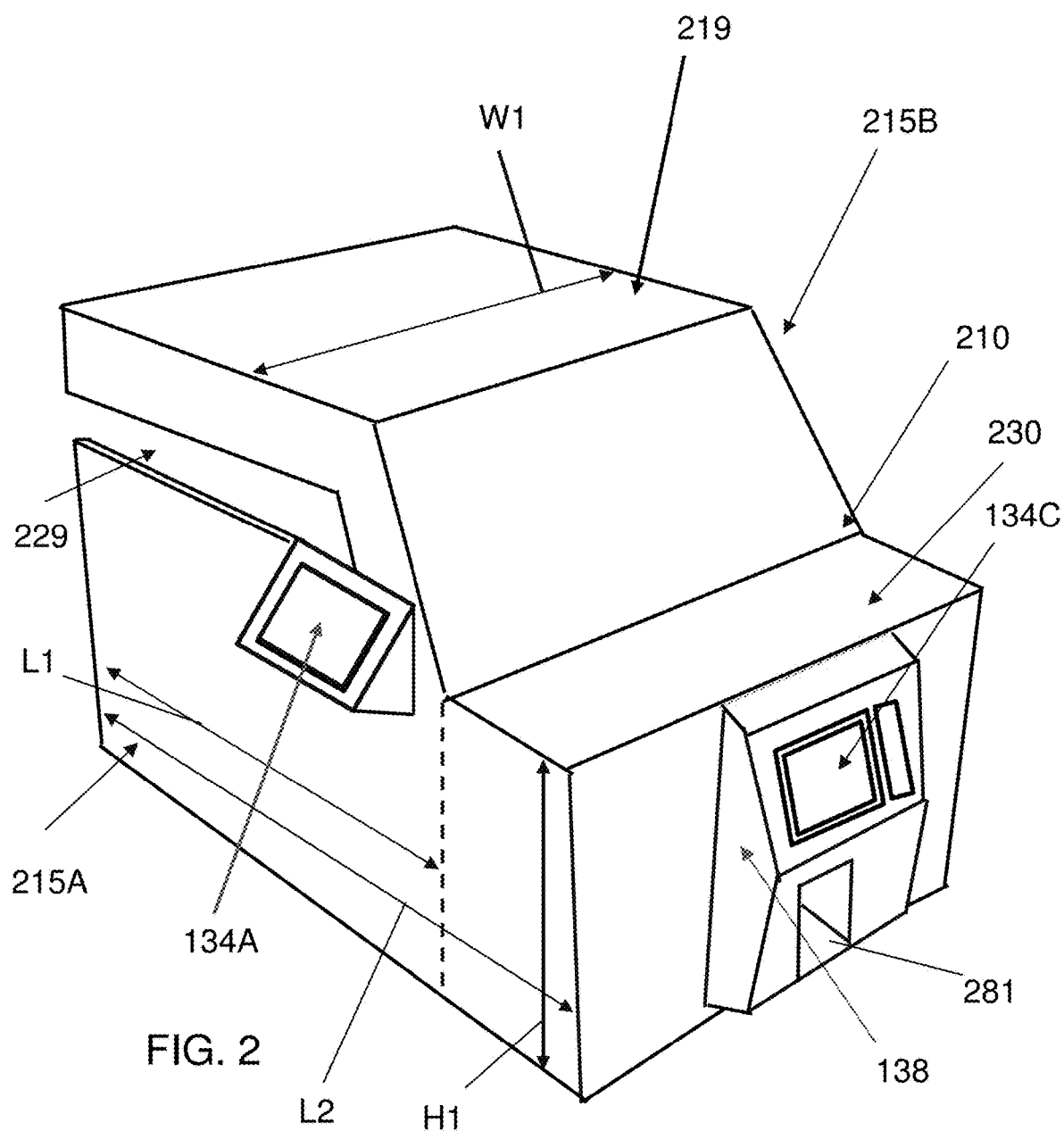
FIG. 2 shows a perspective view of a closed-top housing of the system of FIG. 1.

FIG. 2 shows a perspective view of a closed-top housing 210 of the system 100 of FIG. 1. The housing 210 includes two side walls 215A and 215B and a closed-top 219. One of the two side walls (i.e., side wall 215A) includes a leash slot 229. In operation, the owner may walk the animal into the analysis zone while the animal remains on a leash. The interior surfaces of the walls of housing 210 may include non-thermally reflective coatings. The housing 210 may include one or more viewing locations, each viewing location may include a display device or user interface. The computing device may cause the display device in the viewing location or on an owner's mobile device to display information representative of the sensed data.

The closed-top 219 provides a support surface for mounting imaging devices or cameras of the computer/machine vision system 128. The housing 210 provides surface support for the user interface 134A which is shown on the exterior side of the side wall 215A.

Figure 4C:
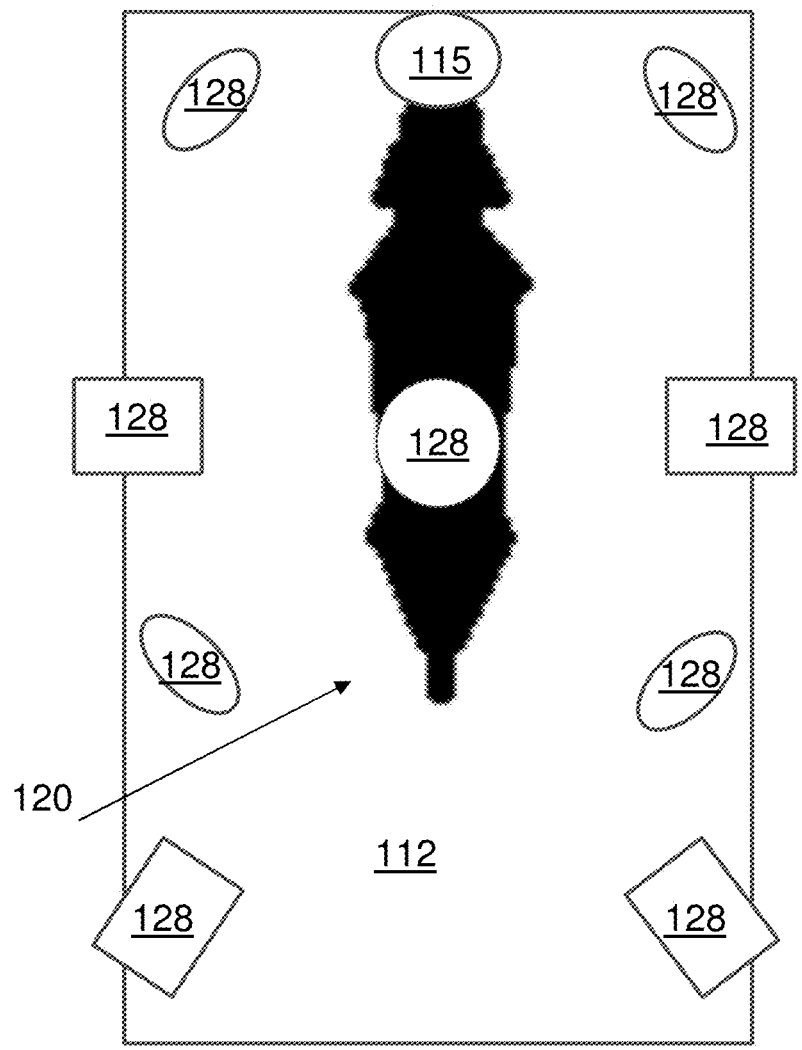
FIG. 4C shows a top view of the components of the analysis zone of FIG. 4B with the animal in the analysis zone.

The housing 210 includes a cavity or chamber 230 for housing the treats and at least one dispensing chute 423, as described in FIGS. 4A and 4B. FIGS. 4A-4C also show an interior of the housing and the analysis zone 112. The chutes C1-C4 may each store a different treat type.

The housing may include a door for access to add materials to the machines 136 and/or 138. The feed making machine 138 may include a user interface 134C to order feed and pay for the feed.

The housing dimension may include a height H1 of 2.1 meters. The total length L2 may be 3.33 meters. The length of line L1 is approximately 2.58 m. The height H1 may be approximately 1.3 meters. The width W1 is approximately 2 meters.

Figure 3A:
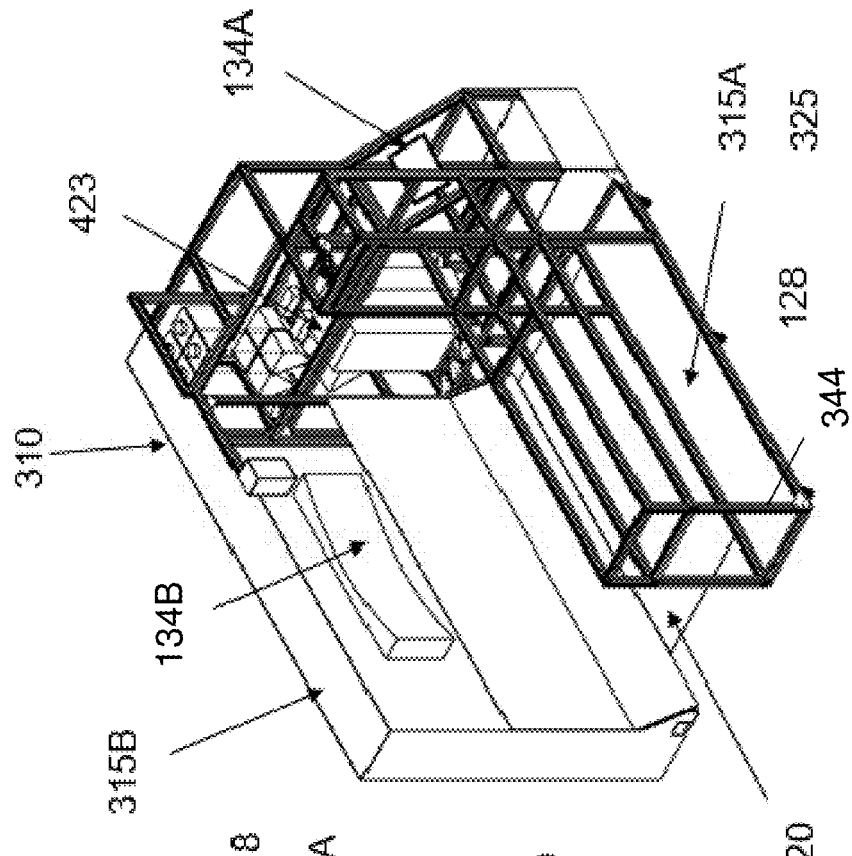
FIGS. 3A-3D show a perspective, top, front and side views of an open-top housing of the system of FIG. 1.
Figure 3B:
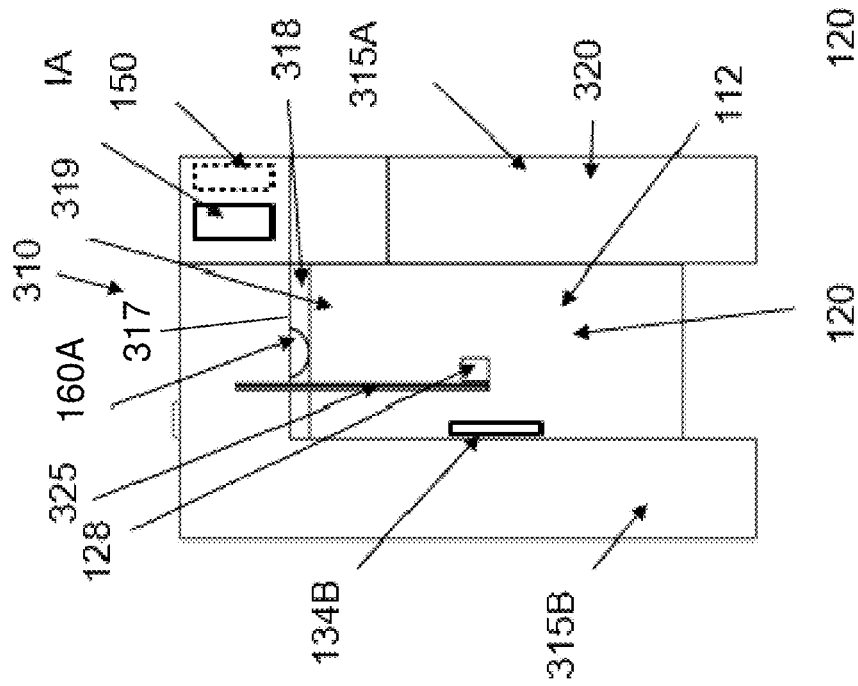
Figure 3D:
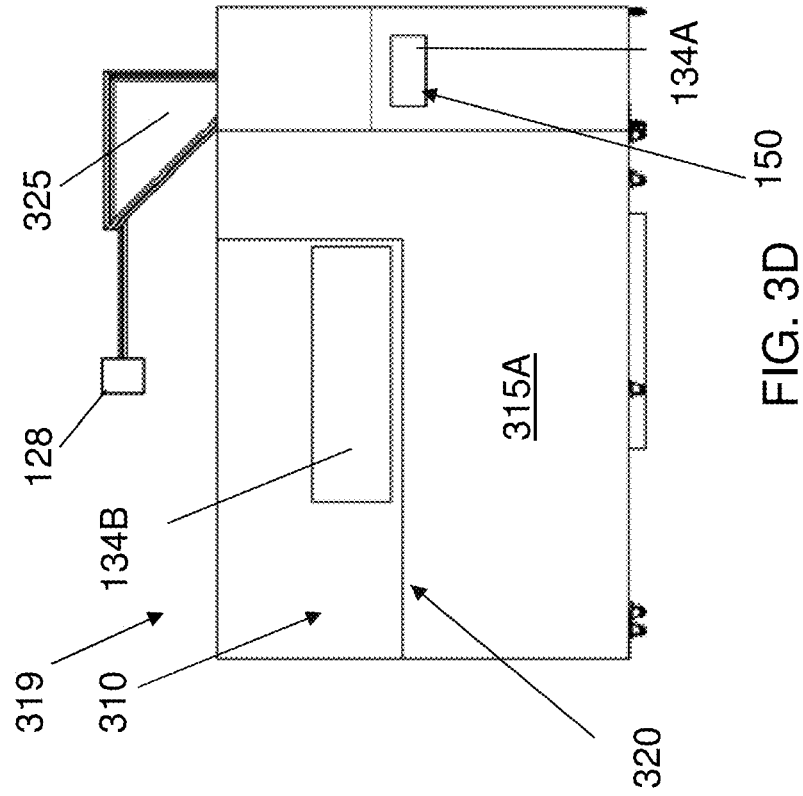
Figure 3C:
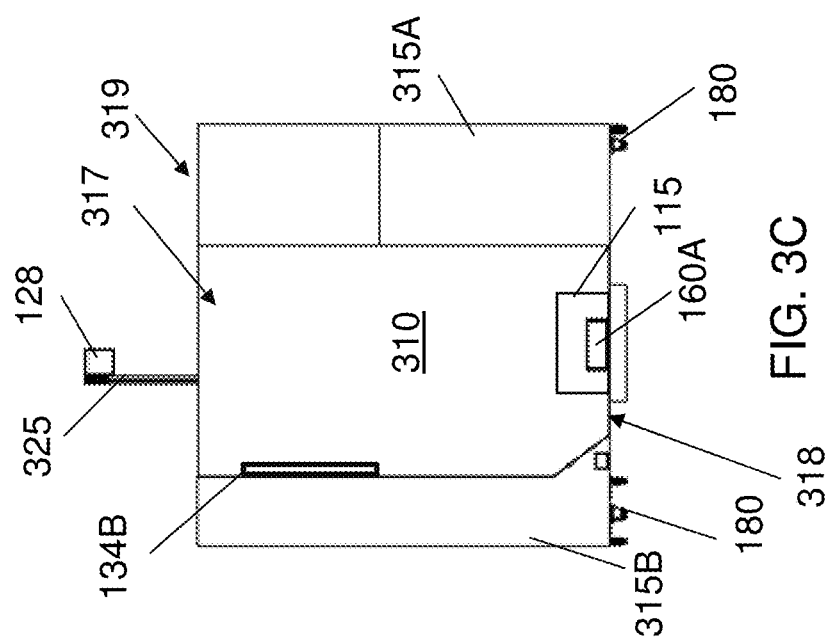

FIGS. 3A-3D show a perspective, top, front and side views of an open-top housing 310 (i.e., housing 110) of the system 100 of FIG. 1. The housing 310 includes two side walls 315A and 315B and an open-top 319. One of the two side walls (i.e., side wall 315A) includes a leash ledge 320. In one example of operation, the user/owner walks the animal into the analysis zone 112 while the animal remains on a leash, if a leash is available. The owner remains outside of the housing while the animal moves toward the treat by the predisposition of the animal to seek out a treat or other animal attractant. The housing 310 provides a surface support for the user interface 134B to be mounted or affixed, which is shown on the interior side of the side wall 315B. Therefore, the display screen of the user interface 134B can be seen by the owner while also monitoring the activities of the animal in the analysis zoner 112. In the embodiment of FIGS. 3A-3D, one of the two side walls is lower than the other to provide the leash ledge 320. In FIG. 3A, portions of the walls have been removed to show underlying framing elements 344.

The animal may be guided into the analysis zone 112 with or without the use of a leash or without the need for activation of the at least one persuasion delivery device 160 (FIG. 1). However, in some instances, an animal may have a leash available at the kiosk housing. Accordingly, a persuasion to an animal may include a force exerted on the animal using a leash where the force persuades the animal into the walk-in the analysis zone for conducting an examination session. In some embodiments, the leash is a persuasion delivery device, which may be used alone or in combination with any of the other persuasion delivery devices mounted in the analysis zone described herein.

A support structure 325 is provided for mounting imaging devices or cameras of the computer/machine vision system 128 overhead. The housing 310 may include a back wall 317 from which the bowl 160A may be mounted or placed on the floor 318. The floor 318 may be under the bowl 160A or may be part of or integrated with the surface of the scale 120. In some embodiments, the housing may be supported by wheels 180 or legs.

Referring now to the analysis zone 112, FIG. 4A shows a side view of the components of the analysis zone 112 of the system 100 for non-invasive animal health sensing and analysis. FIG. 4B shows side view of the components of the analysis zone 112 of FIG. 4A with an animal attractant 137 being dispensed to bowl 160A in the analysis zone. FIG. 4C shows a top view of the components of the analysis zone 112 of FIG. 4B with the animal in the analysis zone 112.

FIG. 4A shows the chutes C1-C4 for dispensing different animal attractants (i.e., treats). The system 100 may automatically dispense one or more treats 437 from one or more chutes to naturally attract the animal toward bowl 160A. The bowl 160A may support one or more sensors of the sensor suite 115. For example, the sensors may include gas sensors 124, breathing sensors 126, camera 127 and/or cameras of vision system 128. The sensors of the sensor suite 115 may include microphone(s) 133. In some embodiments, personnel managing the system may dispense a treat manually based on at least one of the animal breed, animal age, sex, and other information. The chutes may have an opening to allow the personnel to place in a chute a treats 437.

FIG. 4B shows the dog approaching the bowl 160A to eat the treat 437. As the dog walks along the surface of the scale 120, the weight of the animal 10 is captured. The sensors of the sensor suite 115 in the analysis zone 112 is captured.

The bowl 160A has a concaved area or bowl cavity to receive the treats. This concaved area provides a bowl area within the analysis zone. The bowl area may include some of the sensors of the set of sensors from suite 115. For example, the bowl area comprises at least one of: a microphone within the concaved area bound by the bowl to capture breathing data to determine the breathing rate; a microphone in proximity or outside of the bowl area to capture a heartbeat of the animal; a gas analyzer within the concaved area bound by the bowl to sense the breath vapor; and an imaging device within the concaved area bound by the bowl to capture images associated with the dental condition of the animal.

FIGS. 4A-4C show several cameras 128 distributed above the animal and below the animal. The cameras 128 may be installed at locations in the side walls of the housing with a field of view directed toward the animal. The distributed cameras capture images of the animal from multiple directions including, but not limited to the back, top front, sides, head, under the belly, etc.

Figure 10A:
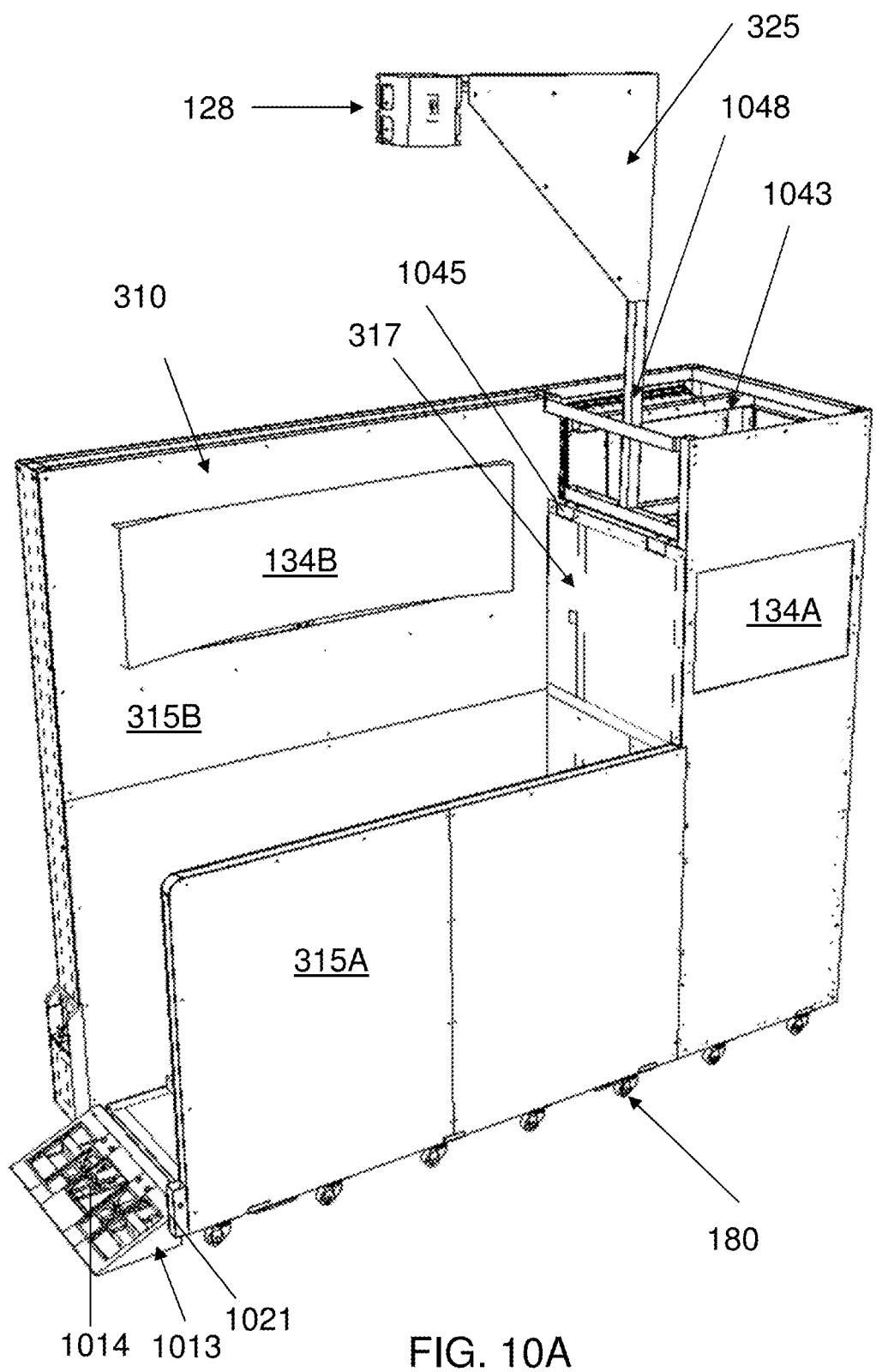
FIG. 10A shows a side perspective view of the housing and camera support structure in an upright position and ramp in an unfolded position.
Figure 10B:
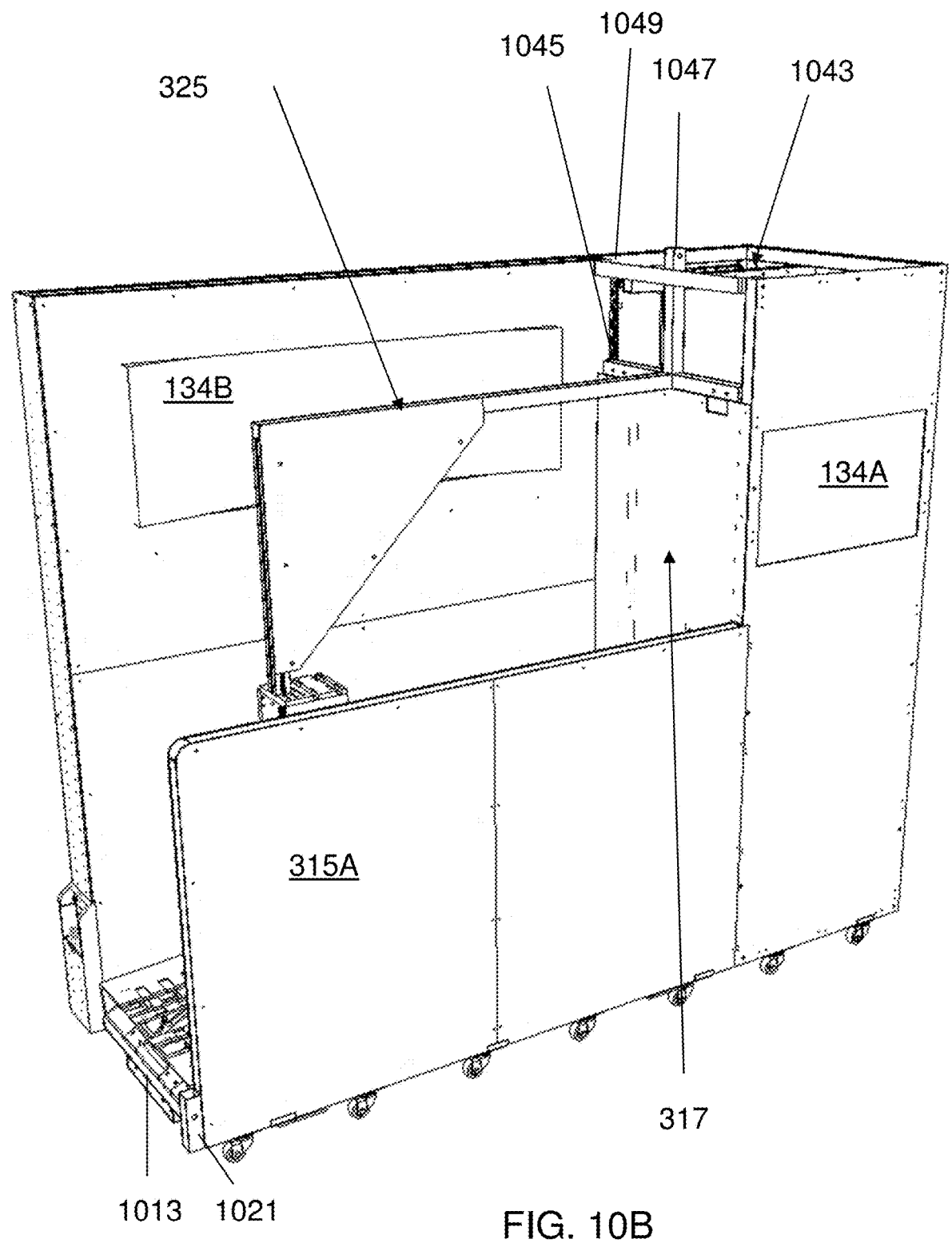
FIG. 10B illustrates a side perspective view of the housing and the camera support structure in a stowed position and the ramp in a folded position.
Figure 10C:
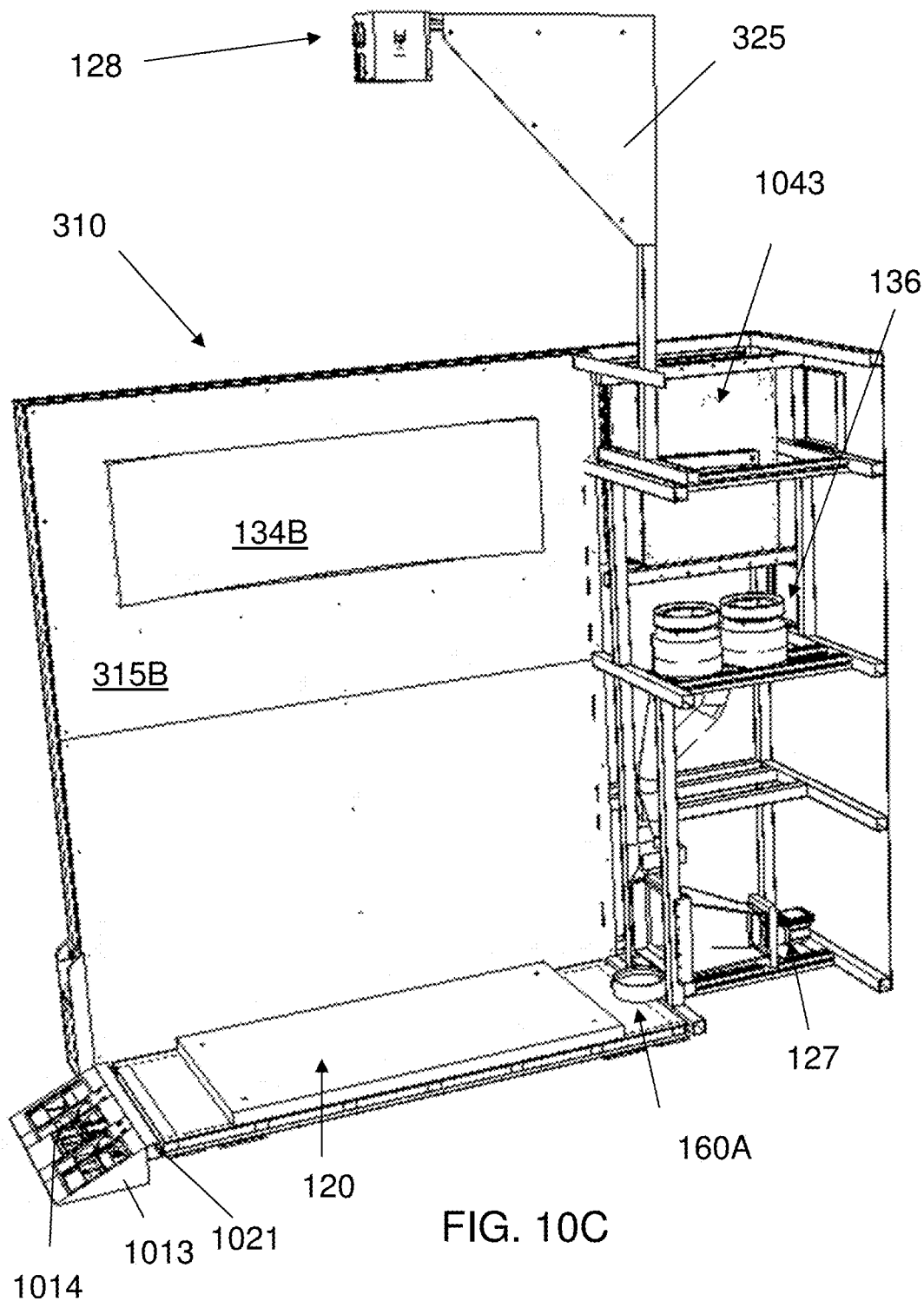
FIG. 10C shows a side perspective view of the housing with side wall removed and the camera support structure in the upright position of FIG. 10A.

FIG. 10A shows a side perspective view of the housing 310 (FIGS. 3A-3D) and camera support structure 325 in an upright position and a ramp 1013 in an unfolded position. The ramp 1013 rotates about pivot member 1021 and includes a sensor 1014. FIG. 10B illustrates a side perspective view of the housing 310 and the camera support structure 325 in a stowed position with the ramp 1013 in a folded position. FIG. 10C shows a side perspective view of the housing with side wall 315A removed and the camera support structure 325 in the upright position of FIG. 10A. Referring to FIGS. 10A-10C, the housing 310 includes a storage compartment 1043 behind back wall 317. The camera 127 and dispensing machine 136 are stored behind back wall 317 in the storage compartment 1043 and will be described in more detail in relation to FIG. 11. The storage compartment 1043 may include shelves to mount portions of the dispensing machine 136 and/or food making machine 138 (FIG. 5).

The camera support structure 325 may include a mast 1048 which is hingedly coupled to the housing 310 about hinge element 1045. In some embodiments, the mast 1048 is hingedly coupled to a portion of the back wall 317. The camera support structure 325 may include a cross support 1047 (FIG. 10B) perpendicularly coupled to an end of the mast. The housing includes a stop bar 1049 to stop the rotation of the mast in the stowed position, as shown in FIG. 10B. In the stowed position, the mast and the cameras of the vision system 128 are below the height of side wall 315B.

Figure 11:
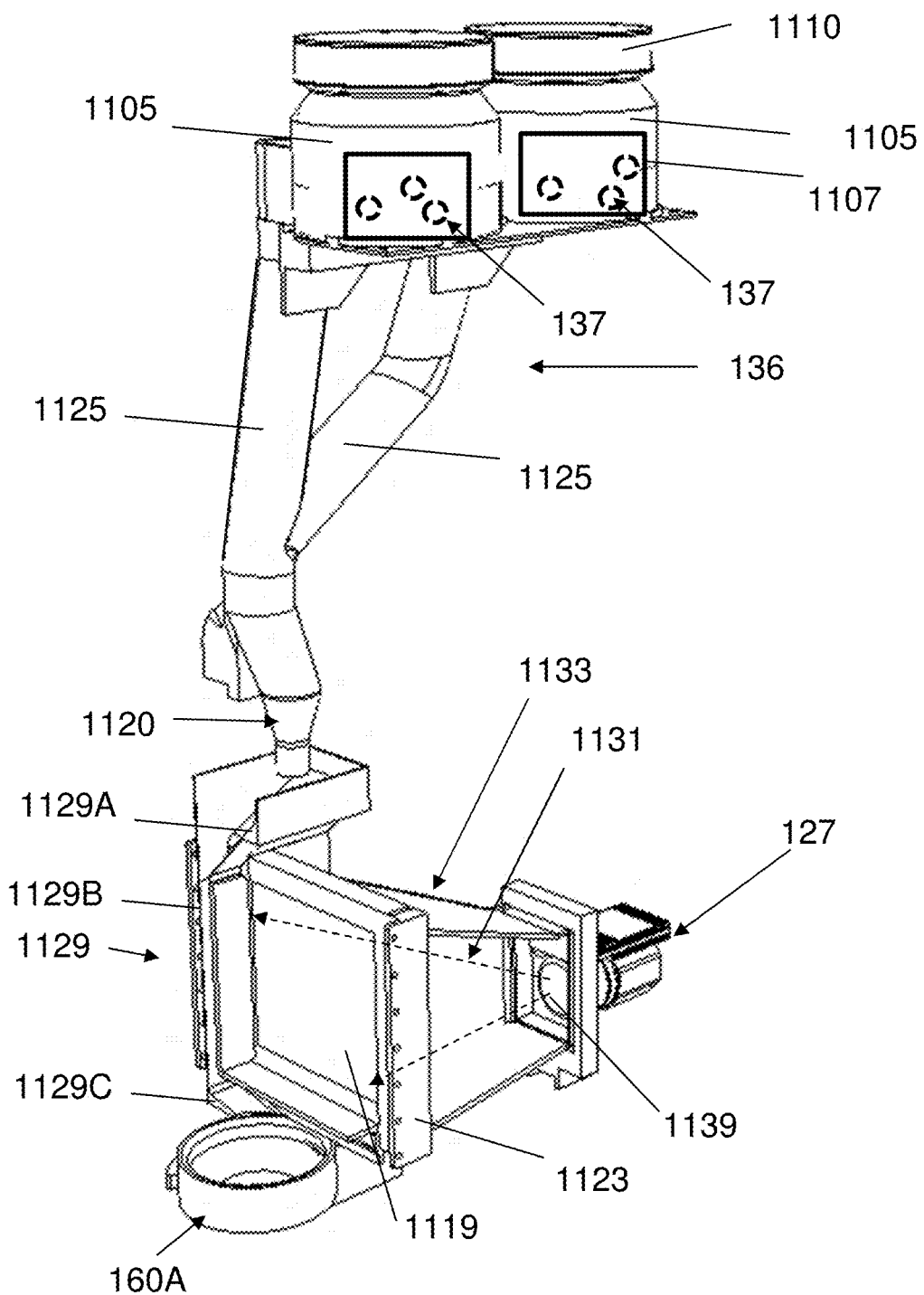
FIG. 11 illustrates a persuasion delivery device, dispensing machine and camera according to an embodiment.

FIG. 11 illustrates a persuasion delivery device 160C, dispensing machine 136, and camera 127 according to an embodiment. The persuasion delivery device 160C is a bowl to receive animal attractants 137 dispensed by the dispensing machine 136.

The dispensing machine 136 is mounted and/or stored at a location behind the back wall 317 of the housing in a storage area. The camera 127 is also mounted or positioned at a location behind the back wall 317. The system may include a transparent surface 1119 or window mounted to a frame 1123. The frame 1123 is configured to be mounted to the back wall 317 at a location in proximity to the bowl or other persuasion delivery device. The system may include an imaging path 1131, denoted in dashed lines, that includes a camera shroud 1133 that extends from the front end of the camera 127 to the frame 1123, so that the camera lens 1139 is recessed behind the transparent surface 1119 or window. The lens 1139 has a field of view from the camera 127 along the imaging path in the shroud 1133 and out through the transparent surface 1119.

Since animals may drool, lick surfaces or bite surfaces, the transparent surface 1119 may be cleaned and sterilized, as needed.

In the illustration, the camera 127 is a face camera to capture images of an animal's face. Specifically, the camera 127 may capture the eyes, nose, face, mouth, tongue and teeth, for example. The camera 127 may capture other ailments or growths around the face of the animal.

The dispensing machine 136 may include one or more treat holding chambers 1105 and a cover 1110 above the chamber 1105 closing the chambers. The treat holding chambers serve as animal attractant storage devices. The holding chambers 1105 are coupled to dispensing chutes 1125. Each chamber may have a correspondingly different chute 1125. In some embodiments, the holding chambers 1105 may include a transparent window 1107 to allow personnel to determine the amount of animal attractant remaining in the chambers. The dispensing machine 136 may include a hopper or funnel 1120 leading to a second dispensing chute 1129. The second dispensing chute 1129 includes a first upper sloped chute section 1129A, a second vertical chute section 1129B and a third sloped chute section 1129C that feeds into the bowl 160A. The first upper sloped chute section 1129B feeds into the second vertical chute section 1129B which may be positioned along a side of the frame 1123. The second vertical chute section 1129B feeds into the third sloped chute section 1129C.

Figure 12A:
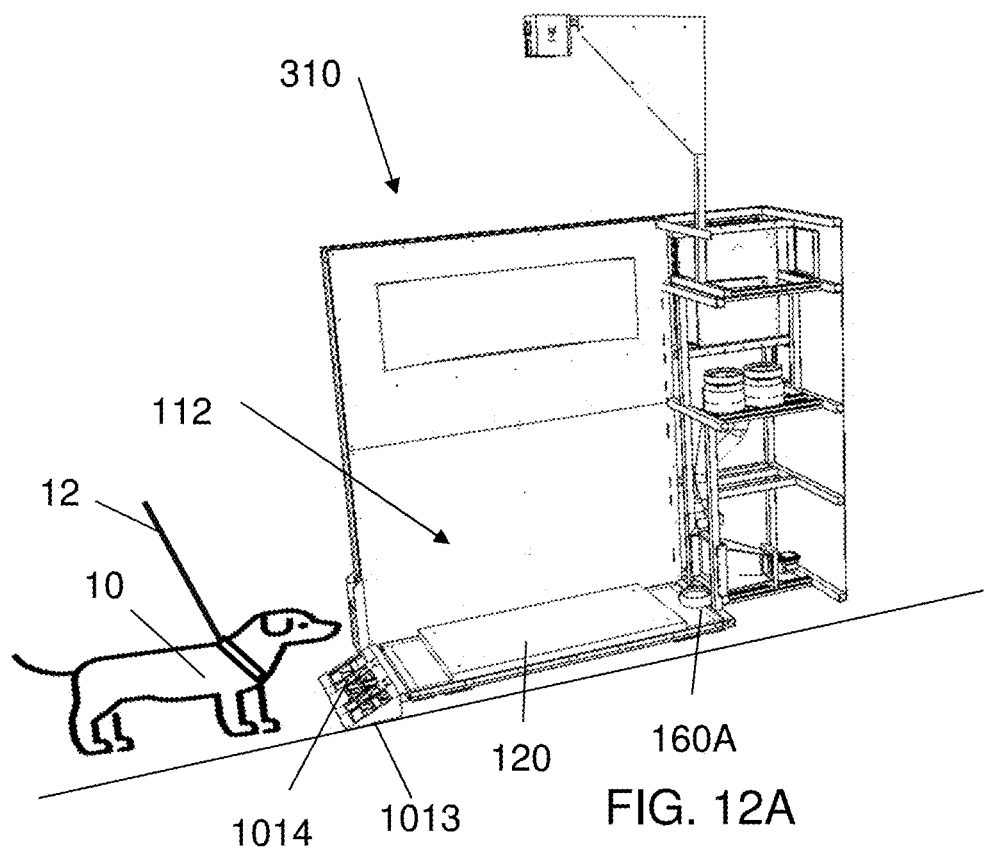
FIG. 12A shows an animal entering the housing.
Figure 12B:
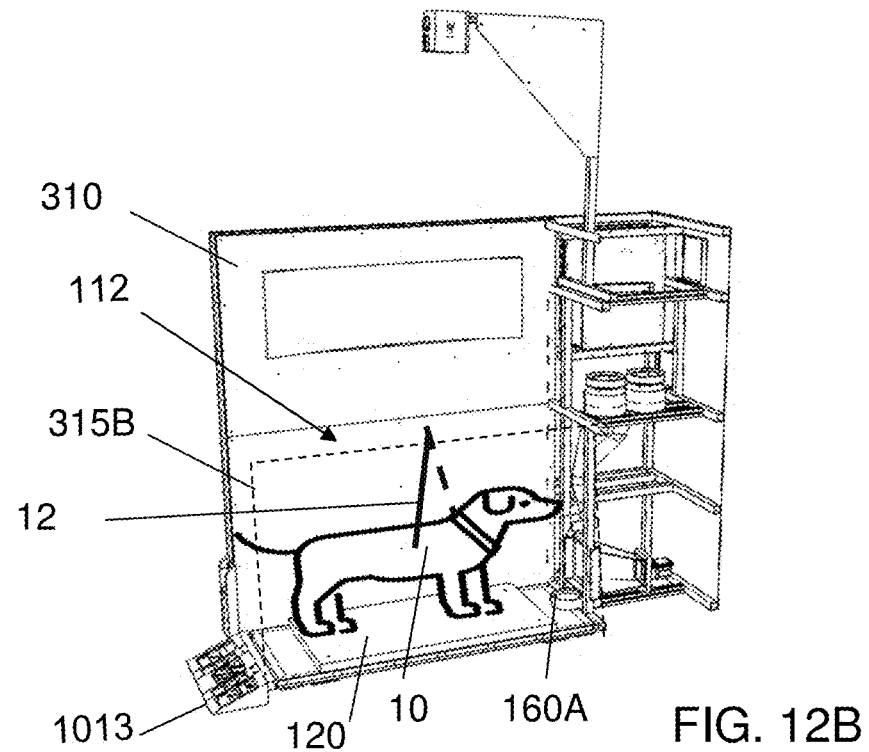
FIG. 12B shows the animal of FIG. 12A eating from the bowl in the analysis zone.

FIG. 12A shows an animal 10 entering the housing shown in FIG. 10A. FIG. 12B shows the animal 10 of FIG. 12A eating from the bowl 160A in the analysis zone 112. In FIG. 12B, the side wall 315A is represented in a dashed line. As the animal 10 enters the analysis zone 112, the animal walks over ramp 1013 and onto the scale 120. The sensor 1014 may detect the animal entering, such as by receiving an ID signal. In the figures, the animal has a leash 12 shown draped over the leash ledge of side wall 315A in FIG. 12B.

Figure 13:
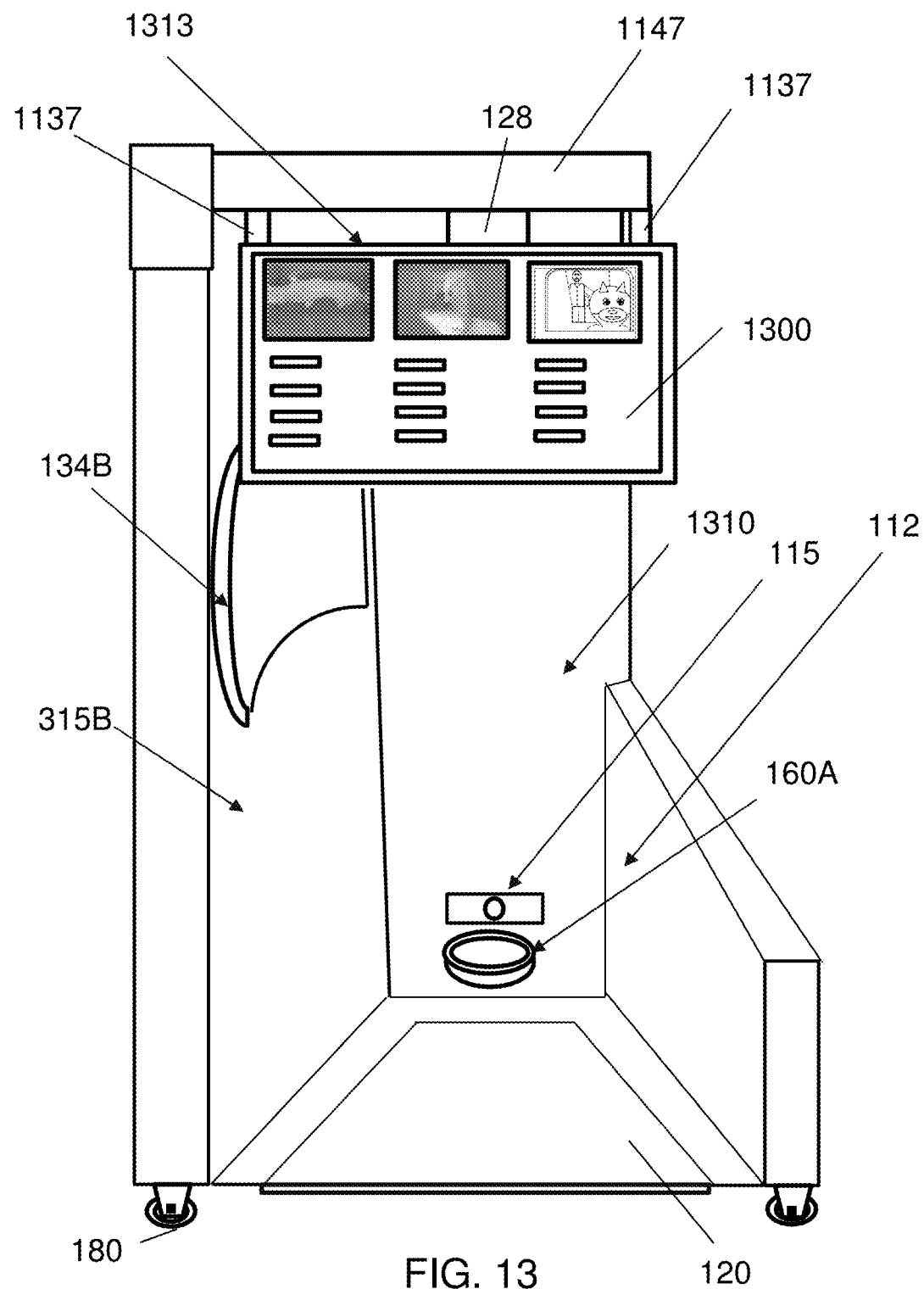
FIG. 13 shows an entry into the analysis zone of the open-top housing.

FIG. 13 shows an entry into the analysis zone 112 of the open-top housing. The housing 1310 is similar to housing 310 previously described in relation to FIGS. 3A-3D. Thus, only the differences will be described. The housing 1310 may include another user interface such as display device 1313 that is mounted to the housing at a viewing location, such as at the entrance to the analysis zone 112. The housing 1310 may include a crossbar 1147 having mounts 1137 coupled thereto. The mounts 1137 are coupled to the display housing of display device 1313 to hang the display device 1313 from the crossbar 1147. The display device 1313 includes a display screen to display one or more graphical user interfaces 1300, or other graphical user interfaces described herein. The graphical user interfaces may display images shown in FIGS. 15A, 15B, 16A, 16B and 17. The graphical user interfaces may include any of the graphical user interfaces described in relation to FIGS. 28-35. In FIG. 13, the area marked as sensor suite 115 may include other sensors described in FIG. 1. The housing may have other cameras distributed in the analysis zone. Example cameras are described in relation to FIGS. 25, 26A and 26B. Cameras of the vision system 128 are mounted over the analysis zone in a manner as previously described.

Figure 14A:
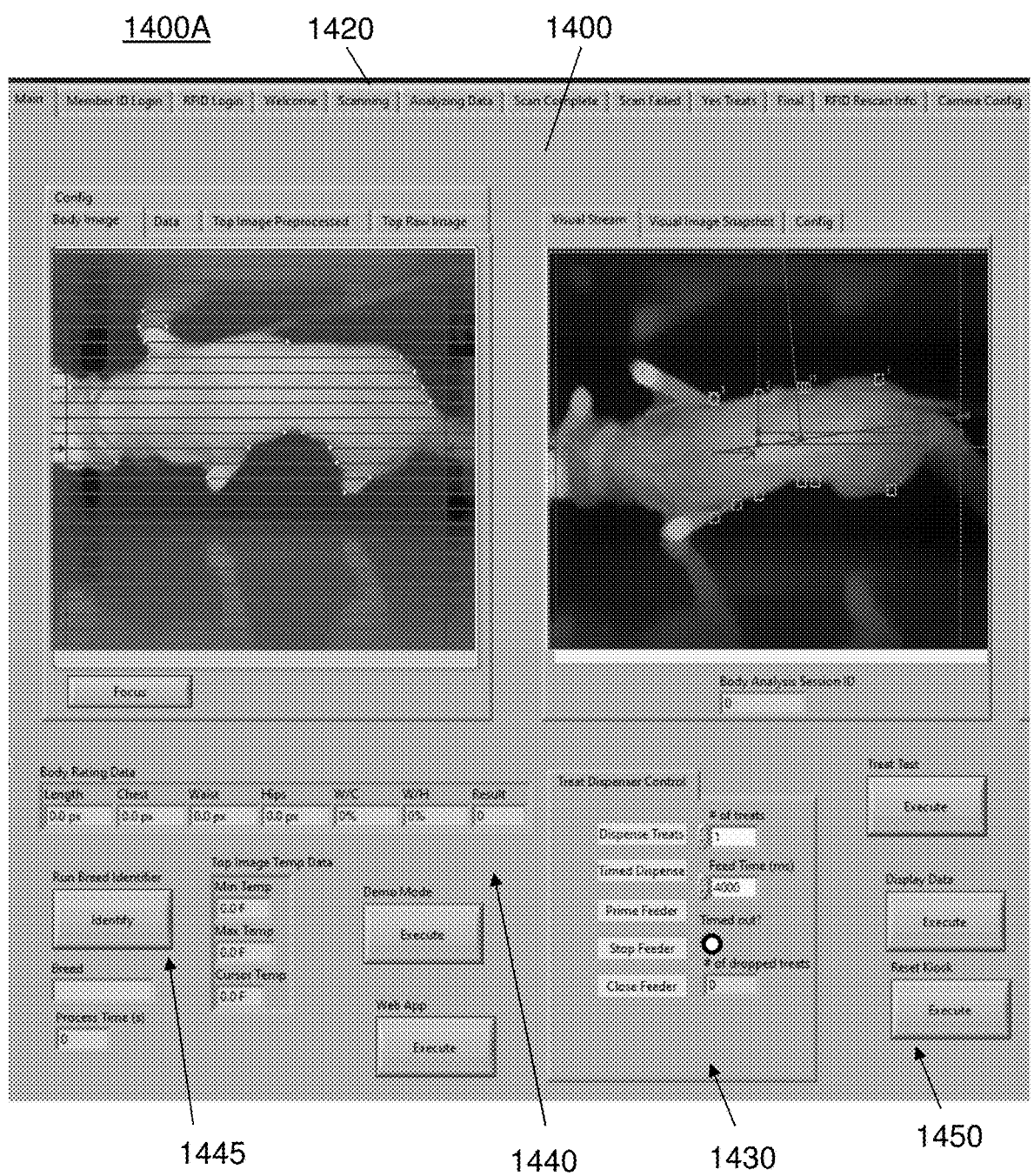
FIGS. 14A and 14B show a graphical user interface displayed on a user interface.
Figure 14B:
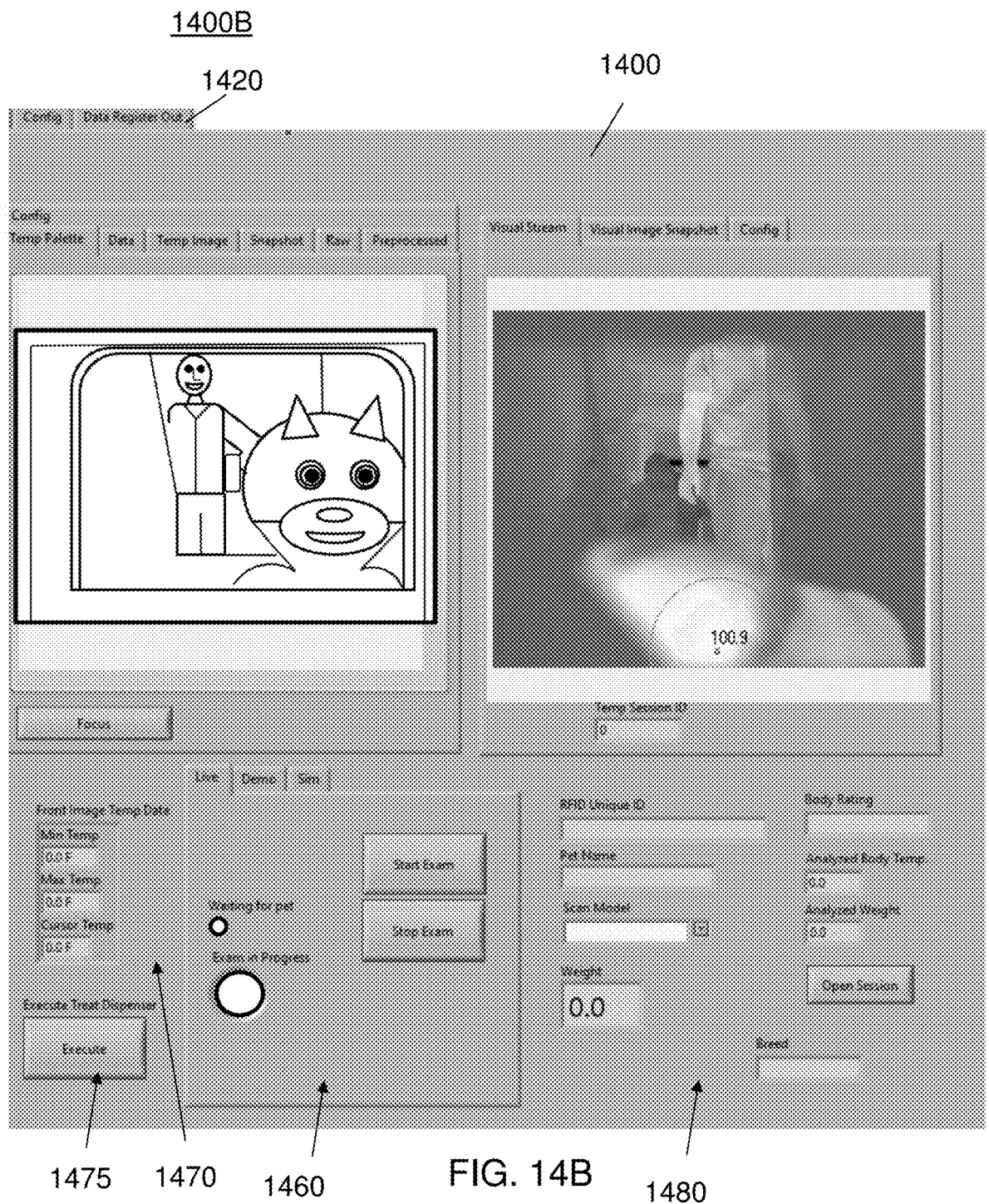

FIGS. 14A and 14B show a graphical user interface 1400A, 1400B that may be displayed on a user interface such as display device 1313 of FIG. 13, user interface 134B or other display device connected to a computing device. However, the graphical user interface 1400A,1400B may be displayed on a computing device of the owner, as well. The graphical user interfaces 1400A and 1400B may be displayed together in a single screen area or expanded to display portions of the user interfaces 1400A and 1400B and together user interfaces 1400A and 1400B will be referred to as examination GUI 1400.

The system 100 may be used to conduct an examination of at least one biological parameter, vital sign, health parameter in the analysis zone. The examination session may be started, managed and/or controlled by GUI 1400. As shown in FIG. 14A, the top of the GUI 1400 may include a tool bar 1420 for navigation and control of the system 100. For example, tool bar 1420 includes navigation control buttons main, member ID login, RFID login, welcome, scanning, analyzing data, scan complete, scan failed, final, RFID rescan information and camera config. The tool bar 1420 in FIG. 14B may include navigation and control buttons for config and data register out. Any buttons of a graphical user interface as described herein may be used for navigation to other screens of the graphical user interfaces or control components of the system, such as cameras, dispensing machines, sensors, etc.

In FIG. 14A, the GUI 1400 includes display windows to display images from one or more of the cameras, such as described in relation to FIGS. 15A, 15B, 16A, 16B and 17. The GUI 1400 includes control buttons 1430 which, when selected, control the dispensing of and track the animal attractant, such as treats. For example, control buttons 1430 includes buttons to dispense treats, timed dispense, prime feeder, stop feeder and close feeder. The buttons may allow a user to delay the dispensing of the treat by setting a timer. The GUI 1400 may allow a user to stop treats from being fed into the chutes, for example, or from being fed into the bowl.

The GUI 1400 may include fields 1440 for displaying the body rating data such as, without limitation, the animal's length, chest, waist, hips, waist/chest (W/C), waist/hips (W/H), and results of the body rating. The term W/C is a ratio of the size of the waist to chest. The term W/H is a ratio of the size of the waist to hips. The GUI 1400 may include execute buttons and fields 1445 for selecting or entering a breed of the animal. The GUI 1400 may include control buttons 1450 to reset the system or kiosk, perform a treat test and display data.

With reference to FIG. 14B, the GUI 1400 may include display windows for displaying various images, such as temperature images and snapshots of the animal. The GUI 1400 may include control buttons 1460 to begin execution of the examination. The GUI 1400 may include indicators to indicate the status of the examination, such as waiting for the pet or whether the examination is in progress. The GUI 1400 may include display fields 1470 for temperature reading data to be displayed. The control button 1475 may be used to start (execute) a treat dispenser routine.

The GUI 1400 may include other data fields, such as fields 1480 to display a unique ID of the animal, body rating score, pet name, weight, breed, analyzed body temperature and scan model.

The method and processes described herein may be performed in the order shown or a different order. One or more of the steps may be performed contemporaneously. One or more of the steps may be omitted in any iteration or added.

Figure 7A:
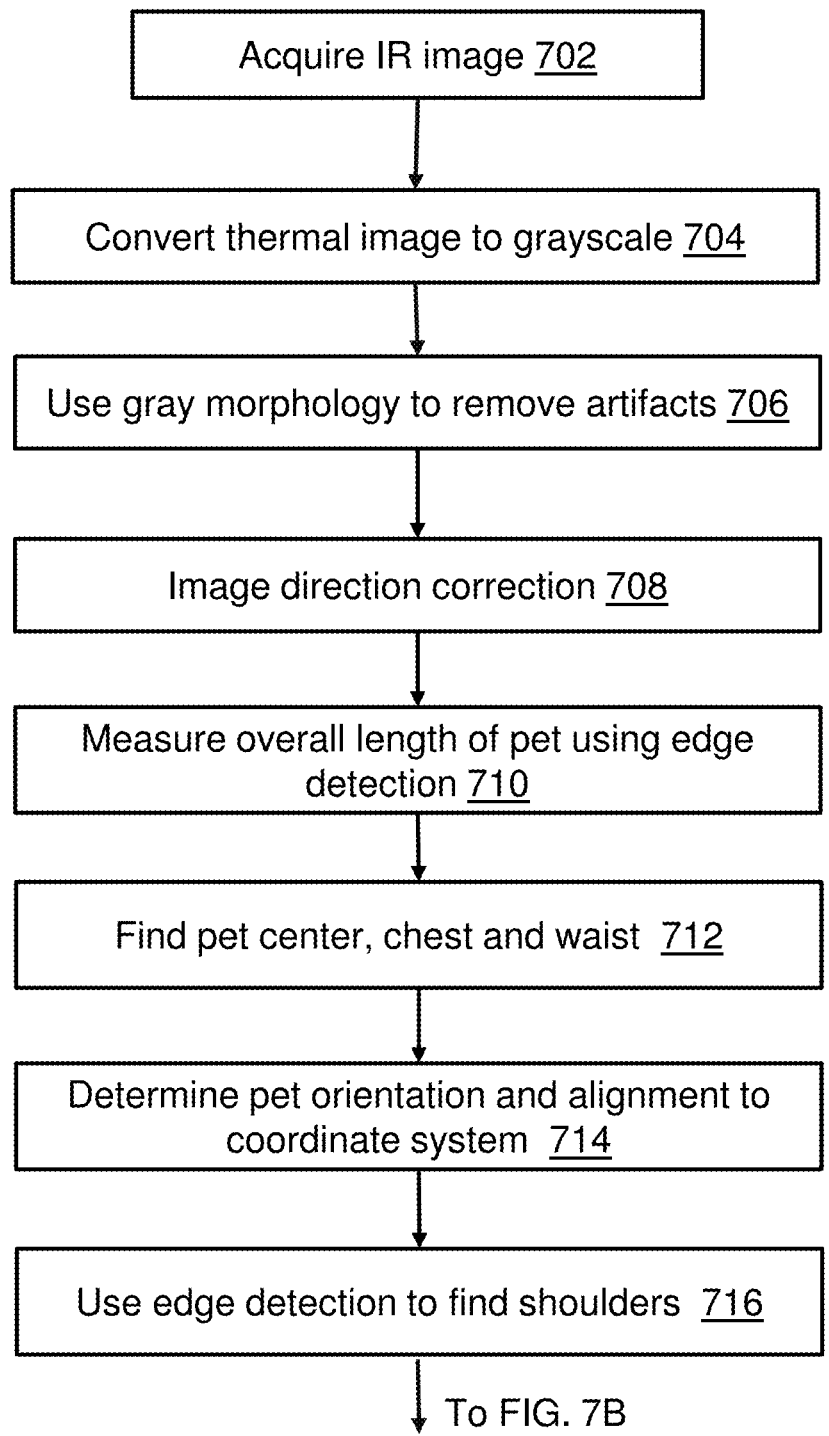
FIGS. 7A and 7B show a flowchart of a process for machine vision operation.
Figure 7B:
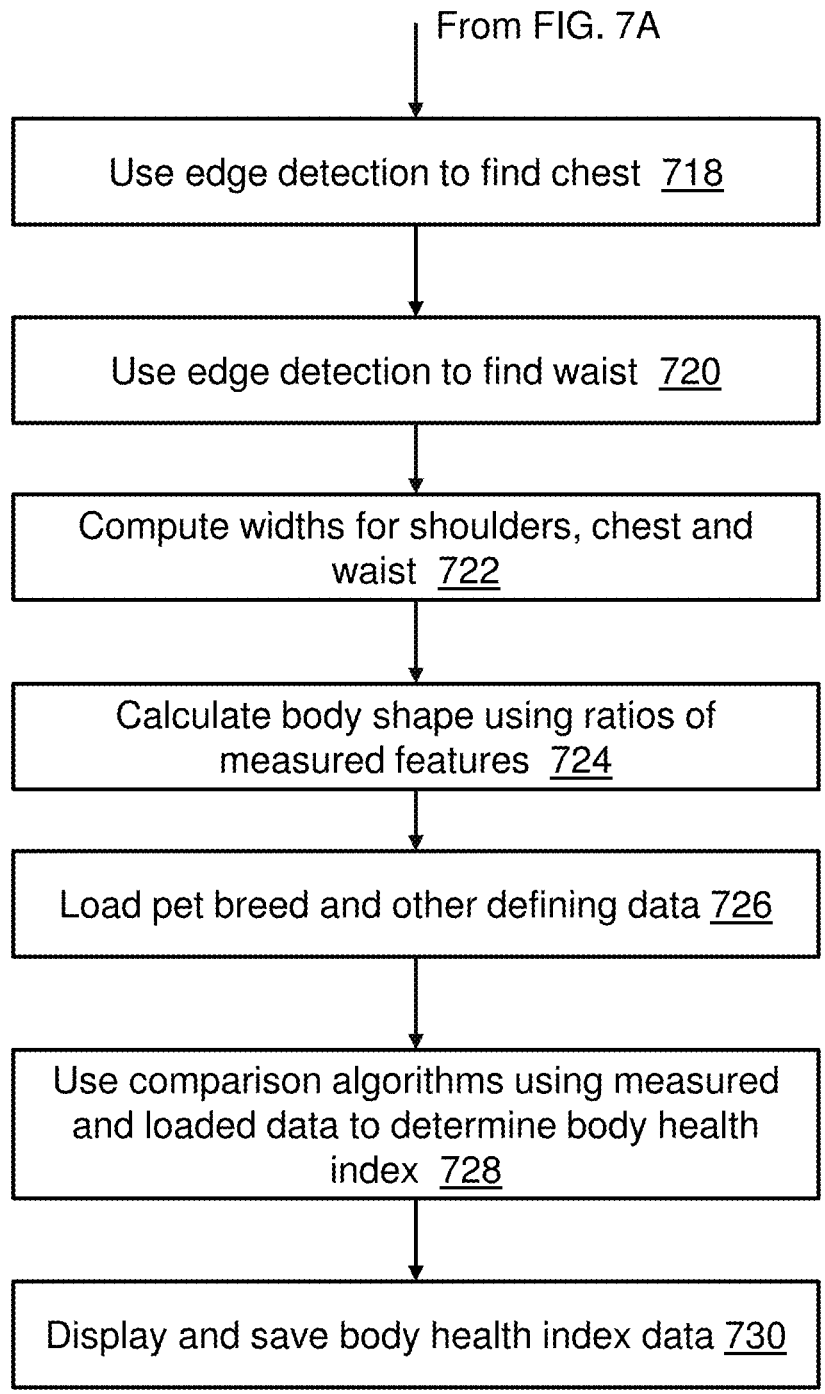

FIGS. 7A and 7B show a flowchart of a process 700 for machine vision operation. The process 700 may include acquiring an IR (thermal) image, at 702. At 704, the process may include converting the acquired image to a grayscale image. At 706, the process 700 includes using a gray morphology to remove artifacts. The process 700 may include, at 708, performing an image direction correction. The process 700 may include, at 710, measuring an overall length of the pet using edge detection from the image data.

The process 700 may include, at 712, finding/locating from the image data a pet center, chest and waist. The process 700 may include, at 714, determining from the image data pet orientation and alignment to a coordinate system. The process 700 may include, at 716, performing edge detection to find/locate shoulders in the image data. With reference to FIG. 7B, the process 700 may include, at 718, performing edge detection to find/locate chest in the image data. The process 700 may include, at 720, performing edge detection to find/locate the waist in the image data.

The process 700 may include, at 722, computing widths for each of the shoulders, chest and waist. The process 700 may include, at 724, calculating body shape using ratios of measured features. For example, ratios of waist to chest may be used in determining whether the animal has an ideal weight, obese and/or severely obese. The breed may have certain ratios of waist to chest, shoulders to waist or belly, for example. The process 700 may include, at 726, loading the pet breed and other defining information. The process 700 may include, at 728, performing a comparison using the measured data with the loaded breed data to determine the body health index of the animal. The process 700 may include, at 730, displaying on the user interface the body health index and saving the body health index in the client file.

Figure 8A:
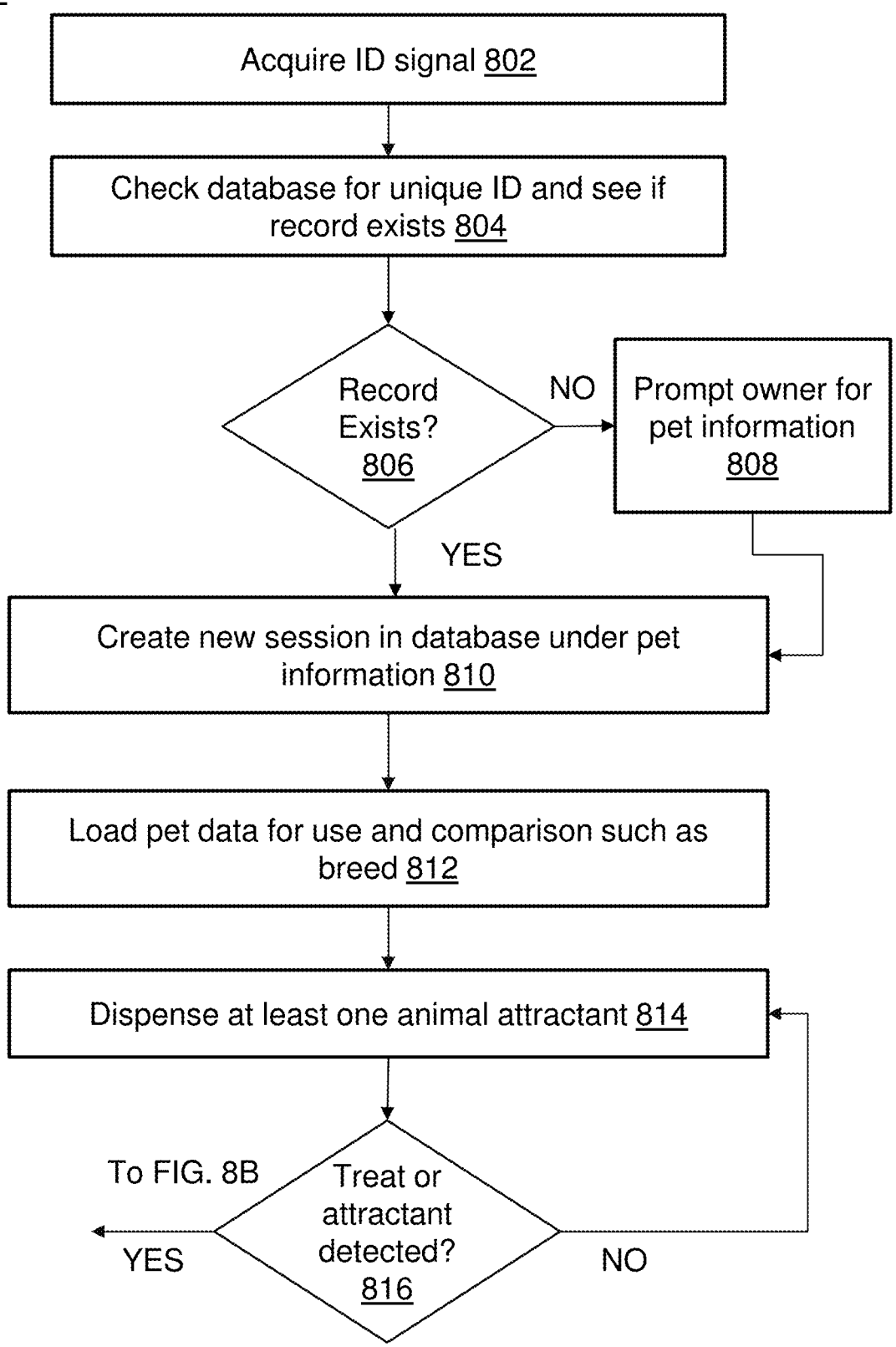
FIGS. 8A-8C show a flowchart of a process for health sensing and analysis.
Figure 8B:
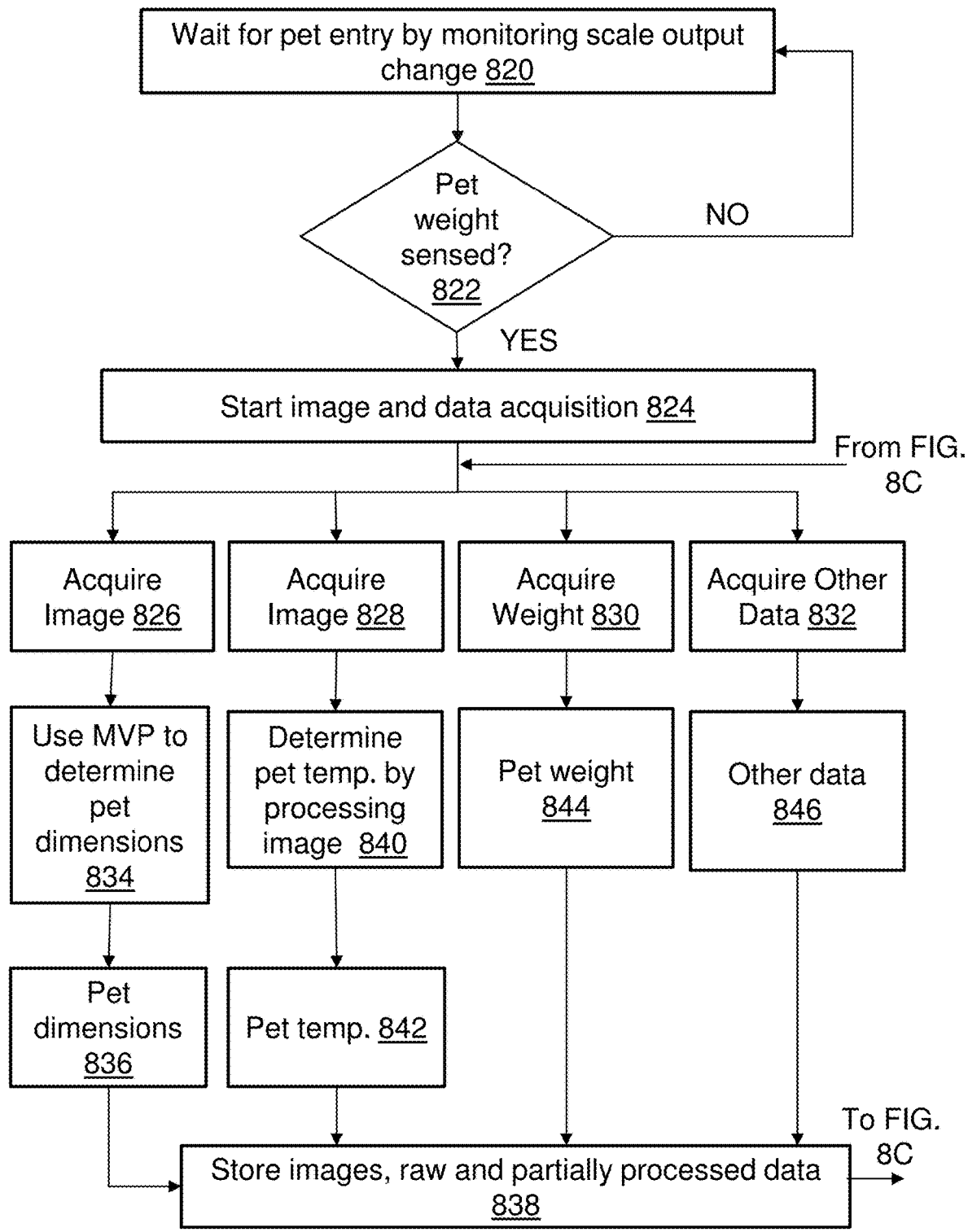
Figure 8C:
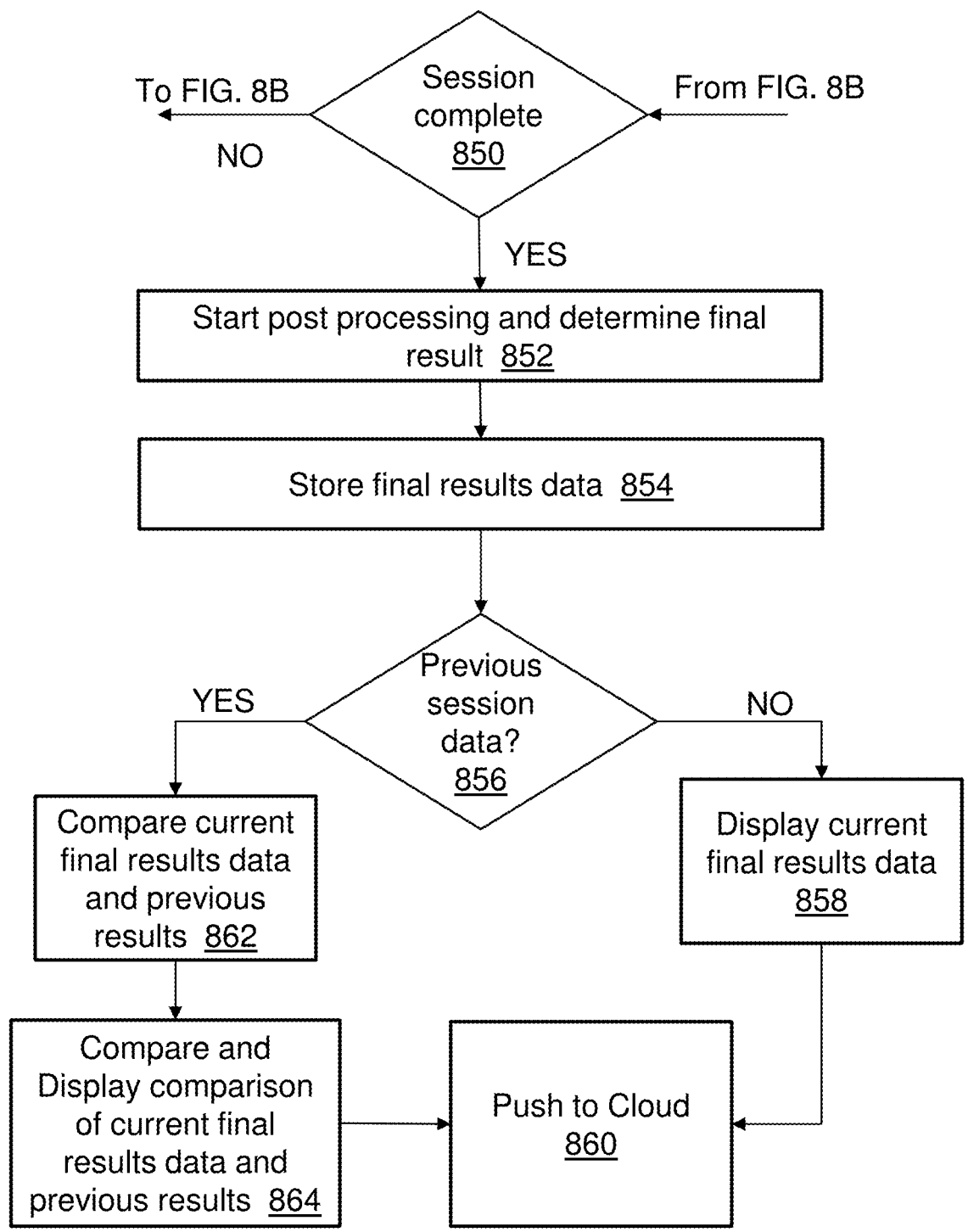

FIGS. 8A-8C show a flowchart of a process 800 for health sensing and analysis. The process 800 may include, at 802, acquiring an ID signal such as, without limitation, and RFID signal. The process 800 may include, at 804, checking client database for unique ID to determine if a record already exists. The process 800 may include, at 806, determining whether a record exists. If the determination, at 806, is "NO," the process 800 may include, at 808, prompting the user/owner for animal information. If the determination, at 806, is "YES," the process 800 may include, at 810, creating a new session in the database under the pet information/record. From step 808, the process 800 may proceed to step 810 to create a new session for a new client.

The process 800 may include, at 812, loading pet specific data for use and comparison such as breed information. The pet specific data and breed information may be used in later processes of analysis. The process 800 may include, at 814, dispensing at least one animal attractant. The process 800 may include, at 816, determining whether the treat or attractant is detected. If the determination, at 816, is "NO," the process returns to step 814. If the determination, at 816, is "YES," the process 800 may include, at 820, waiting for the pet entry for monitoring scale output change, as shown in FIG. 8B.

As shown in FIG. 8B, the process 800 may include, at 822, determining whether the animal's weight is sensed. If the determination, at 822, is "NO," the process returns to step 820. If the determination, at 822, is "YES," the process 800 may include, at 824, starting the image and data acquisition. The process 800 may include, at 826 and 828, at least one image is acquired. The process 800 may include, at 830, the weight is acquired and, at 832, other data is acquired.

The process 800 may include, at optional 834, after the at least one image is acquired, using machine vision processing (MVP) to determine animal dimensions. The at least one image that is acquired may include a first fiducial marker, which is identified in the at least one image. Additionally, the machine vision processing may include determining a second fiducial marker in the at least one image. The process 800 may capture multiple images from different directions to capture all of the dimensions.

The process 800, at optional 834, denoted in dashed lines, may find and locate at least one of a waist of the animal, a chest of the animal, width of shoulders, and a longitudinal center of the animal using at least one of the first fiducial marker and the second fiducial marker. The process 800, at optional 834, may measure the at least one of a waist of the animal, a chest of the animal, width of shoulders, and a longitudinal center of the animal to create and store real-time measured data. The created real-time measured data is the identified dimensions of the body. In some embodiments, artificial intelligence (AI) and machine learning (ML) algorithms may be used to find and locate animal features. The dimensions are useful in determining whether the weight of the animal indicates an underweight, ideal weight, obese weight or severely overweight.

The process 800 may include, at 836, the animal dimensions information are obtained. The process 800 may include, at 838, the images, raw and partially processed data are stored.

The process 800 may include, at 840, after an image is acquired at 828, determining the animal's temperature through processing of IR image. The process 800 may include, at 842, identifying the pet temperature data, which is then set and stored at 838. The process 800 may include, at 844, after acquiring the weight, at 830, identifying the weight data and, at 838, storing the weight.

The process 800 may include, at 846, after acquiring other data, at 832, identifying the other data and, at 838, storing the other data. The acquired other data may include data captured by the sensor suite 115 to detect one or more of the heartbeat, breath, breath vapor, breathing pattern, breathing rate and dental condition. The acquired other data may include an eye condition, growths, other ailments and skin or coat details of the animal. In some embodiments, acquiring other data may be derived from any sensor of the sensor suite 115 and/or vision system 128. For example, the pixels or pixel clusters of the animal may be evaluated row by row and column by column for health conditions.

Referring now to FIG. 8C, the process 800 may include, at 850, determining whether the session is complete. If the determination, at 850, is "NO," the process returns to steps 826, 828, 830 and 832 until all data is acquired. If the determination, at 850, is "YES," the process 800 may include, at 852, starting post processing of all data and determining final results. The process 800 may include, at 854, storing the final results.

The process 800 may include, at 856, determining whether the previous session results are available. If the determination, at 856, is "NO," the process 800 may include, at 858, displaying the current final results. Then the process, at 860, may include pushing all the data to the cloud computing system. The data at the cloud computing system may be accessible by the owner using a personal communication device or personal computing device. If the determination, at 856, is "YES," the process 800 may include, at 862, comparing the current session's final results to the previous session's final results. The process 800 may include, at 864, displaying the current and previous final results and comparison data. Step 864 is followed by step 860.

Figure 9A:
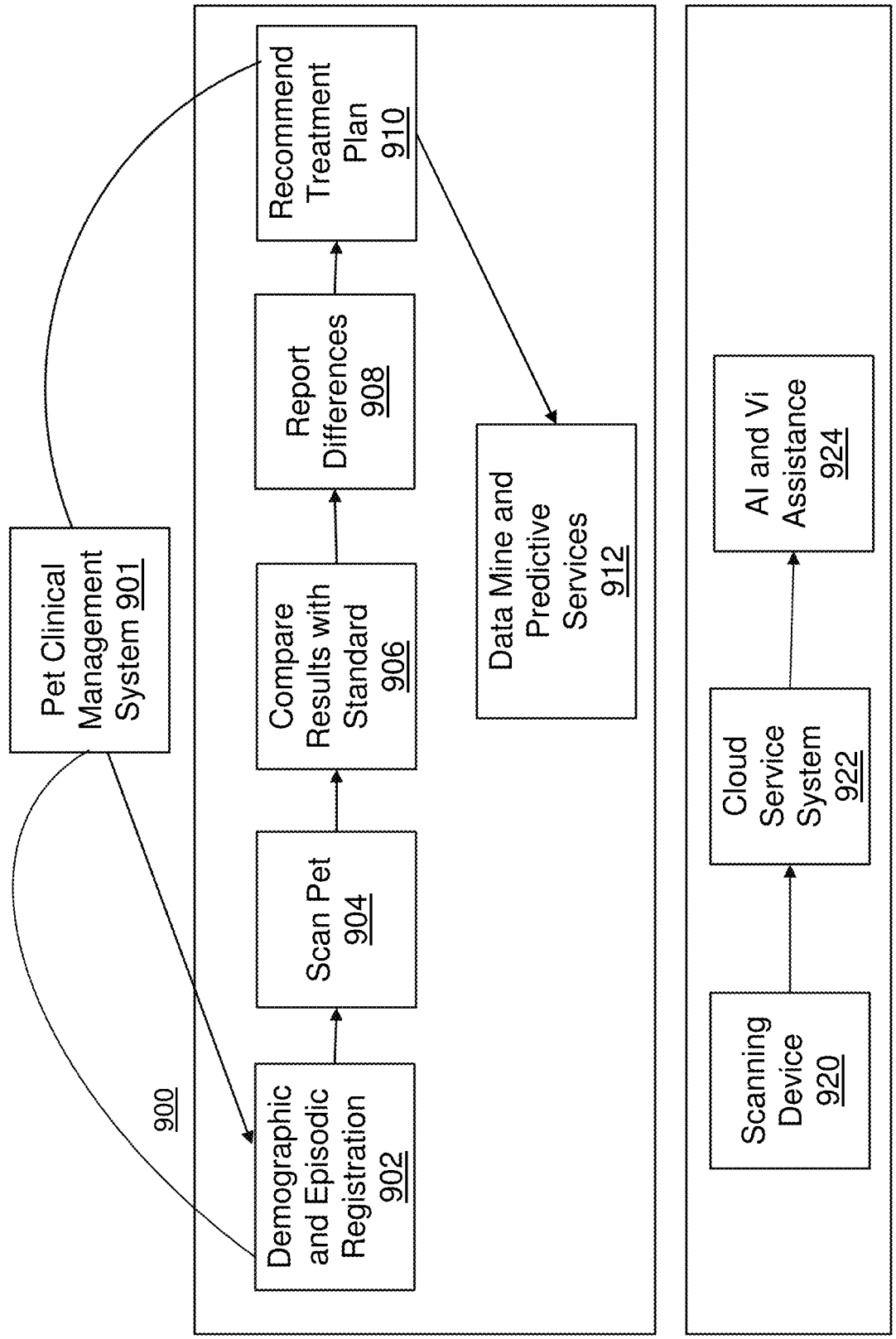
FIG. 9A shows a flowchart of a process for animal clinical management system.

FIG. 9A shows a flowchart of a process 900 for animal clinical management system 901. The process 900, at 902, may include demographic and episodic registration. At 904, the process 900 may include scanning the animal. The process 900, at 906, may include comparing the results with a standard. The process 900, at 908, may include reporting the differences to the user/owner. The process 900, at 910, may include recommending a treatment plan, such as food and/or treat ingredients. The process 900, at 912, may include mining for data for predictive services. The recommendations may be performed by a cloud computing system or a processor coupled to the housing, based on the sensor data from the sensor suite 115 and/or vision system 128. The animal clinical management system 901 may interface with the scanning device 920, a cloud service/computing system 922 and an artificial intelligence (AI) and virtual intelligence (VI) assistance system 924. The artificial intelligence (AI) and virtual intelligence (VI) assistance system 924 may include software and algorithms executed by the cloud service/computing system 922. The scanning device 920 may be included in the sensor suite 115.

Figure 9B:
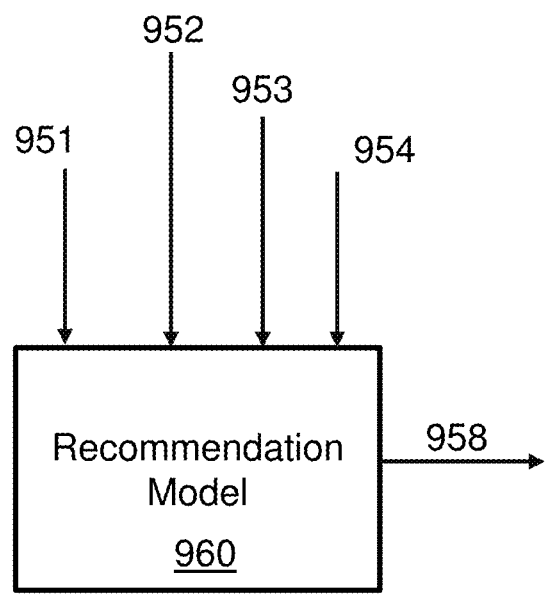
FIG. 9B shows a block diagram of training a recommendation model used to recommend feed nutrients.

FIG. 9B shows a block diagram 950 for training a recommendation model 960 used to recommend feed nutrients. At least one processor, such as the main processor or the cloud computing system, may perform data mining based on the recommended animal feed nutrients that were based on at least one of the analyzed real-time biological data, the identified dimensions (size and shape) of the body, body composition, the breed of the animal, sex of the animal and the age of the animal. The recommended animal feed nutrients are tracked for each animal. The tracked or logged data may be mined for information related to changes in the animal health. The data mining process may look for patterns related to at least one of the biological data 951, dimensions 952, breed 953 and age 954 to update or train the recommendation model 960. Thus, the recommended animal feed nutrients 958 may be updated as the recommendation model for feed nutrients is updated or trained.

In view of the foregoing, the embodiments provides a system with a standalone housing with an analysis zone, a sensor suite, a treat dispenser machine, treat bowl and a feed making machine. The system detects and/or analyzes health from the sensor suite to determine one or more of: weight, body form, body temperature, dental condition, heartbeat and breath. The treat provides guidance of the animal to sensors of the sensor suite by a predisposition of the animal to hunt for the treat in the bowl. Each standalone system may communicate with the cloud computing system to mine for patterns from multiple locations and multiple animal populations. This improves the recommendation model 960 by having a universal population of animals and similar or identical data metrics captured by each system 100.

Figure 19A:
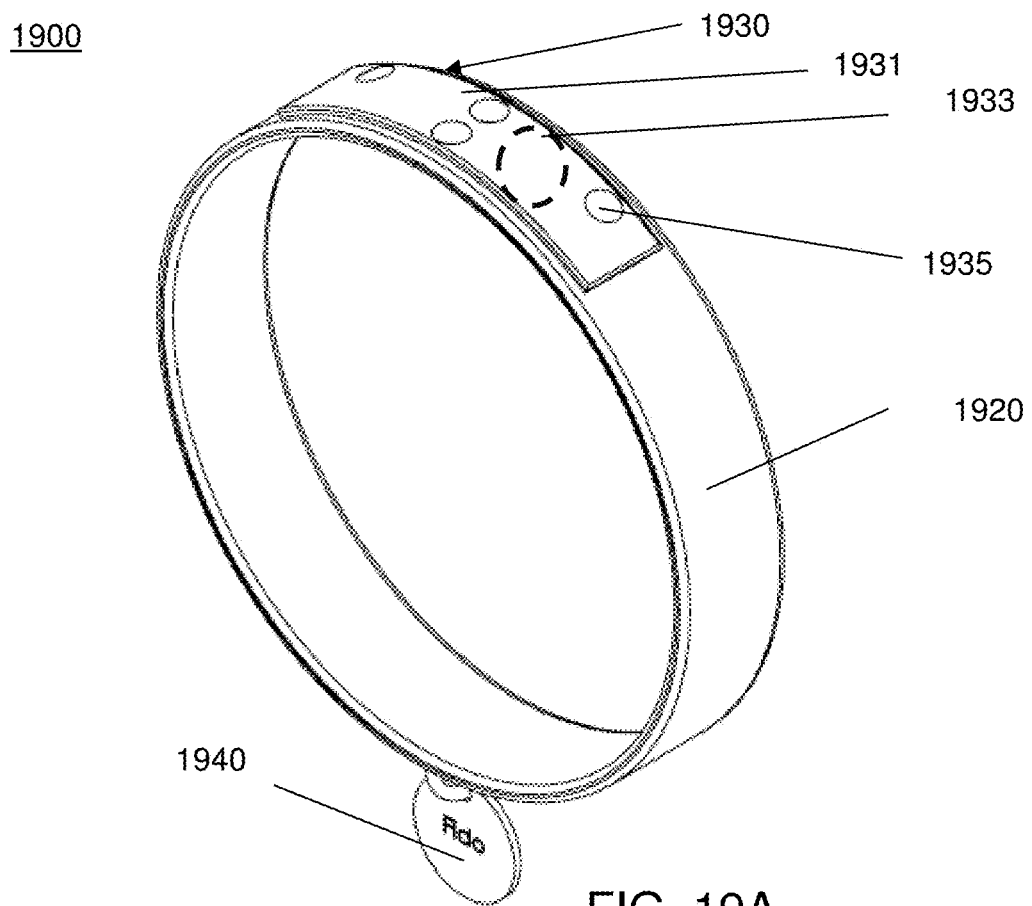
FIGS. 19A-19C show views of a fiducial marker collar.
Figure 19B:
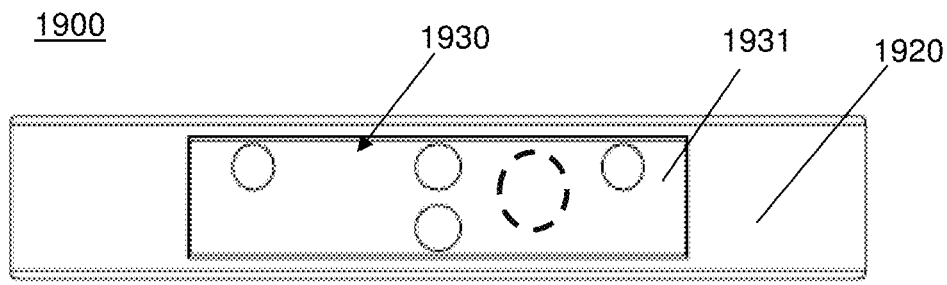
Figure 19C:
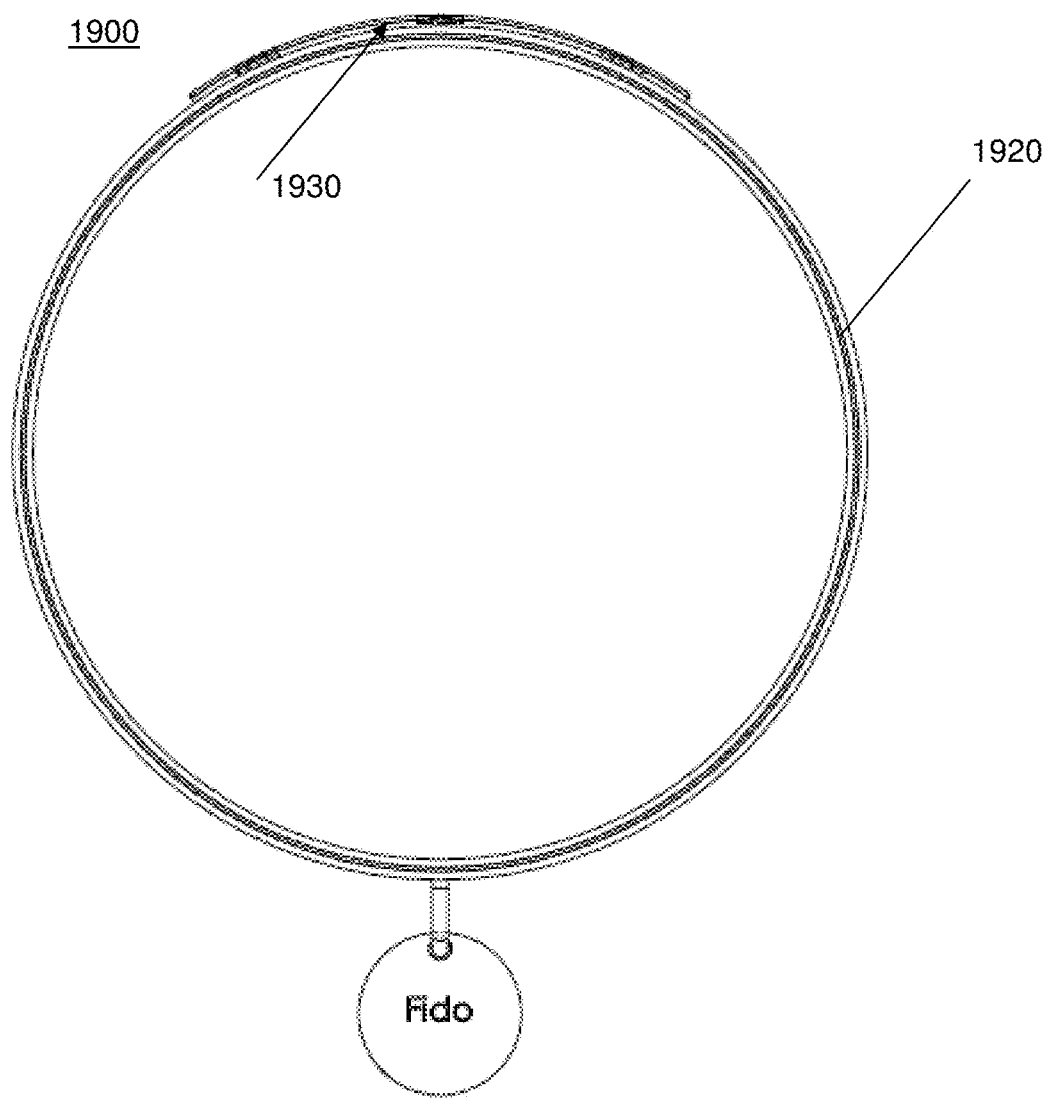

FIGS. 19A-19C show views of a collar 1900. FIG. 19A shows a perspective view of the collar 1900. FIG. 19B shows a top view of the collar 1900. FIG. 19C shows a side view of the collar 1900. The collar 1900 includes a band 1920, which has a length to wrap around an animal's neck. The collar 1900 may be a smart collar that carries an ID tag, for example, such as an RFID tag.

The collar 1900 may include at least one fiducial marker 1930. The marker 1930 may be a strip 1931 having an array of LEDs 1935 with the strip 1931 and LEDs being incorporated into a portion of the band 1920. The strip 1931 may include a battery 1933 for powering the LEDs 1935 in the strip 1931. The collar 1900 may include a name tag 1940. The strip 1931, when worn, may be placed in a manner to illuminate the light in a plane above the animal or along the back of neck of the animal. The name tag 1940 would, in the case of a dog for example, hang down from the front of the neck. In some embodiments, both the strip 1931 and the name tag 1940 may be used to determine an orientation of the animal.

The at least one fiducial marker 1930 may include at least one reflective marker made of a reflective material that is incorporated into at least one strip 1931 on at least one portion of the band 1920. For example, strip 1931 may include a reflective material or a metal strip incorporated into a portion of the band 1920 without the need for LEDs. The at least one marker 1930 may include other fiducial markers incorporated into at least one location of the band 1920. Other markers and orientation devices may be incorporated into the collar 1900 using techniques to identify a particular orientation of the animal wearing the collar.

In some embodiments, the collar 1900 is an orientation indicator device. The band has an interior side, an exterior side and a length to wrap around the neck of an animal. The orientation indicator device (i.e., collar 1900) includes at least one light attached to the band and visible from the exterior side of the band to denote an orientation of the animal. The orientation indicator device includes a tag 1940 coupled to the band to hang by gravity from under the neck. The band 1920 is in the form of a collar with fasteners to fasten the collar around the neck. The fasteners may include hook and loop or VELCRO fasteners. The fasteners may include buckle type fasteners or other fasteners suitable for attaching the band around the animal's neck.

The orientation indicator device may include at least one light. The at least one light may be a first fiducial marker for the animal in the walk-in analysis zone. The tag 1940 may be a second fiducial marker in a walk-in analysis zone. At least one of the first fiducial marker and the second fiducial marker are used to autonomously capture dimensions of the animal by determining an orientation of the animal using the locations of at least one of the markers. In some embodiments, the tag 1940 may be both a fiducial maker and a radio frequency identification (RFID) tag or other ID tag to communicate identifiable information associated with the animal entering in a walk-in analysis zone.

The system may use other orientation indicator devices. For example, a fiducial marker may be placed on the head of an animal, such as between the ears. The fiducial marker may include a low-tack adhesive on one side and a reflective material on the other side, similar to a sticker. The low-tack adhesive allows the sticker to be easily removed from the animal.

In some embodiments, the system includes a housing having a walk-in analysis zone to a bowl having a treat. The system includes an orientation indicator device and a computer vision system, in the walk-in analysis zone, to identify an orientation of an animal in the walk-in analysis zone by detecting the orientation indicator device. The vision system may also capture and determine dimensions of a body of the animal. The system includes at least one processor, in communication with the computer vision system, to analyze the dimensions of the animal and at least one of: recommend animal feed nutrients based on the analyzed dimensions, and cause a feed making machine to make animal feed based on the recommended animal feed nutrients.

In some embodiments, the system includes a scale in the walk-in analysis zone to measure weight of the animal. The at least one processor of the system may analyze the dimensions and the weight of the animal to determine the recommended animal feed nutrients.

In some embodiments, the system includes the feed making machine to make feed for the animal, the bowl; and a treat dispensing chute coupled to the housing, the chute to dispense the treat to the bowl.

The system includes a T&ID sensor 122 at a location entering the housing to receive an ID signal with identifiable information of the animal such as from the orientation indicator device. The at least one processor to further identify an existing log for the animal based on the received ID signal, log into the existing log (i.e., client files 152 in FIG. 1) the dimensions from the computer vision system, and maintain the log of the dimensions in memory for the animal to track the dimensions.

The system may include a treat dispensing machine. The at least one processor controls the treat dispensing machine to autonomously dispense the treat into the bowl, based on the received ID signal. This is intended to attract the animal into the walk-in analysis zone where the bowl is positioned. The ID signal may be used to dispense a custom treat based on a stored animal profile or animal demographics.

The orientation indicator device (i.e., collar 1900) includes a first fiducial marker and a second fiducial marker; and the computer vision system to: find and locate at least one of a waist of the animal, a chest of the animal, width of shoulders, and a longitudinal center of the animal using at least one of the first fiducial marker and the second fiducial marker; and measure the at least one of a waist of the animal, a chest of the animal, width of shoulders, and a longitudinal center of the animal to create real-time measured data. The vision system may locate anatomical parts and determine measurements of the located anatomical parts.

The at least one processor to further determine a breed of the animal determines breed data based on the breed of the animal; performs a comparison using the real-time measure data with a body health index of the animal; and displays on a display device in a viewing area of the housing the determined body health index.

The at least one processor further communicates the body health index to a mobile communication device of an owner of the animal. The processor may communicate the animal's log to the owner's mobile communication device, health related information and recommendations to improve the animal's health.

The at least one processor may calculate a body shape of the animal using ratios of the measured data.

Figure 20:
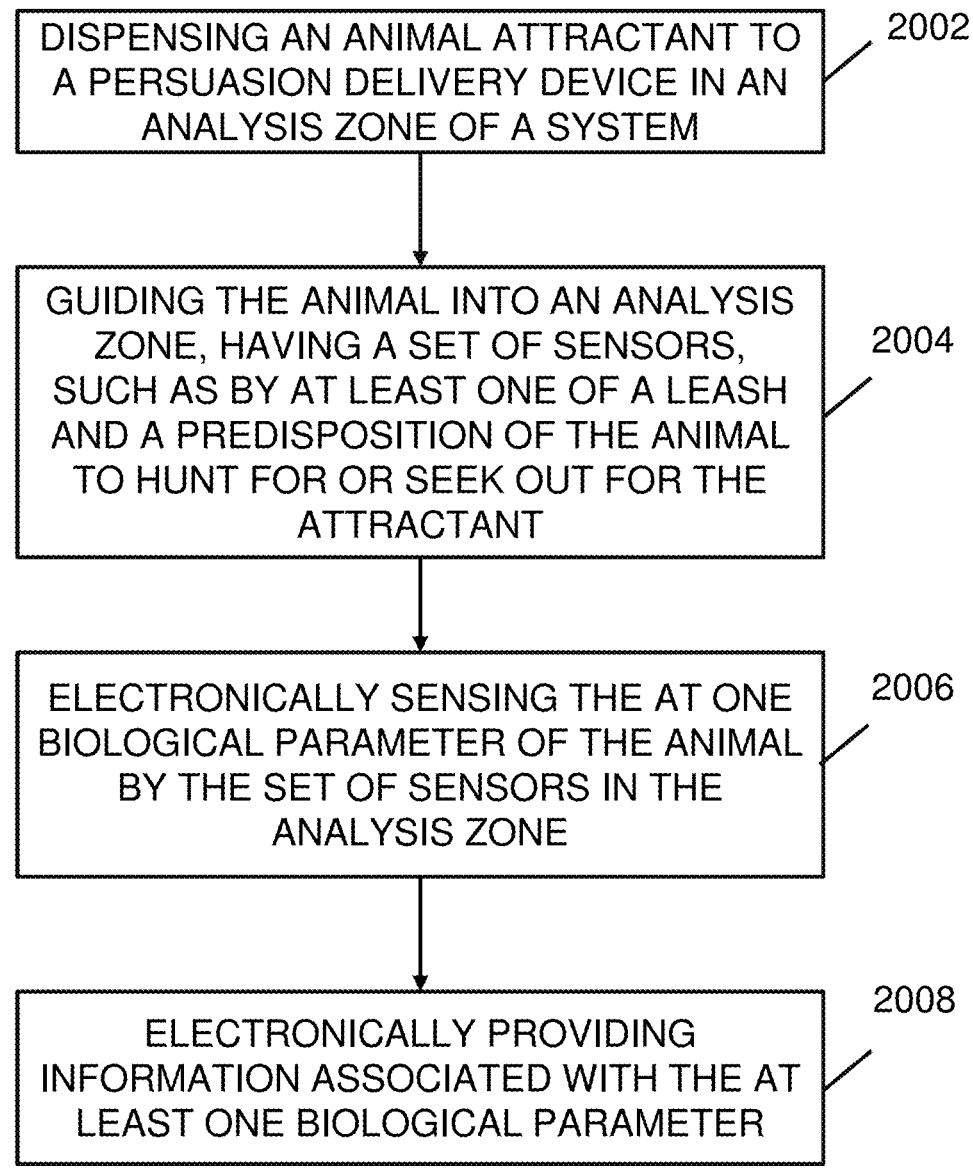
FIG. 20 shows a flowchart of a method for monitoring at least one biological parameter of an animal.

FIG. 20 shows a flowchart of a method 2000 for monitoring at least one biological parameter of an animal. The method may be performed in the order shown or a different order. One or more of the steps may be performed contemporaneously. One or more steps may be added. The method 2000 may include, at 2002, dispensing an animal attractant 137 to a persuasion delivery device 160 in an analysis zone 112 of the system 100. This step may include dispensing an animal treat (i.e., animal attractant 137) into a bowl cavity of a bowl 160A (i.e., persuasion delivery device 160) by a system (i.e., system 100). Alternately, or in addition to, this step may include dispensing at least one sound (i.e., animal attractant 137) into the analysis zone through a speaker 160C (i.e., persuasion delivery device 160). Alternately, or in addition to, this step may include dispensing at least one odor (i.e., animal attractant 137) into the analysis zone through an orifice or permeable membrane 160B (i.e., persuasion delivery device 160).

The method 2000 may include, at 2004, guiding the animal into an analysis zone, having a set of sensors, by at least one of: a leash guided by an owner and a predisposition of the animal to hunt for or seek out the animal attractant.

The method 2000 may include, at 2006, electronically sensing the at one biological parameter of the animal by the set of sensors while the animal is in the analysis zone. This step may include electronically sensing the at one biological parameter of the animal by the set of sensors as the animal eats the treat (i.e., animal attractant 137) in the bowl.

The method may include, at 2008, electronically providing information associated with the at least one biological parameter. The providing of the information may include displaying on a user interface 134B (FIG. 1) which may include a display device and/or communicating the information to a personal communication device of the owner.

The at least one biological parameter may include at least one health parameter of the animal. The at least one health parameter of the animal includes one or more of: a breath vapor; a breathing pattern; a breathing rate; a dental condition; an eye condition; growths; and/or other ailments. The at least one health parameter may include a weight of the animal, temperature of the animal, and/or skin or coat details of the animal.

The electronically sensing, at 2006, may include at least one of: sensing by a microphone of the set of sensors to capture breathing data in an area in proximity to the bowl to determine the breathing rate as the animal eats the treat from the bowl; sensing by a gas analyzer of the set of sensors to sense the breath vapor in the area in proximity to the bowl as the animal eats the treat from the bowl; and sensing by a microphone of the set of sensors in proximity to the bowl to determine a heartbeat of the animal as the animal eats the treat from the bowl.

Figure 21:
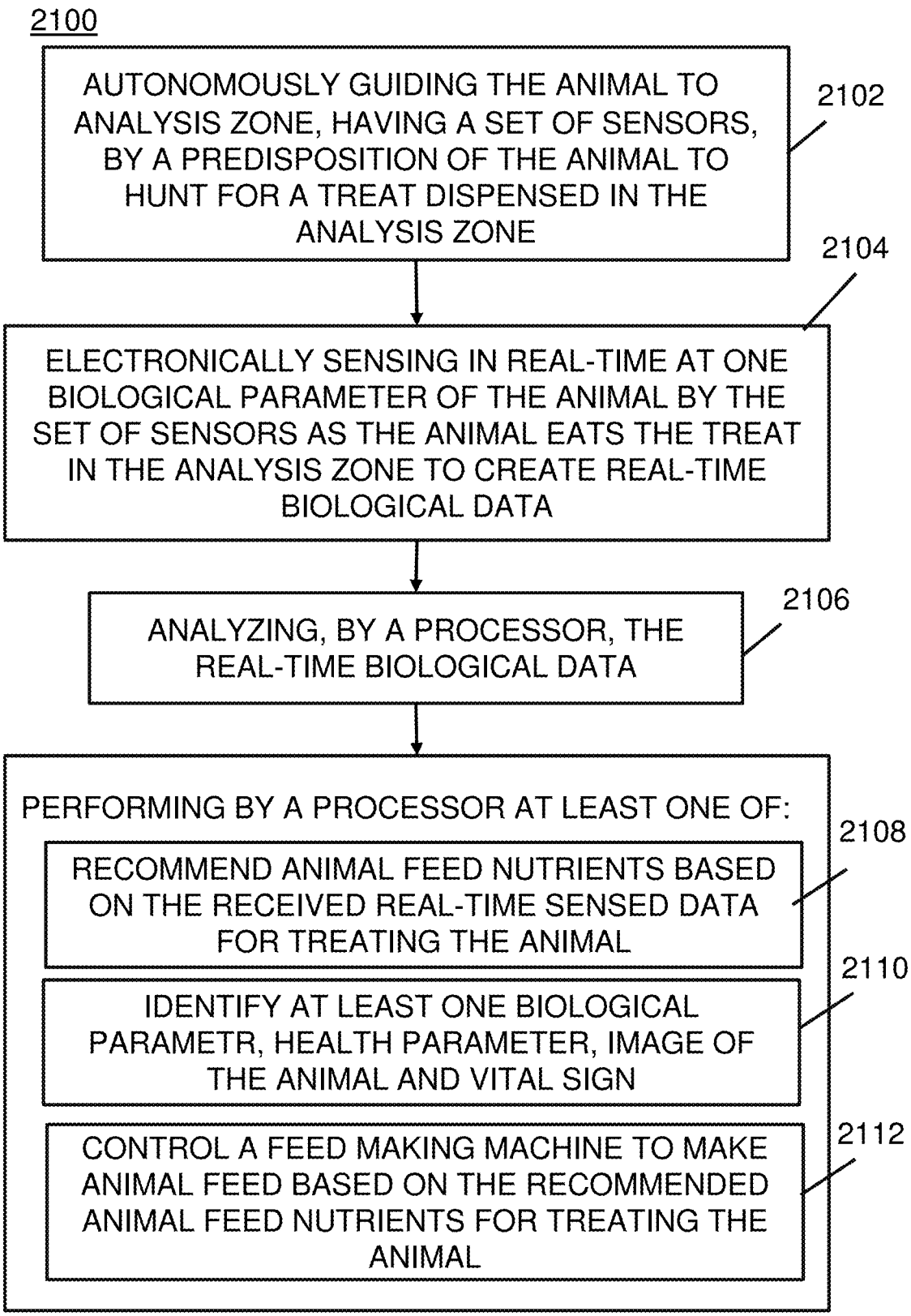
FIG. 21 shows a flowchart of a method for creating animal feed.

FIG. 21 shows a flowchart of a method 2100 for creating animal feed. The method 2100 for creating animal feed may include, at 2102, autonomously guiding the animal to an analysis zone of a kiosk housing, having a set of sensors, by a predisposition of the animal to hunt or seek out an animal attractant dispensed into the analysis zone. The method 2100 may include, at 2104, electronically sensing in real-time at one biological parameter of the animal by at least one sensor of a set of sensors as the animal eats the treat in the analysis zone to create real-time biological data. The method 2100 may include, at 2104, analyzing, by a processor, the real-time biological data. The method 2100 may include, at 2106, performing, by the processor, at least one of: recommending animal feed nutrients based on the analyzed real-time biological data, at 2108; identifying at least one of biological data, health parameter, vital sign and image of the animal at 2110; and causing a feed making machine to make animal feed based on the recommended animal feed nutrients, at 2112.

The method may include receiving, by the processor, an order and payment for the animal feed having the recommended animal feed nutrients and controlling, by the processor, the feed making machine to make the ordered animal feed, such as using user interface 134C of the feed making machine 138 (FIG. 2).

The method may include when controlling, by the processor, the feed making machine, selecting a plurality of feed ingredients having the animal feed nutrients; operating a mixer to mix the selected ingredients of the plurality of ingredients; and forming pellets from the mixed ingredients. The pellets are the ordered animal feed. The controlling, by the processor, the feed making machine includes outputting the pellets into a container that can be purchased or provided to the owner.

The method may include sensing weight of the animal in the analysis zone.

The method may include determining, by the processor, a breed of the animal and current body weight of the animal. The animal feed nutrients may be recommended based on the breed and current body weight of the animal.

The at least one biological parameter of the animal includes one or more of: a breath vapor; a breathing pattern; a breathing rate; heartbeat; and a dental condition. The recommended animal feed nutrients, by the processor, may be further based on at least one of: a breed of the animal; sex of the animal; and age of the animal.

The method may include sensing by the set of sensors vital signs.

The method may include receiving an RFID or other ID signal associated with the animal, wherein the processor tracks the at least one biological parameter of the animal by: logging in a log the sensed at least one biological parameter of the animal based a received RFID or ID signal; and maintaining the log of the sensed at least one biological parameter in memory.

In view of the foregoing disclosure, the system includes a housing having an analysis zone and a bowl mounted to the housing at one end of the analysis zone. The system includes a treat dispensing chute to dispense an animal treat or animal attractant into a bowl cavity of the bowl. The system includes a set of sensors located in the analysis zone to sense real-time data related to health of an animal in the zone. The set of sensors includes at least one sensor to sense in proximity to the bowl cavity at least one biological parameter of the animal related to the health.

An aspect includes a method for sensing at least one biological parameter of an animal. The method includes dispensing a treat into a bowl cavity of a bowl by a system. The method includes autonomously guiding the animal to an analysis zone, having a set of sensors, by a predisposition of the animal to hunt or seek out for the treat or animal attractant; and electronically sensing the at one biological parameter of the animal by the set of sensors as the animal eats the treat in the analysis zone. The method includes providing information associated with the at least one biological parameter.

Figure 18:
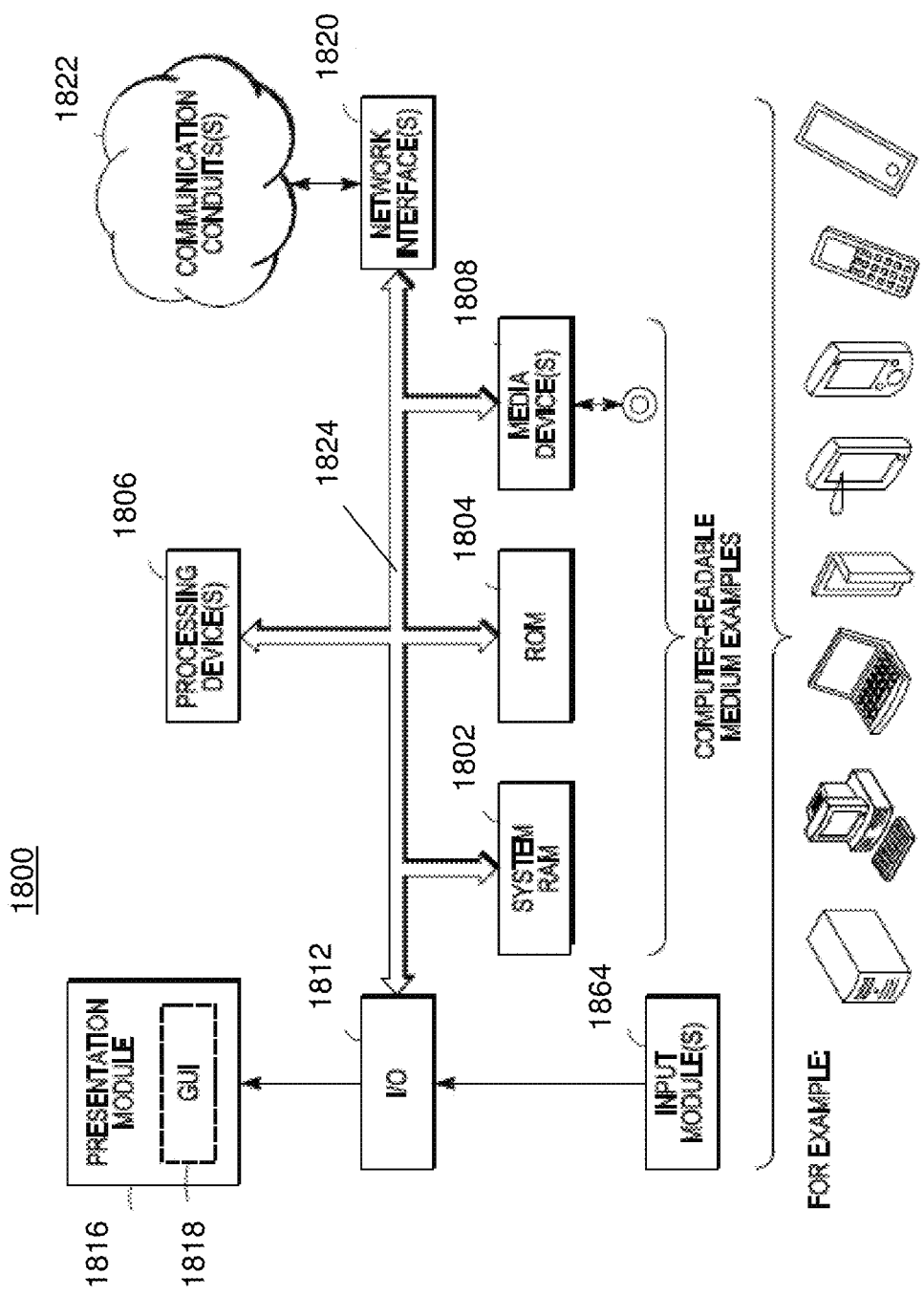
FIG. 18 shows a computing device.

Referring now to FIG. 18, in a basic configuration, a computing device 1800 (i.e., computing device 150) may include any type of stationary computing device, server, personal computer (PC) or a mobile computing device. The cloud computing system may include a server which allows the computing device 150 to communicate the health data, analysis and/or final report. The cloud computing system may include components of a computing device 1800.

The computing device 1800 may include one or more processing devices 1806 and system memory in a hard drive. One of the processing device may be a main processor at the housing. Depending on the exact configuration and type of computing device 1800, system memory may be volatile (such as RAM 1802), non-volatile (such as read only memory (ROM 1804), flash memory, and the like) or some combination of the two. A system memory may store an operating system, one or more applications, and may include program data for controlling the operations of the sensor suite 115, dispensing machines 136 and feed making machine 138 of system 100, for example. The program data may, when executed, establish a web-based session, and communicate using wired or wireless communication protocols to store data in a cloud computing system. The program data may be configured to send data to a mobile device or body-worn computing device worn by the user/owner. For example, information displayed on the user interfaces 134A, 134B may also be displayed on a display of the user's computing device.

The foldable housing 2210 of FIGS. 22A-22D will now be described for use in system 100 of FIG. 1. The system 100 has been previously described. Thus, only the differences in the housing 2210 relative to any of the previous housings will be described in detail below with some of the components of the system 100 omitted to prevent overcrowding in the drawings.

Figure 22A:
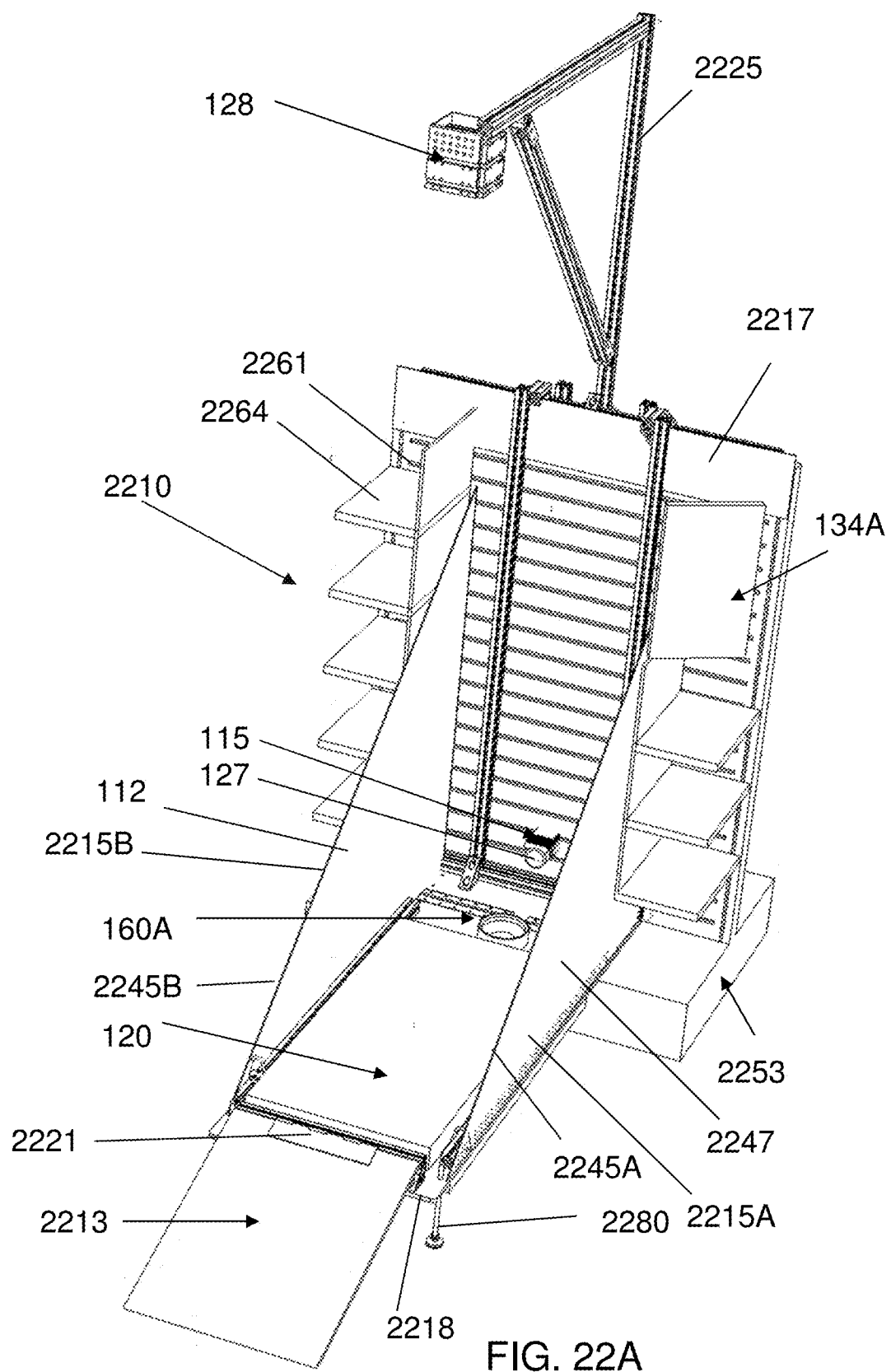
FIG. 22A illustrates a perspective view of a foldable housing of the system in an unfolded state according to an embodiment.
Figure 22B:
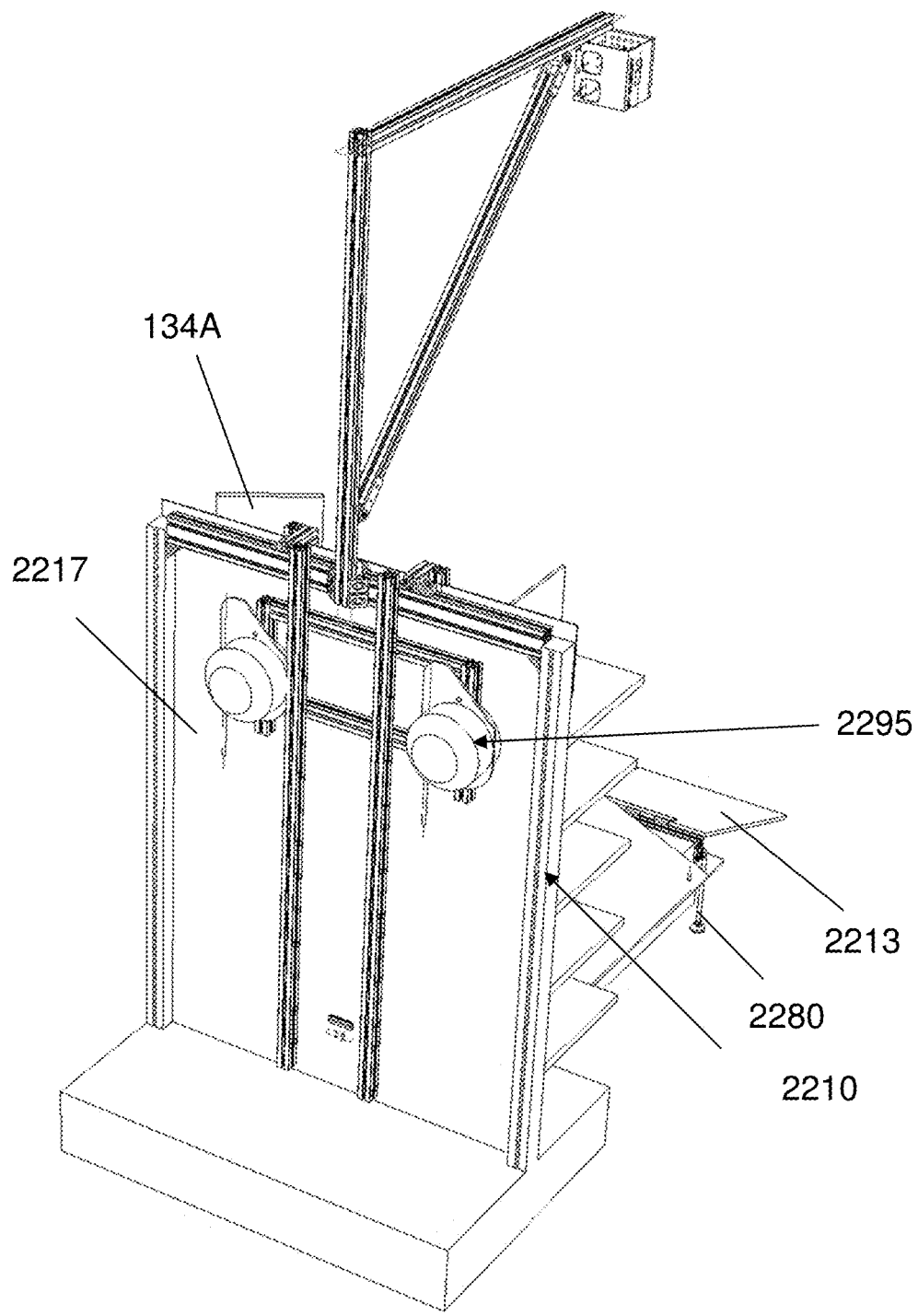
FIG. 22B illustrates a perspective back view of the housing of FIG. 22A.
Figure 22C:
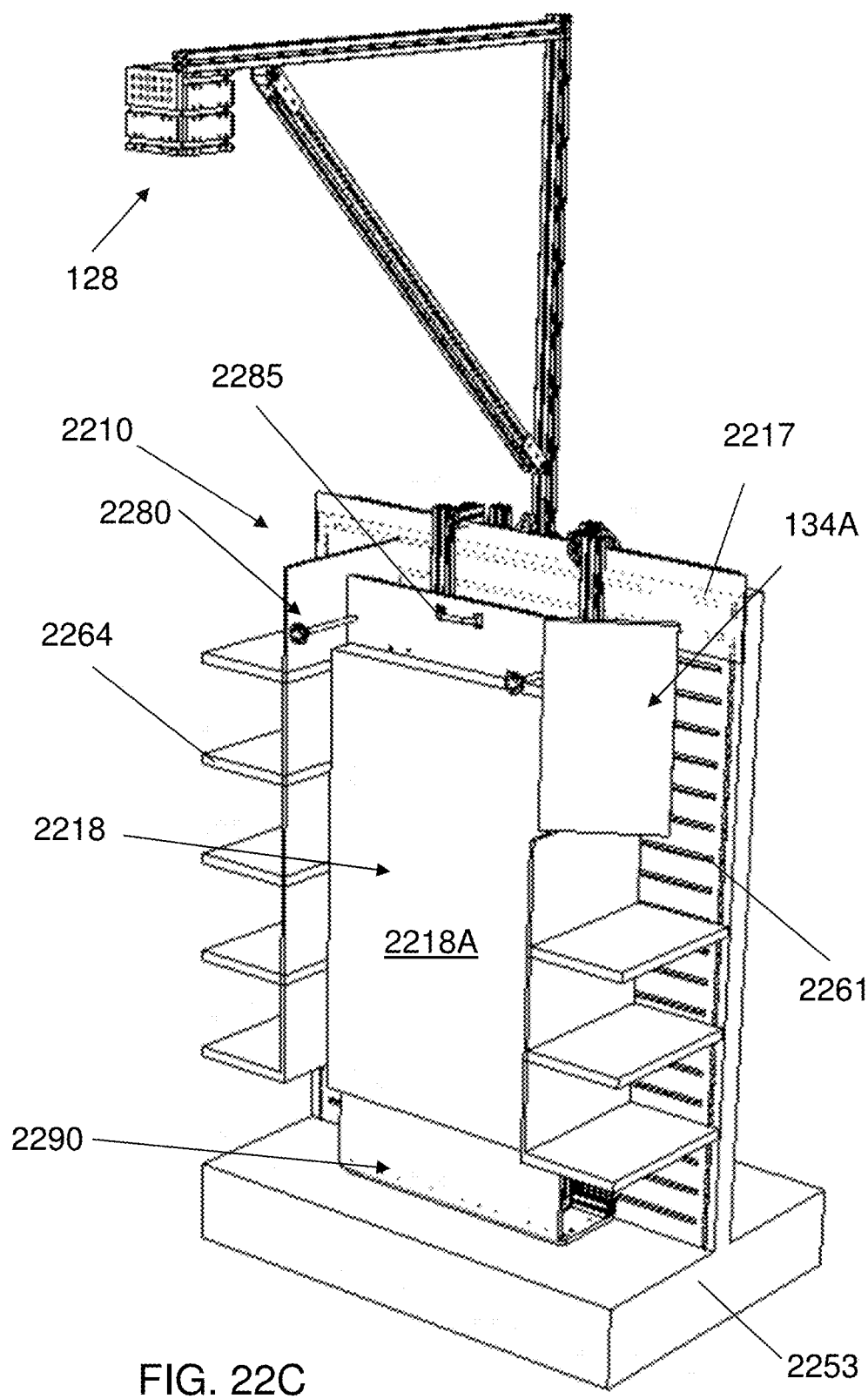
FIG. 22C illustrates a perspective view of the housing of FIG. 22A in a folded state according to an embodiment.
Figure 22D:
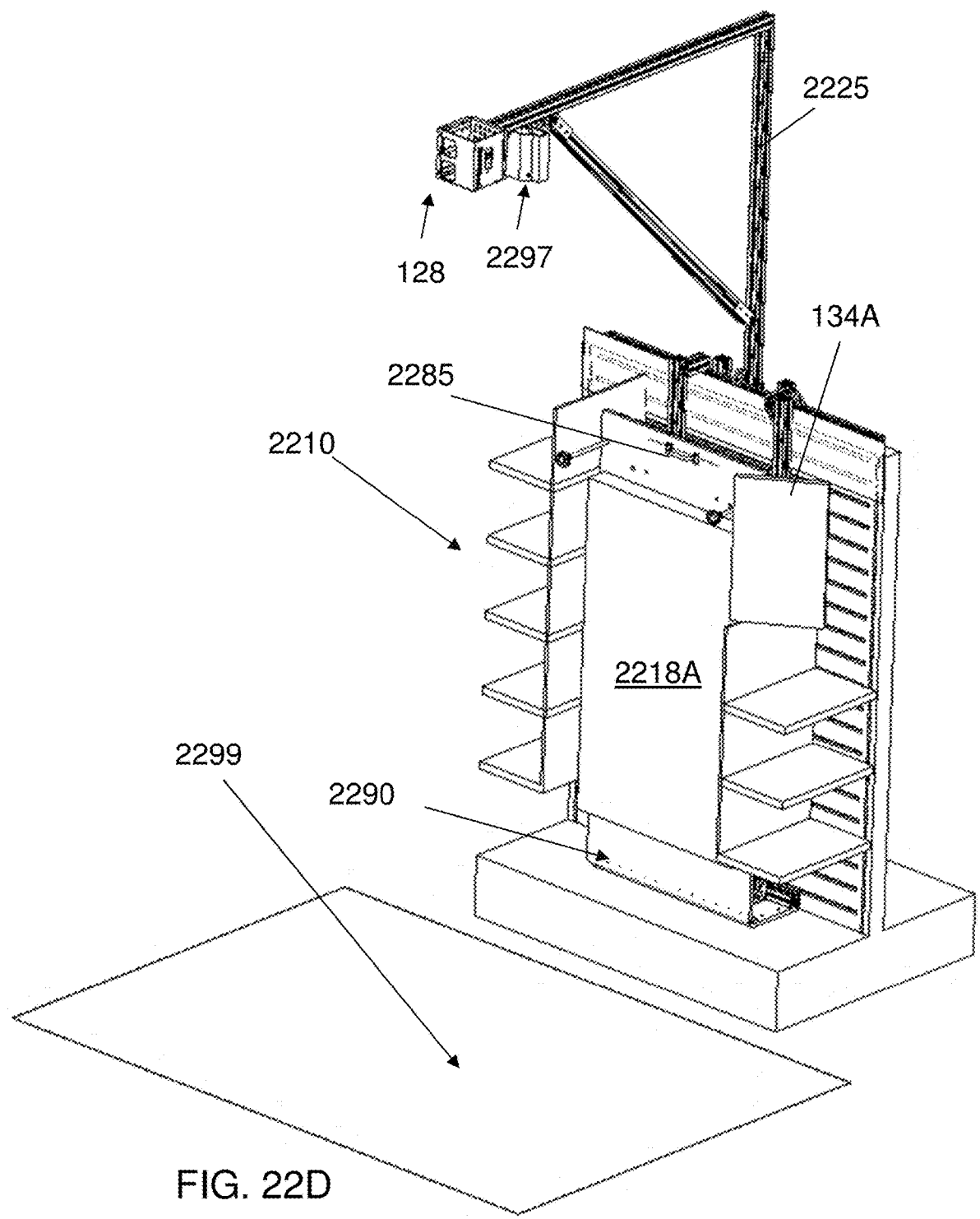
FIG. 22D illustrates a perspective view of the housing of FIG. 22C in a folded state with a projector displaying an image according to an embodiment.

FIG. 22A illustrates a perspective view of a foldable housing 2210 of the system of FIG. 1 in an unfolded state according to an embodiment. FIG. 22B illustrates a perspective back view of the housing 2210 of FIG. 22A. FIG. 22C illustrates a perspective view of the housing 2210 of FIG. 22A in a folded state according to an embodiment. FIG. 22D illustrates a perspective view of the housing 2210 of FIG. 22C in a folded state with a projector displaying an image according to an embodiment. The housing 2210 is an example kiosk housing that may be folded away when not in use.

The housing 2210 may include a plurality of legs 2280 coupled to the bottom of floor 2218. The legs 2280 support the foldable floor 2218 so that when unfolded, the floor 2218 is essentially parallel to a horizontal plane. The scale 120 is located on top of the floor 2218 or may be integrated into the floor 2218. The housing 2210 may include a hinged ramp 2213 and hinge 2221. The ramp 2213 when folded may be folded on top of the scale 120, for example. In other embodiments, the ramp 2213 may be slid under the scale in a gap between floor 2218 and the bottom surface of scale 120 to fold up the housing 2210. The hinged ramp 2213, when deployed, allows the animal to move from a ground surface to the ramp 2213 and then onto the scale 120 in the walk-in analysis zone, when the housing and the ramp are in the fully deployed position, as shown in FIG. 22A.

With reference to FIGS. 22C and 22D, the exterior surface 2218A of the floor 2218 is viewable when folded. In the folded position, the housing is stowed. The exterior surface 2218A may include advertisements.

The housing 2210 includes a back wall 2217 that has mounted thereto the support structure 2225 having a mast supporting the cameras of the vision system 128. In FIG. 22A, the support structure 2225 is upright or unfolded. As previously described in FIG. 10A, the support structure 2225 may be hingedly coupled to the housing 2210 or back wall 2217. As shown in FIG. 22B, spring balancers 2295 are mounted behind the back wall 2217. The spring balancers 2295 balance the weight of the housing and structures mounted thereto in the folded position and unfolded positions.

The housing 2210 includes a base mount 2253 and a primary upright wall (i.e., back wall 2217) mounted perpendicular to the base mount 2253. The primary upright wall has at least one camera 127 mounted thereto. The primary wall (i.e., back wall 2217) may include other sensors (not shown) of the sensor suite 115 mounted thereto. An example, persuasion delivery device (i.e., bowl 160A) and dispensing machine are shown in FIG. 11. The dispensing machine may be mounted behind back wall 2217 in an enclosure not shown. The computing device 150 (FIG. 1) may also be housing in the enclosure and in communication with user interface 134A.

The housing 2210 includes structures for a foldout analysis zone 112. The foldout analysis zone 112 includes the legs 2280 and scale 120. The foldout analysis zone 112 also includes persuasion delivery device (i.e., bowl 160A). The foldout analysis zone 112 may include other persuasion delivery devices. The housing of the foldout analysis zone 112 includes foldable side walls 2215A and 2215B. The foldable side walls 2215A and 2215B may include suspension cables 2245A and 2245B, respectively, each having coupled thereto foldable surface 2247. The foldable surface 2247 may be made of a non-rigid and flexible material, such as a cloth, vinyl, plastic, or the like. The exterior surface 2218A of the floor may include a handle 2285 which can be used to unfold the foldout analysis zone 112.

The housing 2210 may include tracks 2261 mounted in space relation along the length of the primary wall (i.e., back wall 2217). The housing 2210 may include shelves 2264 that are removably mounted to tracks 2261. The shelves 2264 may be arranged in a column along the length of the back wall to provide display shelves for placement of products for a pet. The products (not shown) may include at least one of treats, food, vitamin or nutritional supplements and other pet supplies. The other pet supplies may include grooming products and/or toy products.

With reference again to FIGS. 22C and 22D, the structures of the housing for the foldout analysis zone 112 may include hinge assembly 2290 which allows the floor 2218 and scale to be rotated from the folded position shown in FIGS. 22C and 22D to an unfolded position shown in FIGS. 22A and 22B. The user can use handle 2285 to apply a force in a direction away from the back wall 2217 to rotate the floor and scale from an upright position to a generally horizontal position. In some embodiments, the hinge assembly 2290 may include a damper hinge to provide a soft landing of the legs 2280 onto the underlying ground surface in view of the weight of the floor 2218, scale 120, etc., being lowered.

The system may include a projector 2297 mounted to the support structure 2225. When the housing is in the folded position, the projector 2297 may project a screen 2299 (FIG. 22D) on the ground.

Figure 23A:
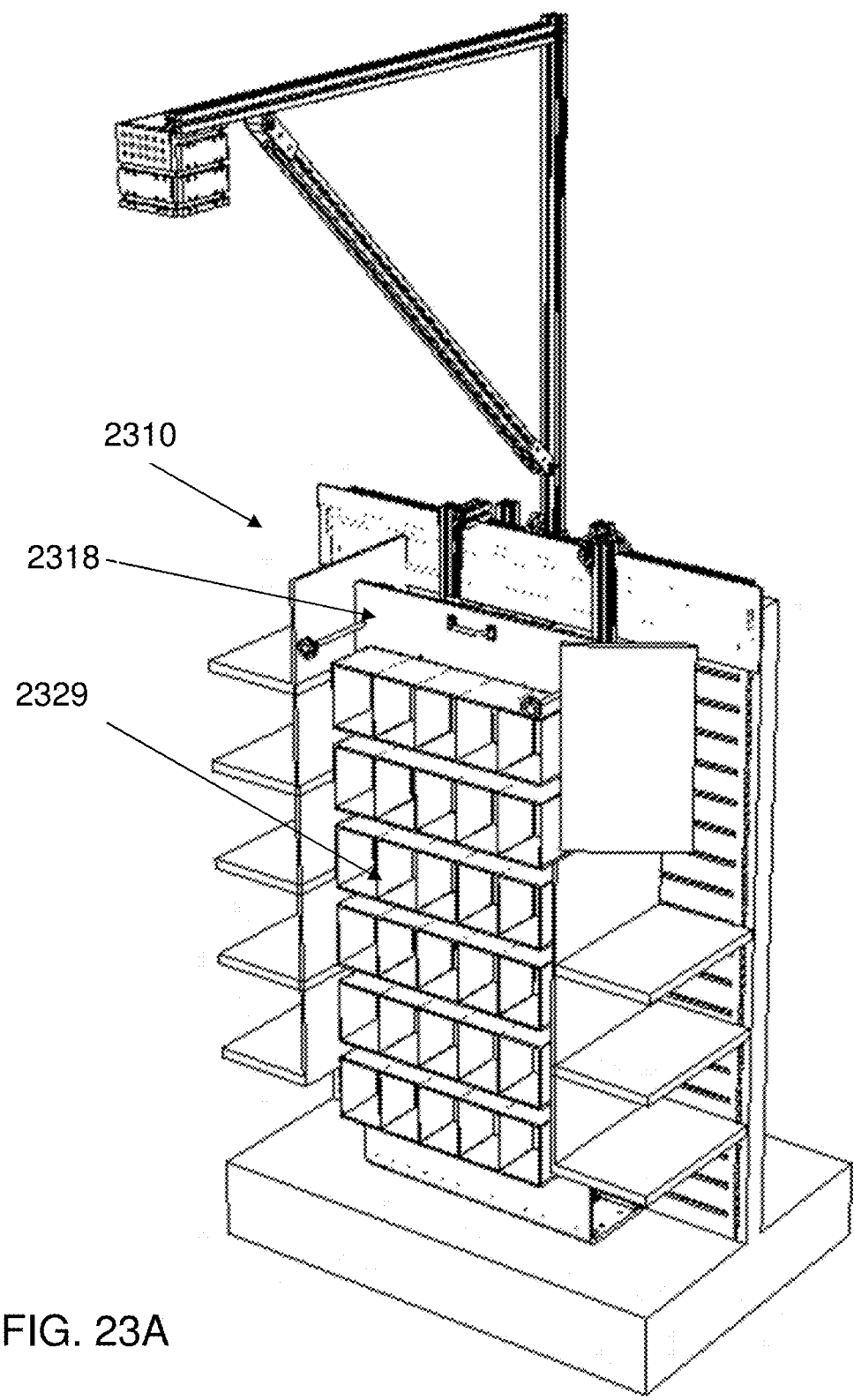
FIG. 23A illustrates a perspective view of a foldable housing of the system in a folded state according to an embodiment.
Figure 23B:
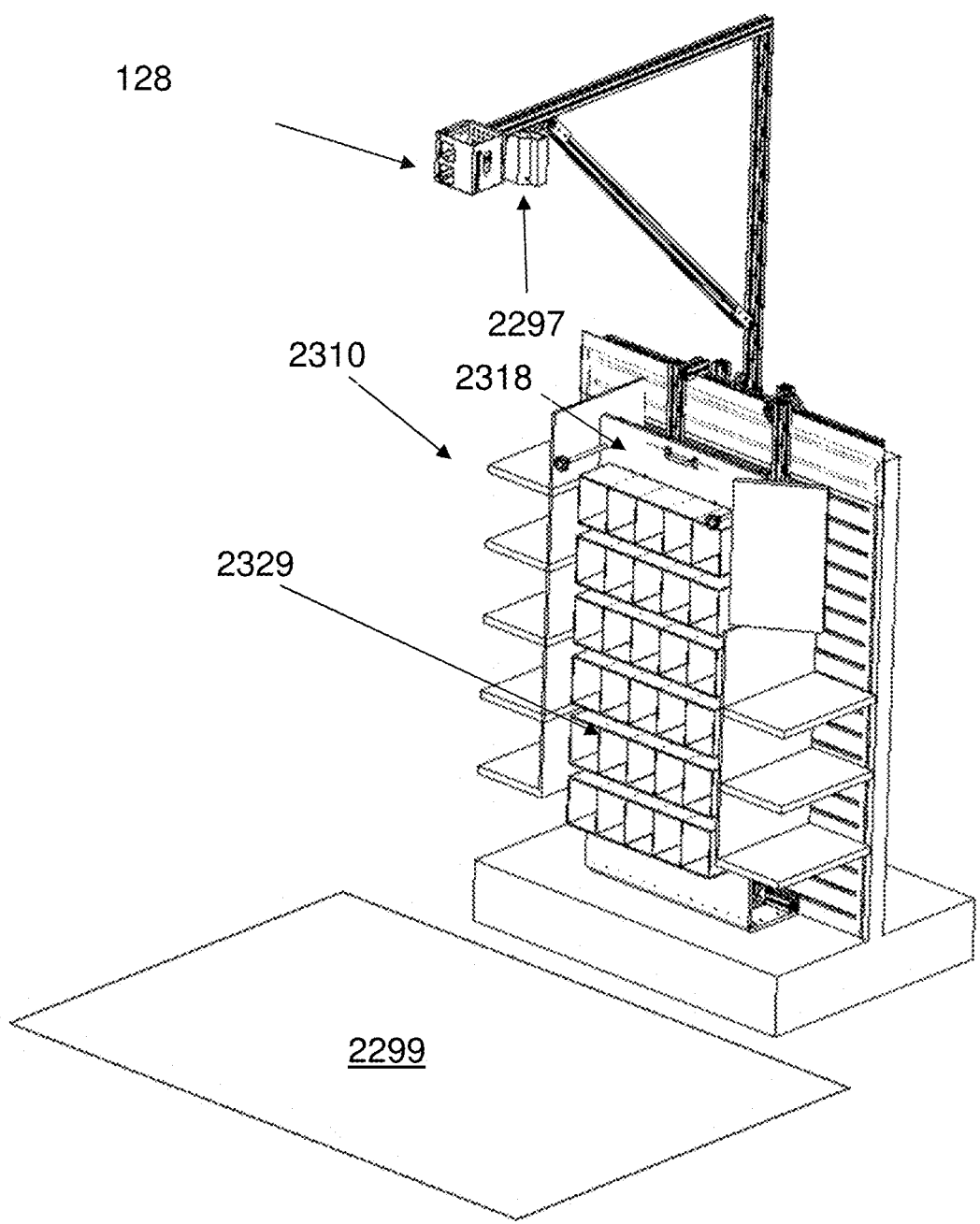
FIG. 23B illustrates a perspective view of the foldable housing of FIG. 23A in a folded state with a projector displaying a screen according to an embodiment.

FIG. 23A illustrates a perspective view of a foldable housing 2310 of the system in a folded state according to an embodiment. FIG. 23B illustrates a perspective view of the foldable housing 2310 of FIG. 23A in a folded state with a projector displaying a screen 2299 according to an embodiment. The foldable housing 2310 is essentially the same as housing 2210 of FIGS. 22A-22D. Thus, only the differences will be described in detail. The housing 2310 may include cubby shelves 2329 mounted to floor 2318. The cubby shelves 2329 may be open or covered with a transparent surface. The transparent surface may allow the contents or packages stored in the cubby shelves to be viewed when the housing is in the folded state. Moreover, in an unfolded position, such as shown in FIG. 22A, the contents of the cubby shelves is prevented from falling out of the cubby shelves. In some embodiments, the transparent surface may include a hinged door that has a transparent surface, but may be opened by rotating the door to an open position. The door may include a latching mechanism.

Figure 24:
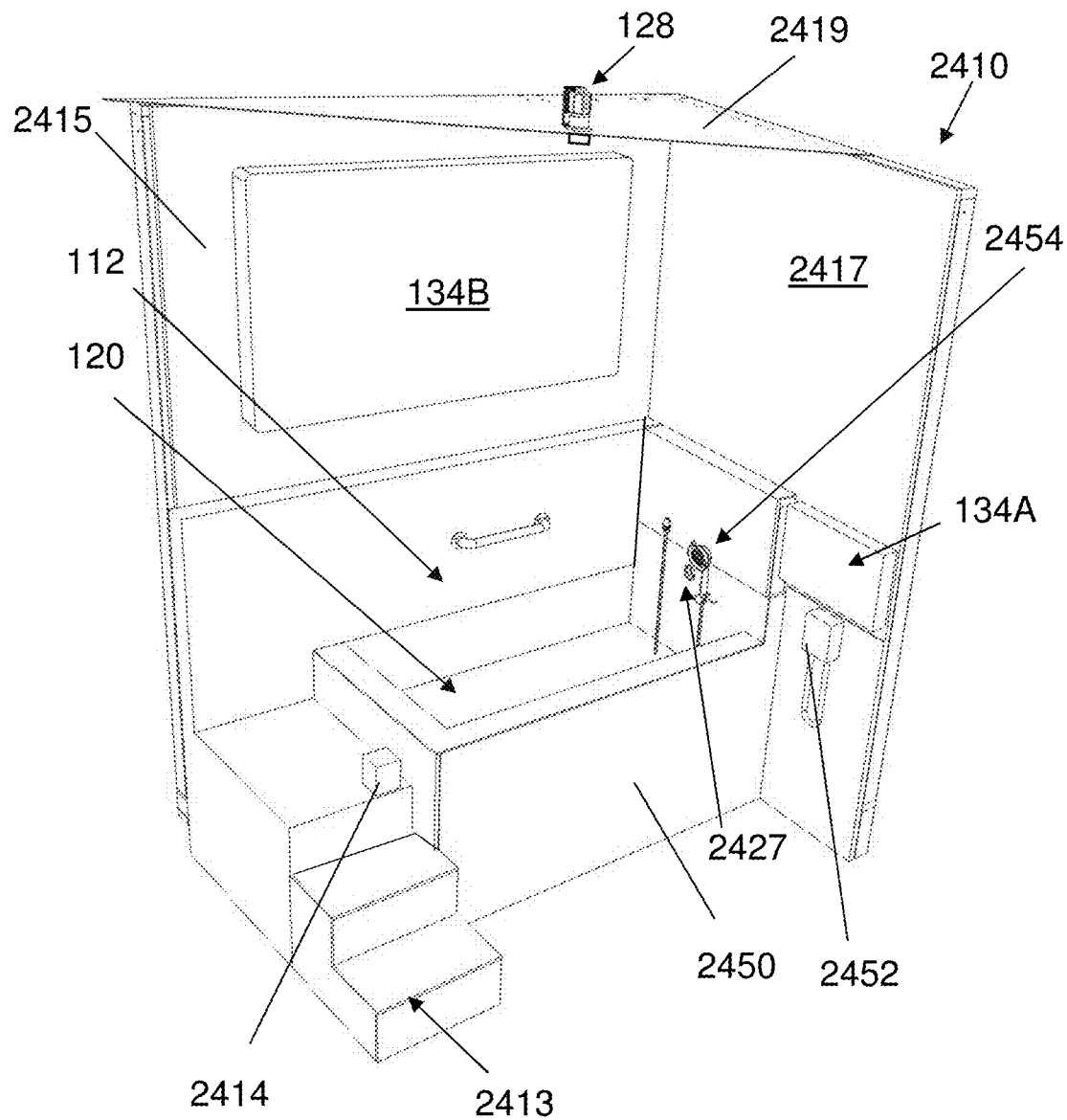
FIG. 24 illustrates a perspective view of a housing with a grooming station for the system for non-invasive animal health sensing and analysis according to an embodiment.

FIG. 24 illustrates a perspective view of a housing 2410 with a grooming station 2450 for the system for non-invasive animal health sensing and analysis according to an embodiment. The housing 2410 will be described in relation to system 100 of FIG. 1. To prevent overcrowding of the figure, only the features of the housing will be described in detail. The housing 2410 may include stairs 2413 to the grooming station 2450 and a sensor 2414. The sensor 2414 may be at the top of the stairs 2413 to detect an ID signal from the animal or other signal to detect entry into the analysis zone 112. The housing 2410 supports camera 2427 on the back wall 2417. The side wall 2415 has mounted thereto the user interface 134B. In this example the user interface 134A is mounted to back wall 2417.

The analysis zone 112 includes scale 120 which is integrated into the grooming station 2450, as will be described in more detail in relation to FIG. 27. The grooming station 2450 resembles a bathtub to provide washing of an animals hair. The grooming station may allow the animals hair to be cut and/or dried at the grooming station. In operation, prior to washing the animal or grooming the animal, the weight of the animal may be measured by the scale 120 and stored in the client's file. The housing may provide mounts for supporting and/or providing power to grooming tools 2452, such as a hair drier, hair cutting tool, scrub brush, etc. For example, the grooming tool 2452 may be a scrub brush which also receives water from a water source (not shown). The scrub brush may be activated to receive water to wet the pet as the pet is washed, for example. In some embodiments, the scrub brush may receive a mixture of water and soap, in one mode to wash the pet. The scrub brush may deliver only water when rinsing the animal. The grooming station may include other grooming tools 2454 within the analysis zone 112. For example, grooming tool 2454 may be a water hose and shower heat to wet or rinse the animal. The grooming tool 2454 is shown mounted to the back wall 2417. Nonetheless, the grooming tools may be mounted at other locations in the housing for convenience of use and application of the water, for example.

Over the analysis zone, the housing includes a cover or lid 2419 which has mounted thereto cameras of the vision system 128, for example. However, other support structures may be used to position cameras of the vision system 128 over the analysis zone. In some embodiments, the housing 2410 and other housings described herein may connect to a public utilities or provide its own source of public utilities. For example, public utilities include electricity and/or water. However, the housing 2410 may provide storage space for batteries to provide electricity and water tanks for supplying water to the grooming station. The housing 2410 may include storage containers (not shown) for the soap.

The persuasion delivery device may include a speaker or orifice (not shown) in the analysis zone, such as in proximity to the camera 2427 or at another location. The dispensing machine would be located behind back wall 2417.

Figure 25:
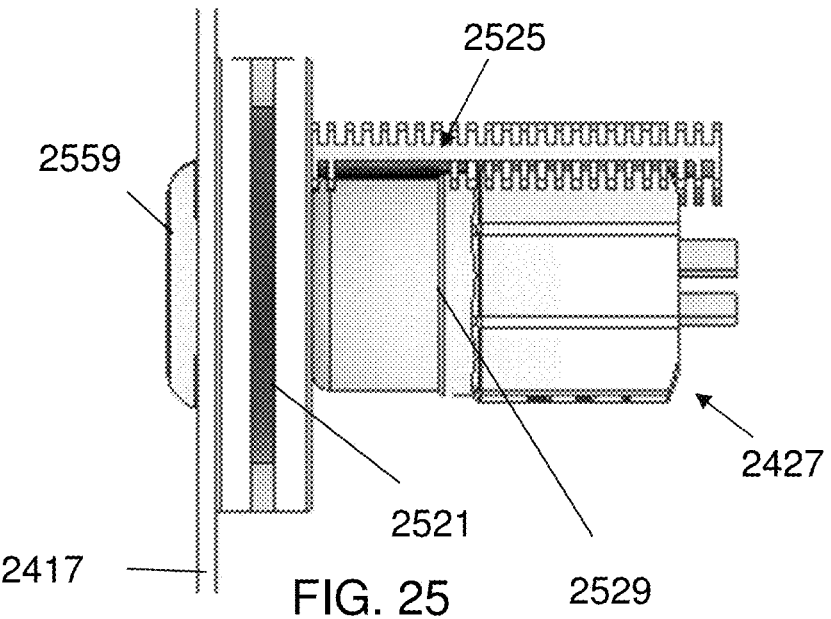
FIG. 25 illustrates a side view of a camera according to an embodiment.

FIG. 25 illustrates a side view of a camera 2427 according to an embodiment mounted to a back wall (i.e., back wall 2417) of housing 2410. It should be understood that the camera 2427 may be installed in any of the side walls and back wall any of the housings as described herein to obtain multiple views of the animal. The camera 2427 may also be installed in the floor of any of the housings, such that the lens has a field of view of the underside of the animal in the analysis zone. The camera 2427 may be mounted to a camera mount adaptor 2521 affixed to the back wall. The camera 2427 may be mounted on a rail 2525 that is coupled to the camera mount adaptor 2521. The rail, such as a picatinny rail, allows the camera's placement to be adjusted relative to the wall. The camera body 2529 includes notches to mate with notches of the rail 2525. The camera body 2529 may be connected to the lens housing ring 2559 and lens 2639 (FIG. 26A).

Figure 26A:
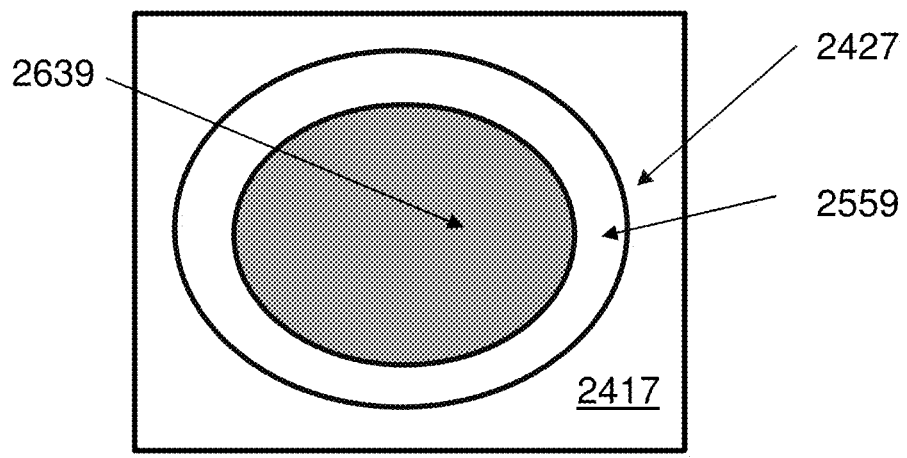
FIG. 26A illustrates a front view of the camera of FIG. 25 with the camera lens in an open state.
Figure 26B:
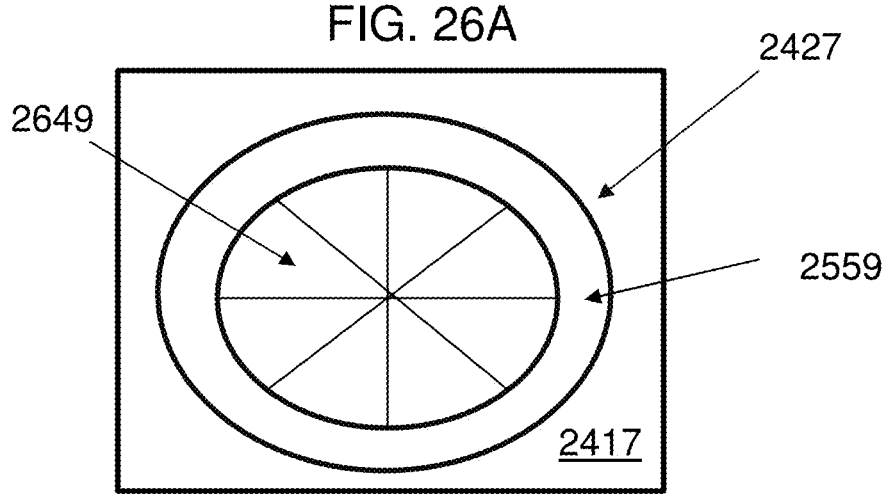
FIG. 26B illustrates a front view of the camera of FIG. 25 with the camera lens in a closed state covered by a shutter.

FIG. 26A illustrates a front view of the camera 2427 of FIG. 25 with the camera lens 2639 in an open state. The lens 2639 is recessed in lens housing ring 2559. In the open state, the shutter 2649 is open and not seen. FIG. 26B illustrates a front view of the camera 2427 of FIG. 25 with the camera lens 2639 in a closed state covered by a shutter 2649. In the closed state, the lens may be protected by the shutter.

Figure 27:
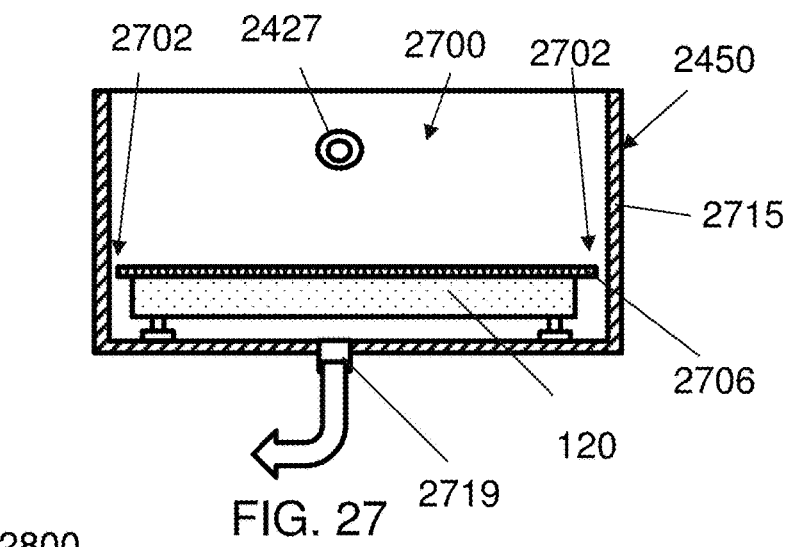
FIG. 27 illustrates a cross-sectional view of the grooming station according to an embodiment.

FIG. 27 illustrates a cross-sectional view of the grooming station 2450 according to an embodiment. The groom station 2450 is a bathtub 2700. In the bathtub 2700, the scale 120 is provided such that gaps 2702 are formed between an upper surface 2706 of the scale 120 and side walls 2715 of the bathtub 2700. The gaps 2702 are drains which allow water to flow off of the upper surface 2706 and to the bottom of the bathtub 2700 where the drain 2719 removes the water from the bathtub 2700. The drain may be connected to a spent water tank (not shown) or public utilities. At least one side of the bathtub 2700 may include the camera 2427. However, the bathtub 2700 may have other cameras installed on other sides that face the lens in the direction of the scale.

In some instances, the grooming station 2450 may be used to cut the hair of an animal. In this instance, the drains 2702 allow the hair to fall to the bottom of the bathtub 2700 which may be later removed and discarded between clients. The housing may have an access panel (not shown) to the area of the bathtub 2700 below the scale 120 so that the bottom of the tub may be cleaned, sterilized or vacuumed to remove hair or other debris. The access panel may be located on side wall 2415 or back wall 2417 or the front surface of the bathtub.

FIGS. 28-35 are example graphical user interfaces that may be displayed on at least one user interface 134A and 134B (FIG. 1). One or more of the graphical user interfaces may be displayed on owner's mobile device 50 or other personal computing device, shown in FIG. 18. The graphical user interfaces of FIGS. 28-35 will be described in relation to FIG. 1.

Figure 28:
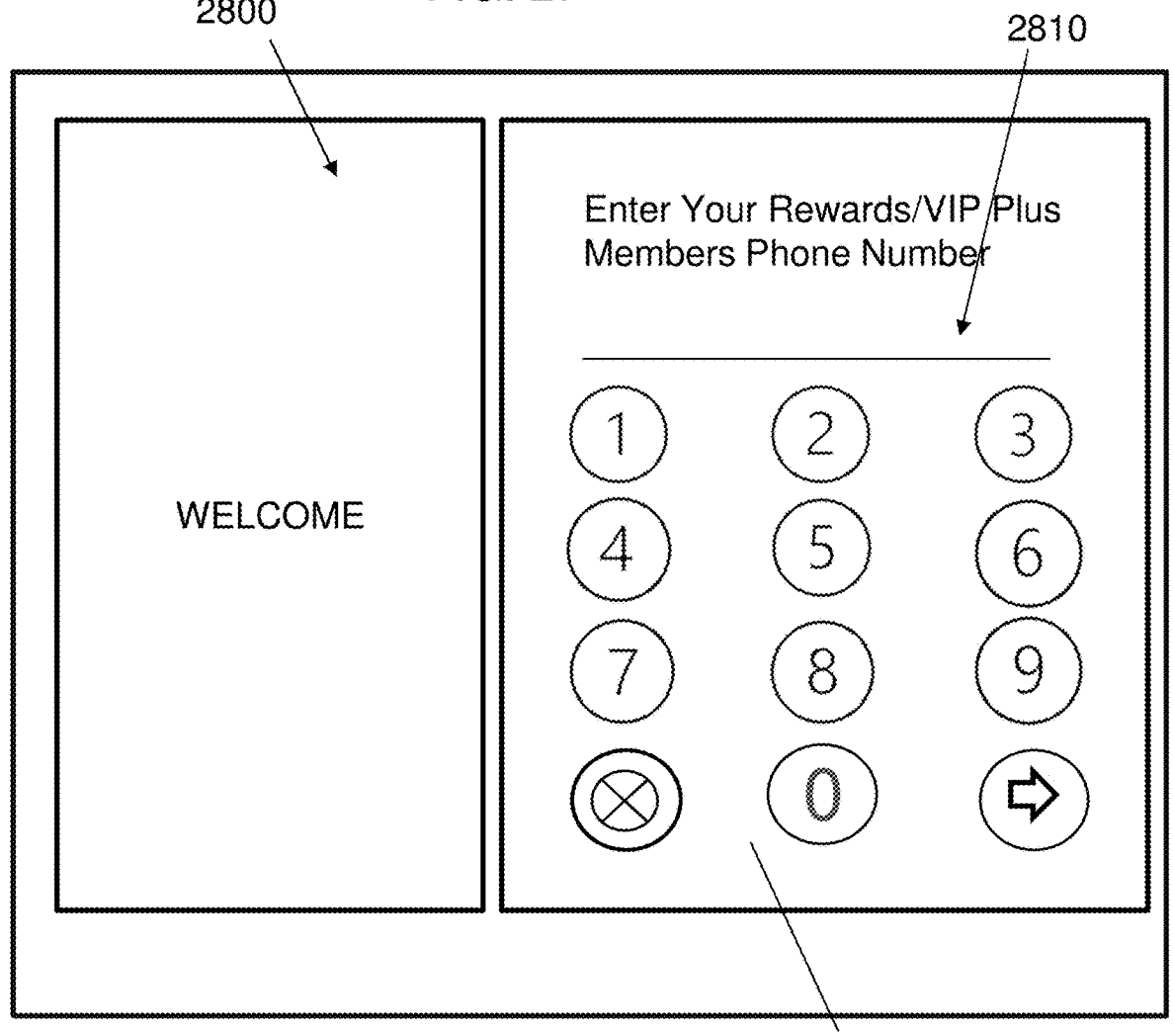
FIG. 28 illustrates a login graphical user interface.

FIG. 28 illustrates a login graphical user interface (GUI) 2800. The login GUI 2800 includes a data entry field 2810 for entering a phone number of the owner or other identifier. For example, instead of a phone number an email address may be used. The login GUI 2800 may include a key pad 2820. In some embodiments, the key pad 2820 may be a touch key pad provided the display device used to display the key pad 2820 includes a touch sensitive display. Other data entry mechanisms may be used to enter owner name. In some embodiments, detection of the ID signal may be sufficient to automatically login the owner and animal.

The login GUI 2800 may be displayed on both user interfaces 134A and 134B. However, the owner may use graphical user interface 134A to enter the data. Once the data is verified or authenticated, the GUI 2800 may automatically navigate to one or more graphical user interfaces, such as a welcome graphical user interface 2900. Entering the login data may cause dispensing of at least one animal attractant 137.

Figure 29:
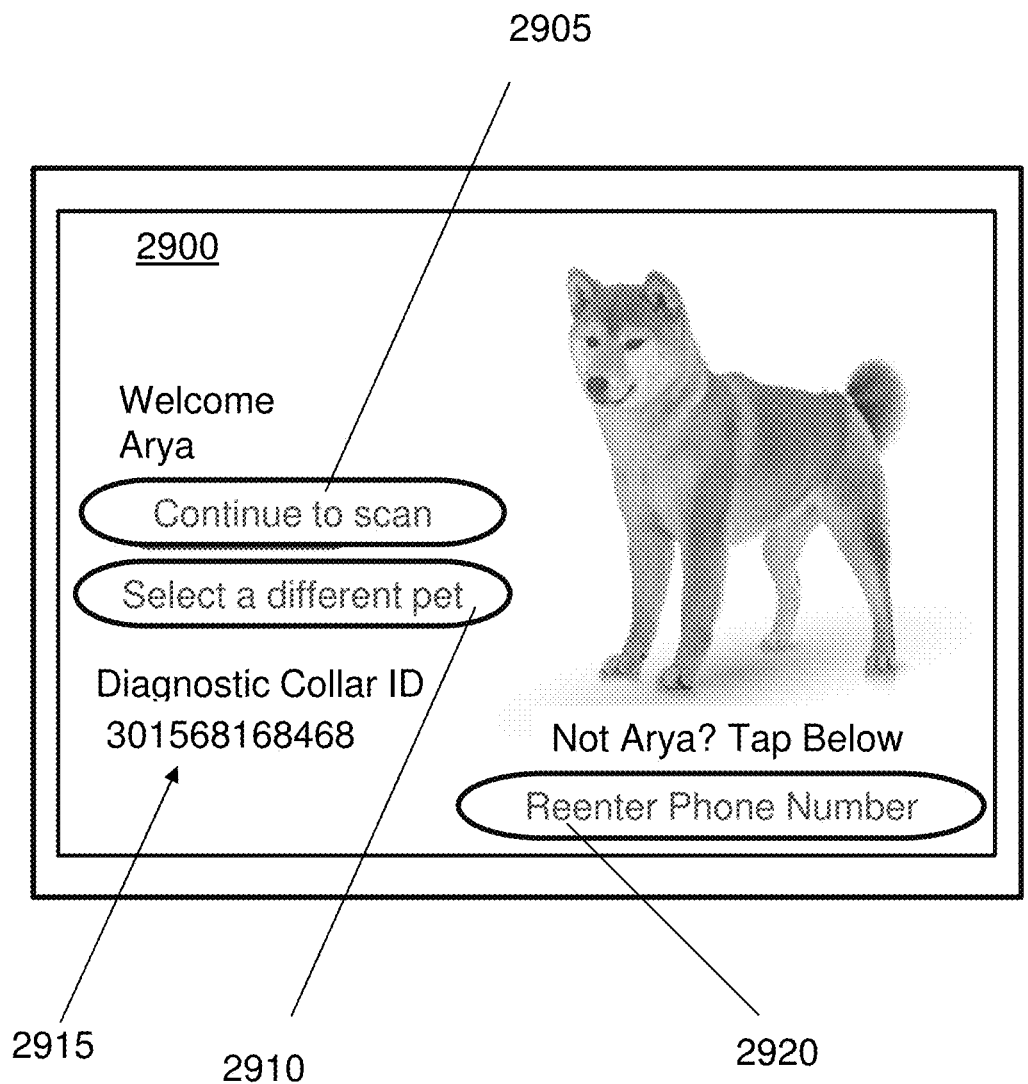
FIG. 29 illustrates a welcome graphical user interface.

FIG. 29 illustrates a welcome graphical user interface (GUI) 2900. The welcome GUI 2900 may include one or more buttons 2905, 2910 and 2920 to control navigation through the graphical user interfaces. For example, button 2905 may allow the owner to start the scan and/or data acquisition of the animal using the sensor suite 115 in the analysis zone. The owner may have client files 152 for more than one pet. The welcome GUI 2900 may confirm which pet is being scanned or analyzed by selecting button 2920. The welcome GUI 2900 may display a collar ID in field 2915, which may have been detected by T&ID senor 122 or from orientation indicator device (i.e., collar 1900 in FIG. 19A). The button 2910 may be selected for the owner to select a different pet for examination (i.e., scanned and/or analyzed) using a different graphical user interface. The welcome GUI 2900 may display an image of the pet associated with the collar ID in field 2915 or other ID.

Figure 30:
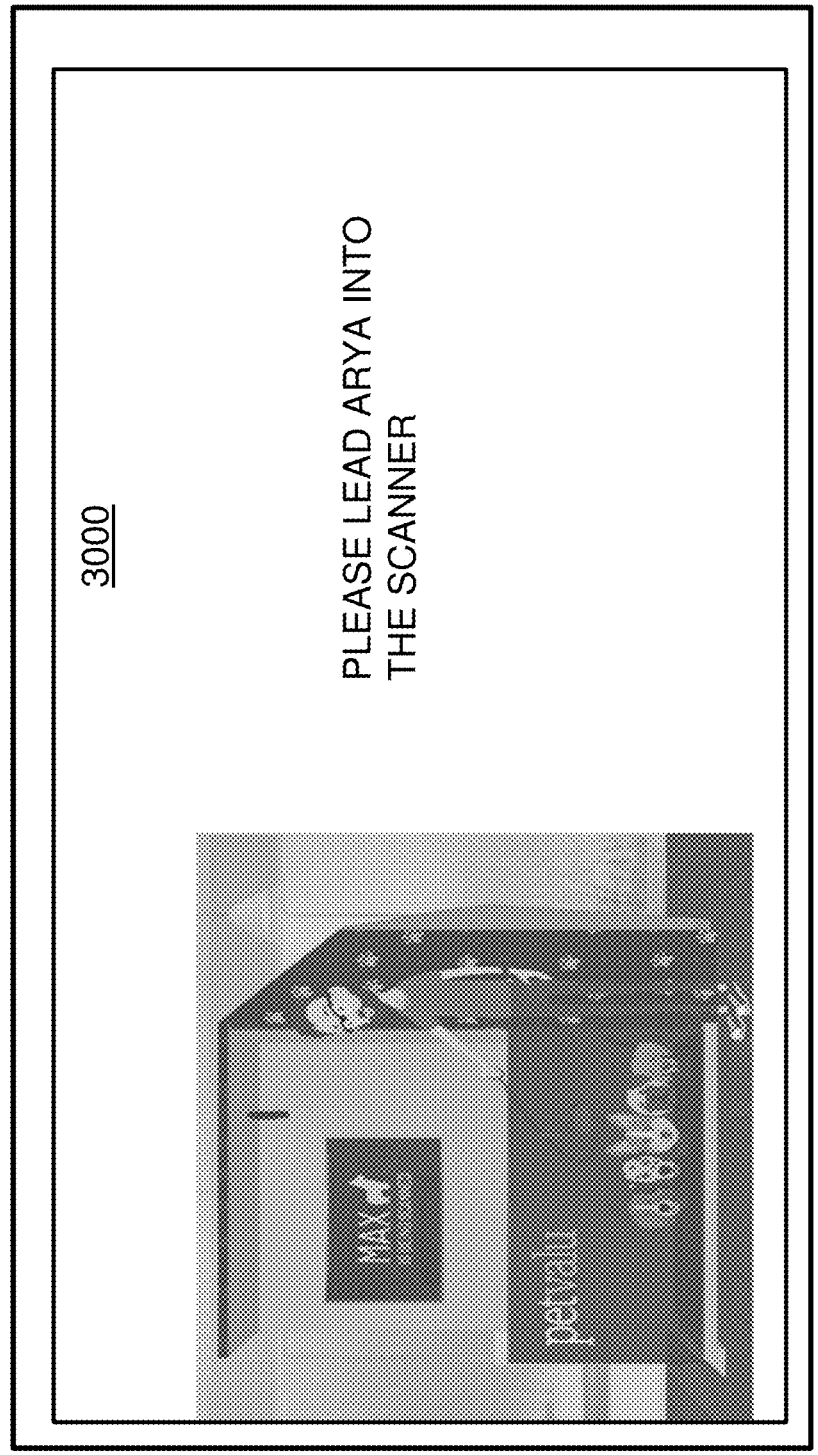
FIG. 30 illustrates an instructional graphical user interface.

FIG. 30 illustrates an instructional graphical user interface (GUI) 3000. The instructional GUI 3000 may provide instruction to the owner such as how to lead the pet into the analysis zone.

Figure 31:
FIG. 31 illustrates a thank you graphical user interface.

FIG. 31 illustrates a thank you graphical user interface (GUI) 3100 indicating the session is complete.

Graphical user interfaces of FIGS. 32-35 are shown displayed on an owner's mobile device. However, the graphical user interfaces of FIGS. 32-35 may be displayed on display screens of user interfaces 134A and/or 134B using navigation through user interface 134A, for example. The owner may navigate through the graphical user interfaces using a swiping left or right action on a display screen of the mobile device. Other navigation controls may be used. The system includes graphical user interfaces to display any of the acquired data in a graphical user interface with current data, previous data, if available, and a comparison. The comparison may include data related to at least one of: current data and previous data; and breed or clinical data and current data.

Figures 32, 33:
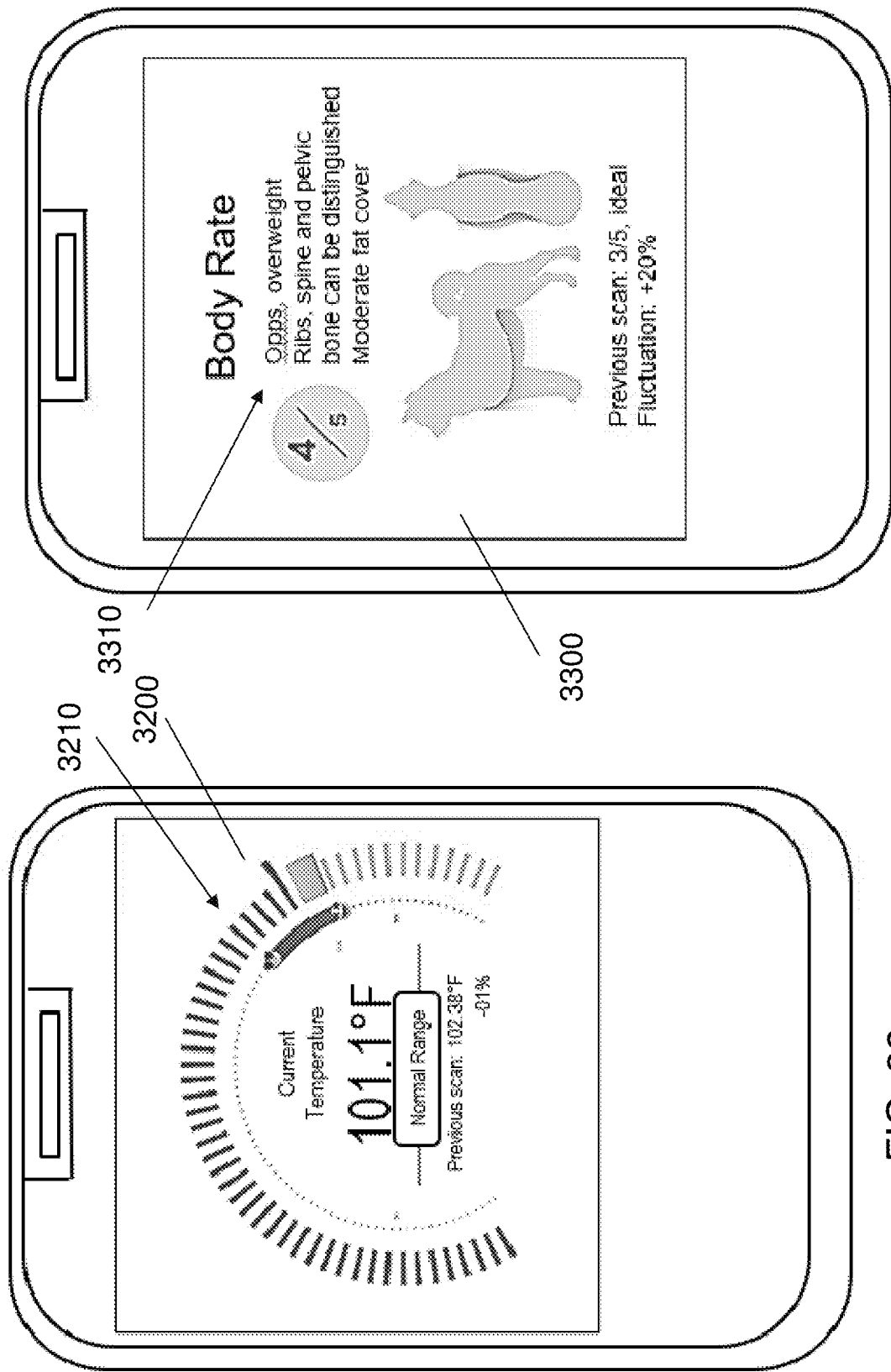
FIG. 32 illustrates a temperature indicator graphical user interface.
FIG. 33 illustrates a body rate indicator graphical user interface.

FIG. 32 illustrates a temperature indicator graphical user interface (GUI) 3200. The temperature indicator GUI 3200 includes a dial 3210 representing a thermostat or temperature gauge. The center of the dial 3210 may include the actual measured temperature and other breed or clinical information, such as whether the temperature is normal, high or low. The GUI 3200 may include previous temperature data and a percentage of change.

FIG. 33 illustrates a body rate indicator graphical user interface (GUI) 3300. The body rate indicator GUI 3300 may include data 3310 that includes comparison data, fluctuations from past reading, and images representative of the body rate, such as whether the animal has an ideal weight, obese, overweight, etc.

Figure 34:
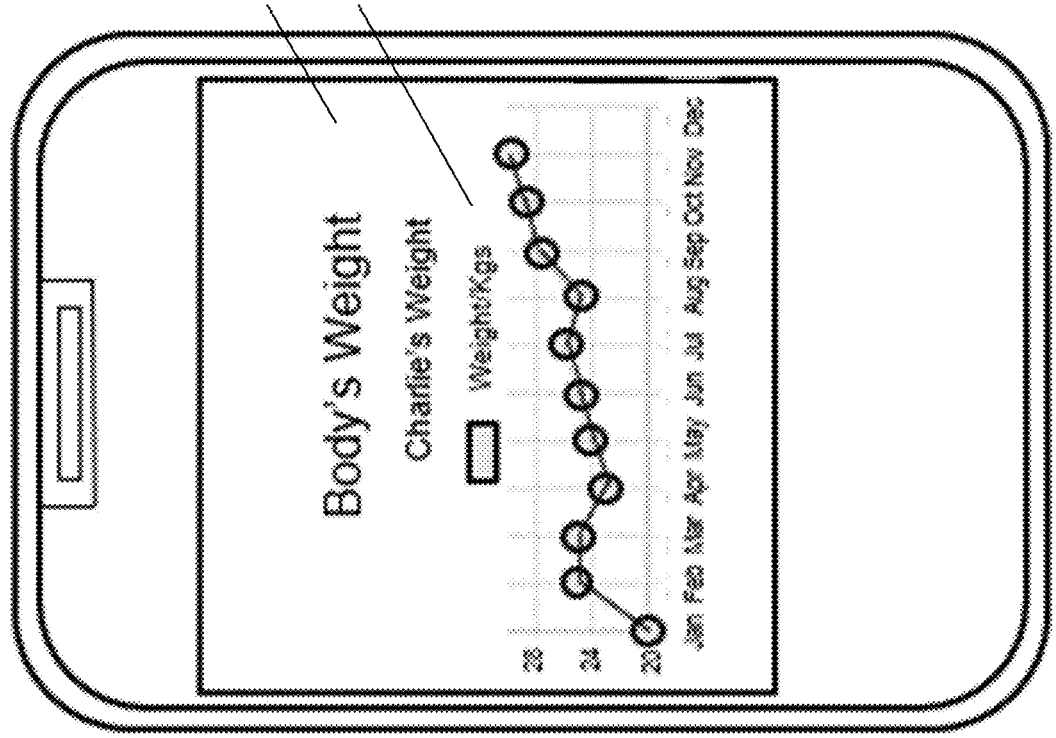
FIG. 34 illustrates a body weight log graphical user interface.

FIG. 34 illustrates a body weight log graphical user interface (GUI) 3400. The body weight log GUI 3400 may include a graph 3410 representative of the current and previous weights taken. In this example, the weights were taken each month for a year. However, other measurement intervals may be used based on the frequency of the examination of the animal. The graph 3410 is a representation of a comparison of the weights of the animal being communicated to the owner.

Figure 35:
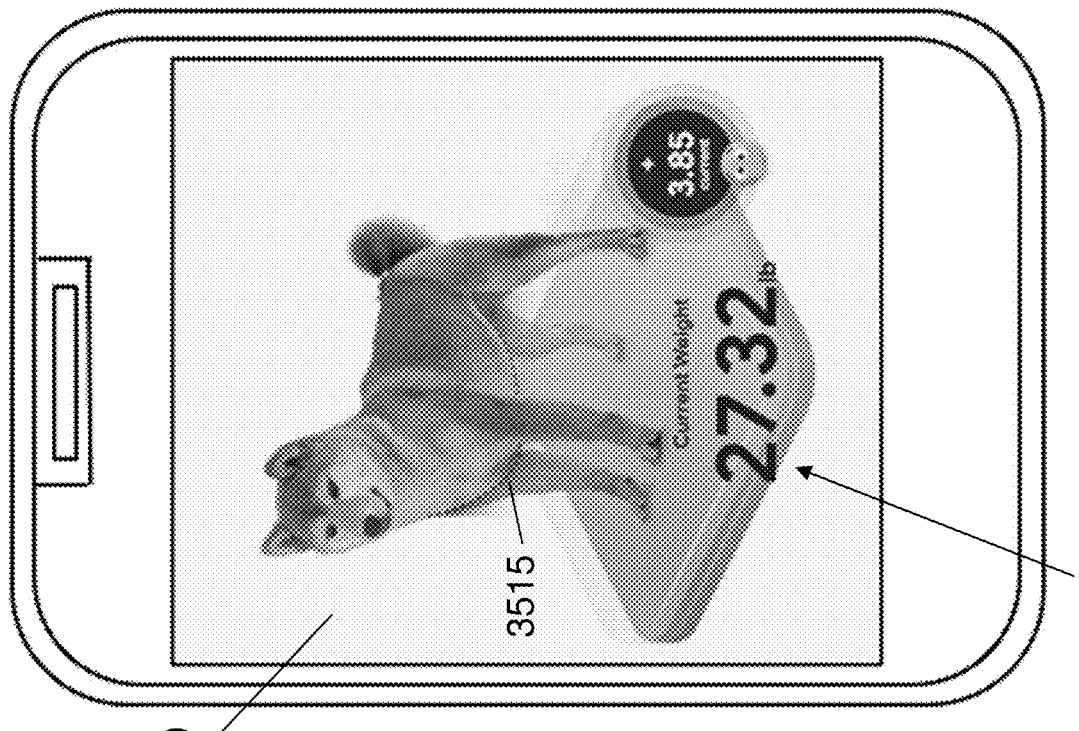
FIG. 35 illustrates a current weight indicator graphical user interface.

FIG. 35 illustrates a current weight indicator graphical user interface (GUI) 3500. The current weight indicator GUI 3500 includes an icon of a scale with the current weight 3510 displayed in the GUI 3500. The GUI 3500 may include an image of the actual pet or other pet icon or avatar. In some embodiments, the actual pet image may include overlaid outline 3515 of the belly and chest of the animal. The GUI 3500 may display information related to a comparison of the current weight and the previous weight. In this example, the weight is up 3.85 pounds (lbs.).

The system 100 may include other graphical user interfaces to display the acquired images shown in FIGS. 15A, 15B, 16B and 17. The graphical user interfaces may display heart rate, breathing rate, breath vapor data, vital signs and more. Similar to FIGS. 33, 34 and 34, any biological data and vital signs measured may be displayed using a current data GUI, such as GUI 3500, historical data GUI, such as GUI 3400, and a clinical or breed analysis data GUI, such as GUI 3300.

The system may display information associated with a dental condition, eye condition, growths, and/or ailments.

The computing device 1800 may carry out one or more blocks/steps of processes in FIGS. 7A, 7B, 8A-8C, 9A, 20 and 21 described herein. The computing device 1800 may also have additional features or functionality. As a non-limiting example, the computing device 1800 may also include additional data storage media devices 1808 (removable and/or non-removable) such as, for example, magnetic disks, optical disks, or tape. The computer storage media devices 1808 may include volatile and non-volatile, non-transitory, removable, and non-removable media implemented in any method or technology for storage of data, such as computer readable instructions, data structures, program modules or other data. The system memory, removable storage and non-removable storage are all non-limiting examples of computer storage media. The computer storage media may include, but is not limited to, RAM 1802, ROM 1804, Electrically Erasable Read-Only Memory (EEPROM), flash memory or other memory technology, compact-disc-read-only memory (CD-ROM), digital versatile disks (DVD) or other optical storage, magnetic cassettes, magnetic tape, magnetic disk storage or other magnetic storage devices, or any other physical medium which can be used to store the desired data and which can be accessed by computing device. Any such computer storage media may be part of device.

The computing device 1800 may also include or have input/output (I/O) interfaces 1812 for input modules 1864 such as a keyboard, mouse, pen, voice input device, touch input device, etc. The computing device may include or have I/O interfaces 1812 for connection to output device(s) such as a display, a presentation module 1816, speakers, etc. A graphical user interface (GUI) 1818 may be displayed on the presentation module 816. The computing device 1800 may include a peripheral bus 1824 for connecting to peripherals. Computing device 1800 may contain communication connection(s) that allow the device to communicate with other computing devices, such as over a network or a wireless network. By way of example, and not limitation, communication connection(s) may include wired media such as a wired network or direct-wired connection, and wireless media such as acoustic, radio frequency (RF), infrared and other wireless media. The computing device 1800 may include a network interfaces 1820, such as a network interface card to connect (wired or wireless) to a network or other communication conduits 1822 to the cloud computing system.

Computer program code for carrying out operations described above may be written in a variety of programming languages, including but not limited to a high-level programming language, such as C or C++, Python, Java, for development convenience. In addition, computer program code for carrying out operations of embodiments described herein may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed Digital Signal Processor (DSP) or microcontroller. A code in which a program of the embodiments is described can be included as a firmware in a RAM, a ROM, and a flash memory. Otherwise, the code can be stored in a tangible computer-readable storage medium such as a magnetic tape, a flexible disc, a hard disc, a compact disc, a photo-magnetic disc, and a digital versatile disc (DVD).

The embodiments may be configured for use in a computer or a data processing apparatus which includes a memory, such as a central processing unit (CPU), a RAM and a ROM as well as a storage medium such as a hard disc.

The "step-by-step process" for performing the claimed functions herein is a specific algorithm, and may be shown as a mathematical formula, in the text of the specification as prose, and/or in a flow chart. The instructions of the software program create a special purpose machine for carrying out the particular algorithm. Thus, in any means-plus-function claim herein in which the disclosed structure is a computer, or microprocessor, programmed to carry out an algorithm, the disclosed structure is not the general-purpose computer, but rather the special purpose computer programmed to perform the disclosed algorithm.

A general-purpose computer, or microprocessor, may be programmed to carry out the algorithm/steps for creating a new machine. The general-purpose computer becomes a special purpose computer once it is programmed to perform particular functions pursuant to instructions from program software of the embodiments described herein. The instructions of the software program that carry out the algorithm/steps electrically change the general-purpose computer by creating electrical paths within the device. These electrical paths create a special purpose machine for carrying out the particular algorithm/steps.

Unless otherwise defined, all terms (including technical and scientific terms) used herein have the same meaning as commonly understood by one of ordinary skill in the art to which embodiments belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In particular, unless specifically stated otherwise as apparent from the discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such data storage, transmission or display devices.

"Communication media" typically comprise computer readable instructions, data structures, program modules, or other data in a modulated data signal, such as carrier wave or other transport mechanism. The communication media may also comprise any information delivery media. The term "modulated data signal" means a signal that has one or more of its characteristics set or changed in such a manner as to encode information in the signal. By way of example, and not limitation, communication media comprises wired media such as a wired network or direct-wired connection, and wireless media such as acoustic, infrared, and other wireless media. Combinations of any of the above are also included within the scope of computer readable medium.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order or importance, but rather the terms first, second, etc., are used to distinguish one element from another. As used herein the expression "at least one of A and B," will be understood to mean only A, only B, or both A and B.

While various disclosed embodiments have been described above, it should be understood that they have been presented by way of example only, and not limitation. Numerous changes, omissions and/or additions to the subject matter disclosed herein can be made in accordance with the embodiments disclosed herein without departing from the spirit or scope of the embodiments. Also, equivalents may be substituted for elements thereof without departing from the spirit and scope of the embodiments. In addition, while a particular feature may have been disclosed with respect to only one of several implementations, such feature may be combined with one or more other features of the other implementations as may be desired and advantageous for any given or particular application. Furthermore, many modifications may be made to adapt a particular situation or material to the teachings of the embodiments without departing from the scope thereof.

What is claimed is:

1. A system comprising:
a kiosk housing having an analysis zone;
a persuasion delivery device in the analysis zone;
a dispensing machine to dispense an animal attractant to the persuasion delivery device; and
a set of sensors located in the analysis zone to sense real-time data related to health of an animal, the set of sensors includes at least one sensor to sense within the analysis zone at least one biological parameter of the animal related to the health, wherein the at least one biological parameter comprises a breath vapor, a breathing pattern, a breathing rate, a temperature, a heartbeat, a dental condition, a weight, and an eye condition, and wherein the set of sensors further comprises:
a first microphone to capture breathing data of the animal to determine the breathing rate;
a second microphone in proximity to the persuasion delivery device to capture the heartbeat of the animal;
a gas analyzer to sense the breath vapor in proximity to the persuasion delivery device; and
a camera to capture images of the animal, the captured images are associated with the dental condition or the eye condition of the animal.

2. The system of claim 1, wherein:
the persuasion delivery device includes a bowl mounted to the housing at one end of the analysis zone, the bowl includes a bowl cavity;
the animal attractant includes an animal treat; and the dispensing machine includes a treat dispensing chute to dispense an animal treat to the bowl.

3. The system of claim 1, wherein:
the persuasion delivery device includes a speaker and an orifice; and
the animal attractant includes sound dispensed through the speaker and smell dispensed through the orifice;
wherein the dispensing machine includes a computing device connected to the speaker and a diffuser coupled to the orifice.

4. The system of claim 1, further comprising:
a feed making machine to make feed for the animal.

5. The system of claim 4, wherein the feed making machine comprises:
a plurality of feed ingredients;
a mixer to mix selected ingredients of the plurality of ingredients; and
a feed pellet maker to make pellets from the mixed ingredients.

6. The system of claim 1, wherein the housing comprises:
a back wall at an end of the analysis zone;
a first side wall perpendicular to the back wall; and
a second side wall perpendicular to the back wall and parallel to the first side wall.

7. The system of claim 6, wherein the second side wall comprises a leash slot or leash ledge to place a leash attached to the animal entering the analysis zone of the housing, wherein force from the leash guides the animal into the analysis zone.

8. The system of claim 6, wherein:
the housing is foldable to an unfolded position, which allows the animal to enter the analysis zone and in a folded position, the housing is stowed, wherein the housing is alterable between the folded position and the unfolded position via one or more hinges.

9. The system of claim 8, wherein the housing further comprises shelves for at least one of displaying merchandise and storing supplies, wherein the shelves are configured in a column along a length of the back wall.

10. The system of claim 8, further comprising:
a computing device coupled to the set of sensors; and
at least one user interface having display device coupled to the computing device and the housing, the at least one user interface to display information representative of the sensed data,
wherein the display device is mounted to the housing at a viewing location.

11. The system of claim 10, wherein the camera of the set of sensors is further configured to capture data representative of a face of the animal, the camera is mounted to the housing in proximity to the persuasion delivery device in the analysis zone.

12. The system of claim 11, wherein the set of sensors comprises a computer vision system that comprises at least one camera, the at least one camera includes:
at least one infrared (IR) or thermal camera to capture at least a temperature of a body the animal; and
at least one red, green, blue (RGB) camera.

13. The system of claim 10, wherein:
the housing comprises a floor; and
the set of sensors comprises a scale integrated or embedded in the floor.

14. The system of claim 1, further comprising:
a tracking and identification (T&ID) sensor at a location entering the housing to receive a communication of an identification (ID) signal emitted from a device associated with the animal and sense an ID of the animal; and
a computing device coupled to the T&ID sensor, the set of sensors, and the dispensing machine,
wherein in response to identifying the sensed ID, the computing device controls the dispensing machine to dispense the animal attractant.

15. The system of claim 1, wherein:
the housing comprises a grooming station; and
the set of sensors comprises a scale integrated or embedded in the grooming station.

16. The system of claim 15, wherein the grooming station comprises a bathtub.

17. A method for monitoring at least one biological parameter of an animal, the method comprising:
dispensing the animal attractant by the system of claim 1, in the analysis zone;
autonomously guiding the animal to the analysis zone, having the set of sensors, by a predisposition of the animal to hunt for the animal attractant;
electronically sensing the at one biological parameter of the animal by the set of sensors in the analysis zone, the at least one biological parameter related to the health of the animal, wherein the at least one biological parameter comprises the heartbeat, the dental condition, the weight, and the eye condition; and
providing information associated with the at least one biological parameter;
wherein the persuasion delivery device includes a bowl that comprises a bowl cavity, and the sensing of the at least one biological parameter of the animal includes at least one of:
capturing images of a mouth of the animal by an imaging device within the bowl cavity as the animal eats a treat from the bowl; and
capturing images of teeth of the animal by the imaging device as the animal eats the treat from the bowl,
wherein the providing information associated with the at least one biological parameter includes providing information representative of at least one of the teeth of the animal and the mouth of the animal.

18. The method of claim 17, wherein the sensing of the at least one biological parameter of the animal further includes:
sensing, by the first microphone, breathing data of the animal to determine the breathing rate;
sensing, by the second microphone in proximity to the bowl, the heartbeat of the animal;
sensing, by the gas analyzer, the breath vapor; and
capturing, by the imaging device, images of the animal, the captured images are associated with the dental condition and eye condition of the animal,
wherein the providing information associated with the at least one biological parameter further includes providing information representative of at least one of the breathing rate, the breath vapor, one or more growths, and one or more other ailments of the animal.

19. The method of claim 17, further comprising:
sensing by a scale of the set of sensors in the analysis zone the weight of the animal,
wherein the providing information associated with the at least one biological parameter further includes providing information representative of the weight of the animal.

20. The method of claim 17, wherein:
the persuasion delivery device further includes a speaker and an orifice; and the method further comprising:

dispensing a treat from the bowl, sounds from the speaker, and smells from the orifice to attract the animal into the analysis zone.

* * * * *